(12) United States Patent
Pan et al.

(10) Patent No.: US 9,289,510 B2
(45) Date of Patent: Mar. 22, 2016

(54) POLYMERIC DRUG DELIVERY CONJUGATES AND METHODS OF MAKING AND USING THEREOF

(75) Inventors: Huaizhong Pan, Salt Lake City, UT (US); Jiyuan Yang, Salt Lake City, UT (US); Pavla Kopeckova, Salt Lake City, UT (US); Kui Luo, Salt Lake City, UT (US); Jindrich Kopecek, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 296 days.

(21) Appl. No.: 13/583,270

(22) PCT Filed: Mar. 7, 2011

(86) PCT No.: PCT/US2011/027337
§ 371 (c)(1),
(2), (4) Date: Jan. 9, 2013

(87) PCT Pub. No.: WO2011/112482
PCT Pub. Date: Sep. 15, 2011

(65) Prior Publication Data
US 2013/0156722 A1 Jun. 20, 2013

Related U.S. Application Data

(60) Provisional application No. 61/311,459, filed on Mar. 8, 2010.

(51) Int. Cl.
*A61K 47/48* (2006.01)

(52) U.S. Cl.
CPC ..... *A61K 47/48338* (2013.01); *A61K 47/48176* (2013.01)

(58) Field of Classification Search
CPC .................. A61K 47/48176; A61K 47/48338
USPC ........................ 424/78.27; 525/54.1
See application file for complete search history.

(56) References Cited

U.S. PATENT DOCUMENTS

| | | | |
|---|---|---|---|
| 3,931,111 A | 1/1976 | Kopecek et al. | |
| 4,062,831 A | 12/1977 | Kopecek et al. | |
| 4,074,039 A | 2/1978 | Lim et al. | |
| 4,097,470 A | 6/1978 | Drobnik et al. | |
| 5,037,883 A | 8/1991 | Kopecek et al. | |
| 5,258,453 A | 11/1993 | Kopecek et al. | |
| 7,179,487 B1 | 2/2007 | Kopecek et al. | |
| 8,703,114 B2 | 4/2014 | Satchi-Fainaro et al. | |
| 2004/0228831 A1* | 11/2004 | Belinka et al. | 424/78.27 |
| 2005/0123600 A1 | 6/2005 | Trubetskoy et al. | |
| 2005/0287114 A1* | 12/2005 | Wang et al. | 424/78.27 |
| 2007/0287680 A1* | 12/2007 | Cuchelkar et al. | 514/44 |
| 2009/0297609 A1 | 12/2009 | Shoichet et al. | |
| 2013/0156722 A1* | 6/2013 | Kopeckova et al. | 424/78.27 |

OTHER PUBLICATIONS

Dvorak, et al. (Journal of Controlled Release; 60 (1999) 321-332).*
Kopecek et al. ( J. Controlled Release 190 (2014) pp. 299-303).*
Kopecek et al. ( J. Controlled Release 218 (2015) 36-44).*
Lammers et al. "Effect of physicochemical modification on the biodistribution and tumor accumulation of HPMA copolymers." Journal of Controlled Release 2005, 110: 103-118.
Dvorak et al. "High-molecular weight HPMA copolymer-adriamycin conjugates." Journal of Controlled Release 1999, 60: 321-332.
International Search Report dated Oct. 11, 2011 for international application No. PCT/US2011/027337.
Office Action for Japanese Patent Application No. 2012-557145 dated Mar. 3, 2015.
Yang, J. et al. "Fret-trackable biodegradable HPMA copolymer-epirubicin conjugates for ovarian carcinoma therapy," 2015, J. Controlled Release, 218:36-44.
Yang, J. et al. "Macromolecular therapeutics," 2014, J. Controlled Release, 190:288-303.

* cited by examiner

*Primary Examiner* — Anna Falkowitz
(74) *Attorney, Agent, or Firm* — Gardner Groff Greenwald & Villanueva, PC

(57) ABSTRACT

Described herein are biodegradable drug delivery conjugates for effectively delivering bioactive agents to a subject. The drug delivery conjugates comprise a water-soluble high molecular weight linear biodegradable polymer backbone comprising a plurality of linear water-soluble polymeric segments connected to one another by a first (main-chain) cleavable linker, wherein a bioactive agent is covalently bonded to at least one water-soluble polymeric segment, at least one cleavable linker, or a combination thereof. The conjugates possess numerous advantages over prior art delivery conjugates. Also described herein are methods for making and using the conjugates.

10 Claims, 7 Drawing Sheets

SEQUENCE LISTING

```
<160> NUMBER OF SEQ ID NOS: 24

<210> SEQ ID NO 1
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: X is norleucine

<400> SEQUENCE: 1

Gly Pro Xaa
1

<210> SEQ ID NO 2
<211> LENGTH: 2
<212> TYPE: PRT
<213> ORGANISM: Artificial Sequence
<220> FEATURE:
<223> OTHER INFORMATION: Synthetic Construct
      220>
<221> NAME/KEY: MISC_FEATURE
<222> LOCATION: (1)..(1)
<223> OTHER INFORMATION: X is citrulline

<400> SEQUENCE: 2

Xaa Phe
1

<210> SEQ ID NO 3
<211> LENGTH: 2
<212> TYPE: PRT
<213> ORGANISM: Artificial Sequence
<220> FEATURE:
<223> OTHER INFORMATION: Synthetic Construct

<400> SEQUENCE: 3

Lys Lys
1

<210> SEQ ID NO 4
<211> LENGTH: 2
<212> TYPE: PRT
<213> ORGANISM: Artificial Sequence
<220> FEATURE:
<223> OTHER INFORMATION: Synthetic Construct

<400> SEQUENCE: 4
```

Phe Lys
1

<210> SEQ ID NO 5
<211> LENGTH: 2
<212> TYPE: PRT
<213> ORGANISM: Artificial Sequence
<220> FEATURE:
<223> OTHER INFORMATION: Synthetic Construct

<400> SEQUENCE: 5

Arg Arg
1

<210> SEQ ID NO 6
<211> LENGTH: 2
<212> TYPE: PRT
<213> ORGANISM: Artificial Sequence
<220> FEATURE:
<223> OTHER INFORMATION: Synthetic Construct
      220>
<221> NAME/KEY: MISC_FEATURE
<222> LOCATION: (2)..(2)
<223> OTHER INFORMATION: X is citrulline

<400> SEQUENCE: 6

Val Xaa
1

<210> SEQ ID NO 7
<211> LENGTH: 3
<212> TYPE: PRT
<213> ORGANISM: Artificial Sequence
<220> FEATURE:
<223> OTHER INFORMATION: Synthetic Construct

<400> SEQUENCE: 7

Gly Phe Gly
1

<210> SEQ ID NO 8
<211> LENGTH: 3
<212> TYPE: PRT
<213> ORGANISM: Artificial Sequence
<220> FEATURE:
<223> OTHER INFORMATION: Synthetic Construct

<400> SEQUENCE: 8

Gly Phe Phe
1

<210> SEQ ID NO 9
<211> LENGTH: 3
<212> TYPE: PRT
<213> ORGANISM: Artificial Sequence
<220> FEATURE:
<223> OTHER INFORMATION: Synthetic Construct

<400> SEQUENCE: 9

Gly Leu Gly
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

Gly Val Ala
1

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Gly Phe Ala Gly Leu Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Leu Ala Ala Val Ala
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Gly Phe Leu Gly
1

<210> SEQ ID NO 14
<211> LENGTH: 4
<212> TYPE: PRT
<213> ORGANISM: Artificial Sequence
<220> FEATURE:
<223> OTHER INFORMATION: Synthetic Construct

<400> SEQUENCE: 14

Gly Phe Phe Leu
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Gly Leu Leu Gly
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

```
<400> SEQUENCE: 16

Gly Phe Tyr Ala
1

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Gly Phe Gly Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Ala Gly Val Phe
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Construct

<400> SEQUENCE: 19

Gly Phe Phe Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Gly Phe Leu Gly Phe
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Gly Gly Phe Leu Gly Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22
```

```
Glu Ser Phe Arg Phe Lys
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic Construct

<400> SEQUENCE: 23

Gly Leu Phe Gly
1

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gly Phe Leu Gly Lys Gly Leu Phe Gly
1               5
```

POLYMERIC DRUG DELIVERY CONJUGATES AND METHODS OF MAKING AND USING THEREOF

CROSS REFERENCE TO RELATED APPLICATION

This application is a U.S. national phase application under 35 USC 371 of international application number PCT/US2011/027337, filed Mar. 7, 2011, which claims priority upon U.S. provisional application Ser. No. 61/311,459, filed Mar. 8, 2010. This application is hereby incorporated by reference in its entirety for all of its teachings.

ACKNOWLEDGEMENTS

This invention was made with government support under CA132831, CA051578, GM069847, and EB005288 awarded by the National Institutes of Health. The government has certain rights in the invention.

CROSS REFERENCE TO SEQUENCE LISTING

Peptides described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Although traditional synthetic polymer-drug conjugates provide many benefits over low molecular weight drugs, the molecular weight of synthetic polymer drug carriers (e.g., HPMA or PEG) is limited by the renal threshold. This results in fast elimination of the conjugate via glomerular filtration, low circulation time, and inefficient accumulation in tumor tissue by enhanced permeability and retention (EPR) effect.

Molecular weight and molecular weight distribution (MWD) of a drug carrier conjugate are crucial for effective functioning. The renal threshold limits the hydrodynamic radius of the conjugate to less than 45 Å. Thus, the molecular weight of polymeric carriers should be less than 30-40 kDa (the exact value depends on detailed structure). However, a decrease in molecular weight lowers the retention time of the conjugate in the circulatory system with concomitant decrease in pharmaceutical efficiency. An ideal drug carrier should possess a sufficiently high molecular weight to prevent rapid loss by glomerular filtration. High-molecular weight (long-circulating) polymer conjugates accumulate efficiently in tumor tissue due to the EPR effect. However, if they possess a nondegradable backbone, they may deposit and accumulate in various organs, impairing biocompatibility.

SUMMARY

Described herein are biodegradable drug delivery conjugates for effectively delivering bioactive agents to a subject. The drug delivery conjugates comprise a water-soluble high molecular weight linear biodegradable polymer backbone comprising a plurality of linear water-soluble polymeric segments connected to one another by a first (i.e., main-chain) cleavable linker, wherein a bioactive agent is covalently bonded to at least one water-soluble polymeric segment, at least one cleavable linker, or a combination thereof. The conjugates possess numerous advantages over prior art delivery conjugates. Also described herein are methods for making and using the conjugates. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
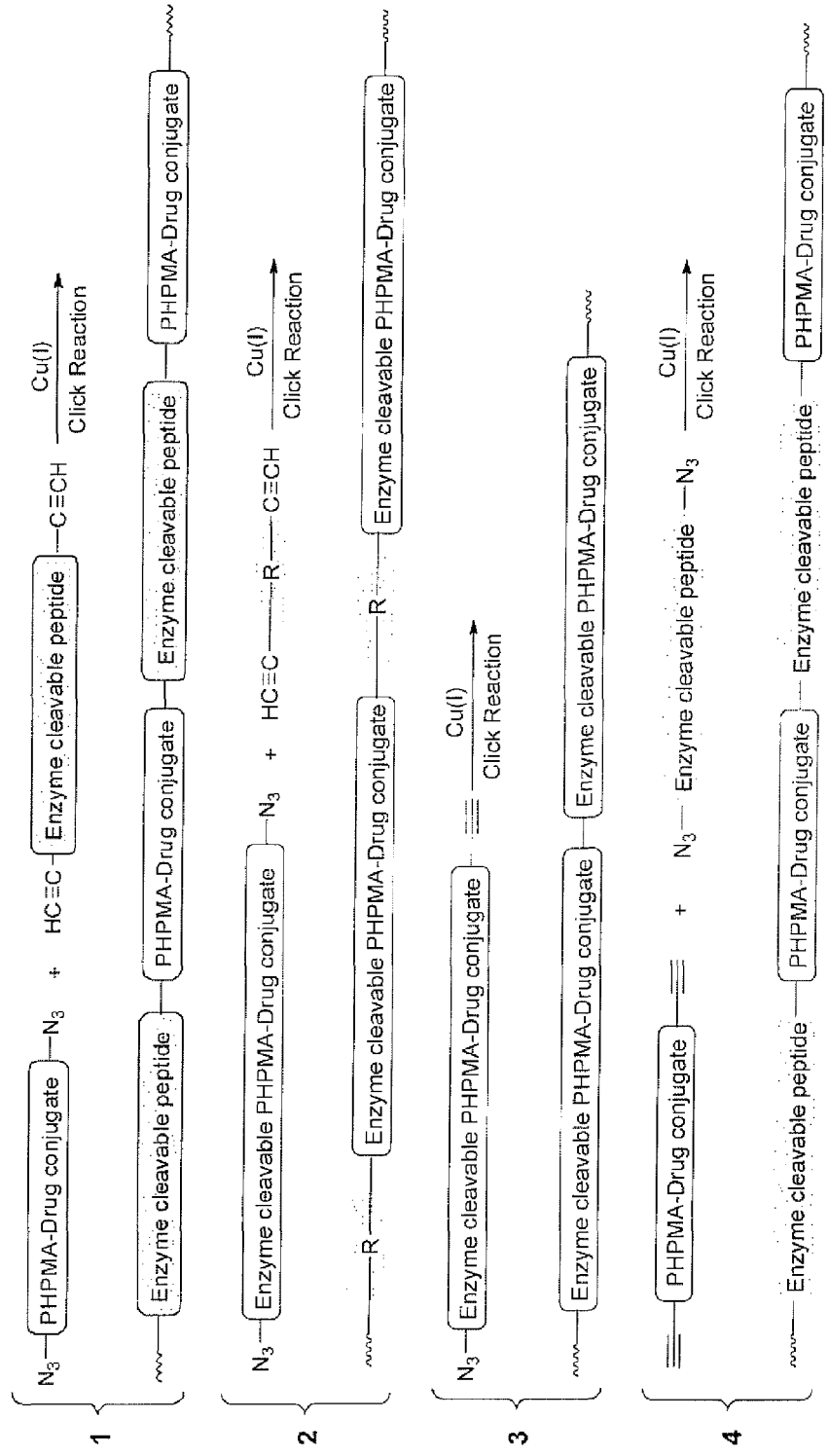
FIG. 1 shows exemplary reaction schemes for preparing the conjugates described herein.
Figure 1:
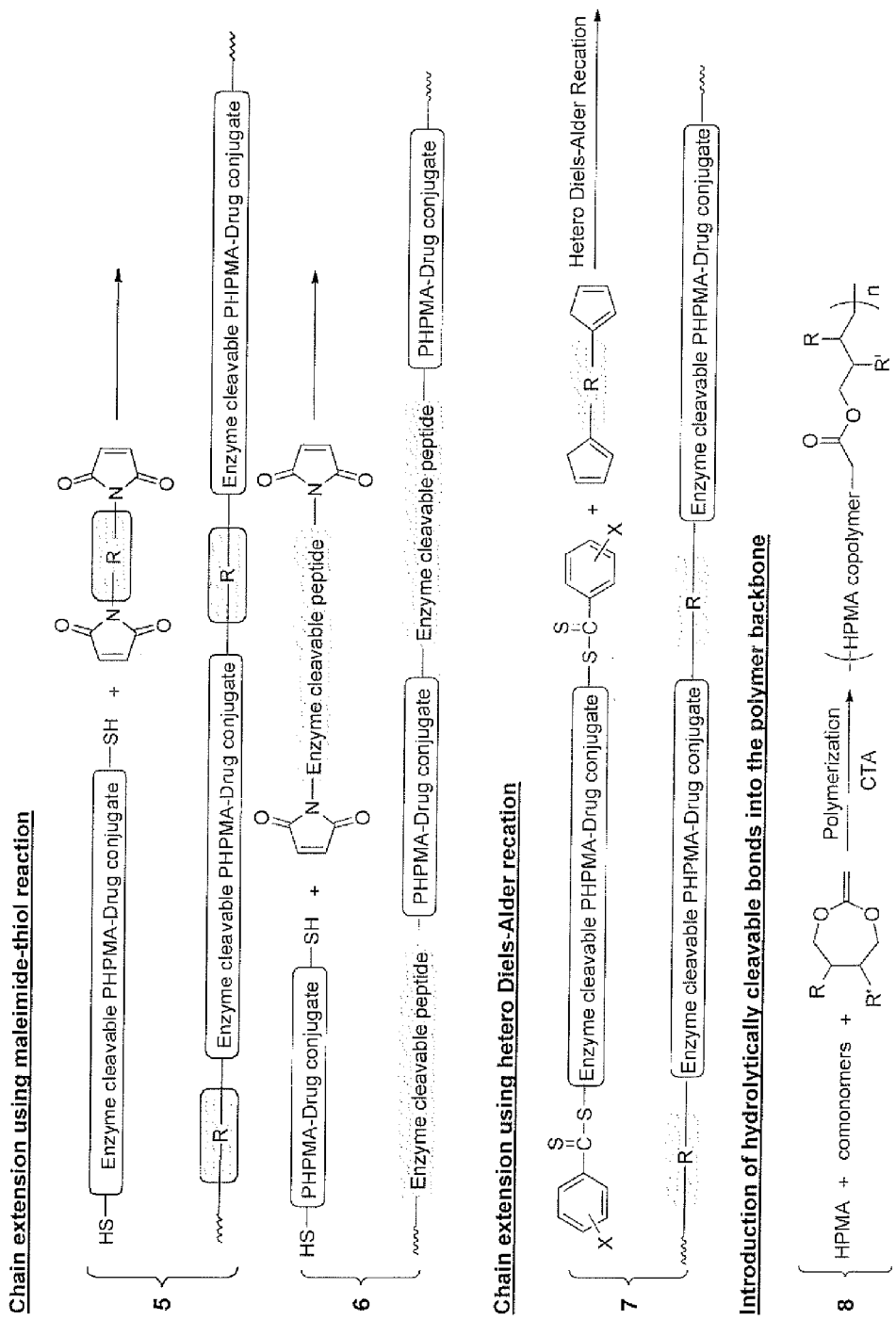
Figure 1:
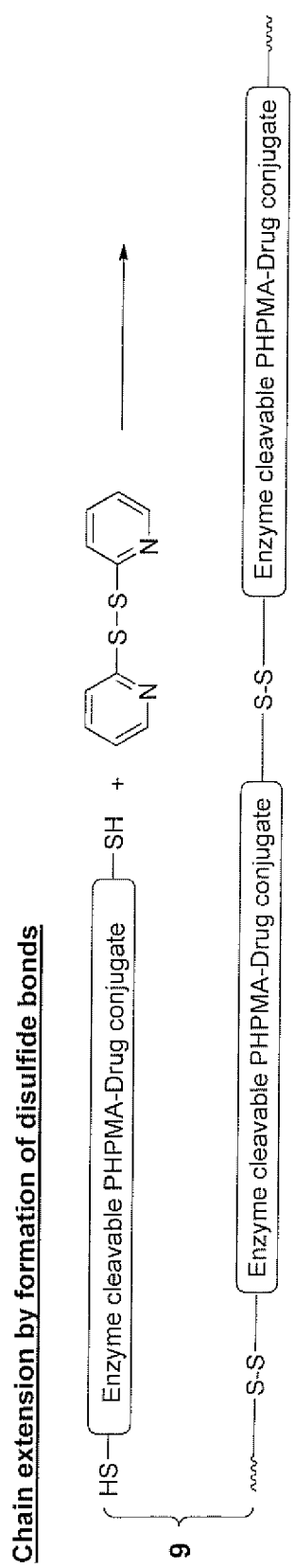

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a monomer" includes mixtures of two or more such monomers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, an amino acid that contains at least one —$NH_2$ group can be represented by the formula H—Y—OH, where Y is the remainder (i.e., residue, —HN—CHR—CO—) of the amino acid molecule.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a $C_3$ to $C_8$ cyclic group. The cycloalkyl can be fully saturated or possess one or more degrees of unsaturation. The term "cycloalkyl" also includes a cycloalkyl group that has at least one heteroatom incorporated within the ring. Examples of heteroatoms include, but are not limited to, nitrogen, oxygen, sulfur, and phosphorus. The cycloalkyl group can be substituted or unsubstituted.

The term "hydrophilic group" as used herein is any group that enhances the water-solubility of the conjugate. The hydrophilic groups can be present on one or more monomers used to produce the water soluble unit in the conjugate. Examples of such groups include, but are not limited to, a hydroxyl group, an amino group, a thiol group, a carboxyl group, a $SO_3H$ group, or a zwitterionic group.

Variables such as $AA_1$, $AA_2$, L, $L^1$, X, Y, and Z used throughout the application are the same variables as previously defined unless stated to the contrary.

Described herein are drug delivery conjugates useful in the delivery of bioactive agents. The conjugates comprise a water-soluble high molecular weight linear biodegradable polymer backbone comprising a plurality of linear water-soluble polymeric segments connected to one another by a first (i.e., main-chain) cleavable linker, wherein a bioactive agent is covalently bonded to at least one water-soluble polymeric segment, at least one cleavable linker, or a combination thereof. Each component of the conjugate is described in detail below.

The conjugates are linear polymers having a molecular weight from 50 kDa to 750 kDa. In one aspect, the molecular weight of the conjugate is 50 kDa, 60 kDa, 70 kDa, 80 kDa, 90 kDa, 100 kDa, 125 kDa, 150 kDa, 175 kDa, 200 kDa, 225 kDa, 250 kDa, 275 kDa, 300 kDa, 325 kDa, 350 kDa, 375 kDa, 400 kDa, 425 kDa, 450 kDa, 475 kDa, 500 kDa, 550 kDa, 600 kDa, 650 kDa, 700 kDa, 750 kDa or any range based on these values. The conjugates are linear polymers and not branched polymers. In other words, the conjugate has a single linear polymeric backbone that acts as anchor for the attachment of anticancer drugs, targeting moieties (such as antibodies, antibody fragments, aptamers, peptides, oligosaccharides, etc.).

As will be discussed in greater detail below, the bioactive agent can be pendant to the polymeric backbone of the conjugate via a cleavable linker. However, the pendant bioactive agent is not a polymeric group in itself and, thus, is not a "polymeric branch." Each component of the conjugate is discussed in detail below.

The water-soluble component of the conjugate is a polymeric segment having a relatively low molecular weight. In one aspect, the water-soluble polymeric segment has a molecular weight of 5 kDa, 10 kDa, 15 kDa, 20 kDa, 25 kDa, 30 kDa, 35 kDa, or 40 kDa. The water-soluble polymeric segment has one or more hydrophilic groups that interact with water and make the resultant conjugate soluble in water. Examples of such groups include any organic groups that readily receive or donate protons such as, for example, a hydroxyl group, an amino group, a thiol group, a carboxyl group, a $SO_3H$ group, a zwitterionic group, and the like.

In one aspect, the water-soluble polymeric segment comprises the polymerization product of one or more unsaturated water-soluble monomers. Water soluble monomers having the formula I can be used to produce the water-soluble polymeric segment

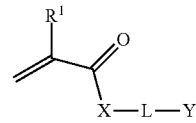

I wherein $R^1$ is hydrogen or methyl;
X is O or $NR^2$, wherein $R^2$ is hydrogen or an alkyl group;
L is an alkyl group, an aryl group, or a cycloalkyl group; and
Y is a hydrophilic group.

In one aspect, $R^1$ is methyl, X is NH, and L is a $C_1$-$C_5$ alkyl group such as, for example, a methylene group, an ethylene group, or an isopropylene group. In another aspect, the water soluble monomer comprises an N-substituted methacrylamide, an N,N-disubstituted acrylamide, a hydrophilic ester of methacrylic or acrylic acid, an N-vinylpyrrolidone, an N-acryloylmorpholine, a sulfoethylmethacrylate, an acrylic acid, a methacrylic acid, or any combination thereof. In another aspect, the water soluble monomer comprises N-(2-hydroxypropyl)methacrylamide (HPMA), N-[3-(N'-dicarboxymethyl)aminopropyl]methacrylamide (DAMA), N-methacryloylglycylphenylalanylleucylglycine-aminomalonic acid (MA-GFLG-diCOOH), N-(3-aminopropyl)methacrylamide, or any combination thereof.

The water-soluble polymeric segment can be made using techniques known in the art. The Examples also provide exemplary synthetic protocols for making the water-soluble polymeric segment useful in the conjugates described herein.

In one aspect, the first cleavable linker present in the conjugate is composed of one or more amino acid residues. The first cleavable linker is also referred to herein as the main-chain cleavable linker, where the linker is present in the polymer backbone. For example, the first cleavable linker can be a peptide having from 2 to 13 amino acid residues. By varying the amino acid or sequence of amino acids, it is possible to design the first cleavable linker so that it is cleaved under specific conditions. It is desirable that the first cleavable linker be considerably stable in the bloodstream but degrade when it comes into contact with an enzyme.

The first cleavable linker can be cleaved by an enzyme. In one aspect, the linker is cleaved by a lysosomal enzyme. Lysosomal enzymes include a number of proteinases with the ability to hydrolyse peptide linkages (e.g., cathepsin B, L, D or K). The rate of lysosomal hydrolysis of the cleavable linker is dependent on both the number and the nature of the amino acid residues present in the linker. This is a reflection of both steric and structural factors. In one aspect, the first cleavable linker is a peptide having the amino acid sequence -Gly-Pro-Nle- (SEQ ID NO 1); -Cit-Phe-(SEQ ID NO 2); -Lys-Lys-(SEQ ID NO 3); -Phe-Lys- (SEQ ID NO 4); -Arg-Arg-(SEQ ID NO 5); Val-Cit (SEQ ID NO 6); Gly-Phe-Gly (SEQ ID NO 7); Gly-Phe-Phe (SEQ ID NO 8); Gly-Leu-Gly (SEQ ID NO 9); Gly-Val-Ala (SEQ ID NO 10); Gly-Phe-Ala; Gly-Leu-Phe (SEQ ID NO 11); Gly-Leu-Ala; Ala-Val-Ala (SEQ ID NO 12); Gly-Phe-Leu-Gly (SEQ ID NO 13); Gly-Phe-Phe-Leu (SEQ ID NO 14); Gly-Leu-Leu-Gly (SEQ ID NO 15); Gly-Phe-Tyr-Ala (SEQ ID NO 16); Gly-Phe-Gly-Phe (SEQ ID NO 17); Ala-Gly-Val-Phe (SEQ ID NO 18); Gly-Phe-Phe-Gly (SEQ ID NO 19); Gly-Phe-Leu-Gly-Phe (SEQ ID NO 20); Gly-Gly-Phe-Leu-Gly-Phe (SEQ ID NO 21); and Gln-Ser-Phe-Arg-Phe-Lys (SEQ ID NO 22).

In another aspect, the first cleavable linker has the formula III

-(AA$_1$)-K-(AA$_2$)- (III)

wherein AA$_1$ and AA$_2$ are the same or different amino acid sequence comprising up to six amino acids, and K is lysine, ornithine, or a diamine (e.g., ethylenediamine, hexamethylenediamine, etc.). AA$_1$ and AA$_2$ can be any amino acid sequence listed above.

In other aspects, the first cleavable linker is a group that can be cleaved hydrolytically. For example, the linker can be cleaved by a change in pH (e.g., carboxyalkylmaleic linker or an ascorbic linker), or a combination thereof.

The first cleavable linker can be made using techniques known in the art. The Examples provide exemplary synthetic protocols for making the cleavable linkers. Methods for linking the cleavable linker to the water-soluble polymeric segment are discussed in detail below.

A variety of bioactive agents can be used herein. The bioactive agent can be covalently bonded to at least one water-soluble polymeric segment, at least one cleavable linker, or a combination thereof in the conjugate. Methods for covalently bonding the bioactive agent to the conjugate are described in detail below, with exemplary procedures in the Examples. In one aspect, two or more different bioactive agents are covalently bonded to the conjugate. In one aspect, the bioactive agent is an anti-cancer agent, an antimicrobial agent, an antiparasitic agent, an anti-inflammatory agent, a cardio-vascular drug, or a drug acting on the nervous system. In another aspect, the bioactive agent comprises paclitaxel, docetaxel, gemcitabine, platinates (cis-platin, carboplatin, DACH-Pt), doxorubicin, geldanamycin, or 9-aminocamptothecin.

In one aspect, when the bioactive agent is covalently bonded to the water-soluble polymeric segment, the water-soluble polymeric segment comprises the polymerization product of one or more unsaturated water-soluble monomers as discussed above and a monomer comprising the formula II

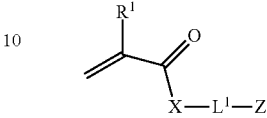

wherein R$^1$ is hydrogen or methyl;
X is O or NR$^2$, wherein R$^2$ is hydrogen or an alkyl group;
L$^1$ is a second (i.e., side-chain) cleavable linker; and
Z is the bioactive agent.

In this aspect, the bioactive agent is linked to the unsaturated monomer via a second linker L$^1$. The second cleavable linker is also referred to herein as the side-chain linker, where the linker is not part of the polymeric backbone but pendant to the backbone. The second cleavable linker can be the same or different peptide as that of the first cleavable linker in the polymer backbone of the conjugate. Exemplary methods for making compounds having the formula II are provided in the Examples.

In certain aspects, the conjugate has one or more targeting groups covalently attached to it in order to improve the specificity of the conjugate to cells. For example, the targeting group can be covalently attached to the water-soluble polymeric segment, the first cleavable linker, or a combination thereof. The targeting group can be linked directly to the polymer backbone either by an amide or an ester bond that is without a spacer, or can be linked through an amino acid or peptide spacer. The targeting group should be accessible by the specific receptors on the target cells, which is to a large extent a function of the geometry of the polymeric drug molecule.

In one aspect, the targeting group is attached to methacrylamide, methacrylic acid or an N-methacryloylated amino acid or peptide. For example, referring to formula II above, Z can be a targeting group instead of a bioactive agent, which can be polymerized with other monomers having the formula II that do not contain a bioactive agent.

As targeting groups, structures complementary to cell surface antigens or receptors can be used. In one aspect, the targeting group is an antibody, an antibody fragment, a saccharide, or an epitope binding peptide, or an aptamer. For example, the targeting group can be a monosaccharide, disaccharide, oligosaccharide or methacryloylated saccharide unit bound by an amide bond, an antibody, such as IgG (rat immunoglobulin) or antibody fragment, or a protein, such as transferrin or melanocyte-stimulating hormone (MSH), or a peptide. In another aspect, the targeting group is galactosamine, fucosylamine, lactose; folate derivatives; hormones, e.g. MSH, secretin; opiates; monoclonal and polyclonal antibodies. In one aspect, the targeting group is Fab' from the OV-TL16 antibody specific to CD47 (expressed on the majority of ovarian carcinoma cells) or antibody toward prostate specific membrane antigen (PMSA).

The conjugates described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 6.5 to about 7.5, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the conjugates described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the conjugates described herein can contain combinations of two or more pharmaceutically-acceptable compounds. Examples of such compounds include, but are not limited to, antimicrobial agents, other antiinflammatory agents, other anticancer or antimetastatic agents, analgesics, anesthetics, and the like.

The pharmaceutical compositions can be prepared using techniques known in the art. In one aspect, the composition is prepared by admixing a conjugate described herein with a pharmaceutically acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound.

It will be appreciated that the actual preferred amounts of conjugate in a specified case will vary according to the specific compound being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Methods for preparing the conjugates are also described herein. FIG. 1 provides general reaction schemes for producing the conjugates. Referring to FIG. 1, reactions 1 and 2 involve coupling bis-azide compounds to bis-alkyne compounds using a click reaction to produce the conjugate. In equation 1, the bis-azide compound is a water-soluble polymer (polyHPMA) with the bioactive agent (i.e., drug) covalently bonded to the polymer. The bis-azide in equation 1 is coupled with a bis-alkyne composed of an enzymatic cleavable peptide (i.e., the first (main-chain) cleavable linker) to produce the conjugate. Another approach is depicted in equation 2, where the bis-azide compound is an enzymatic cleavable peptide having the bioactive agent covalently bound to the polymer. In equation 2, R is a linker capped with alkyne groups.

Another approach in equation 3 is click coupling of hetero telechelic HPMA copolymer containing conjugated bioactive agents (i.e., drugs) and enzymatically cleavable peptides to prepare multisegments copolymer conjugates. The hetero telechelic HPMA copolymer conjugates can be synthesized by RAFT copolymerization using azido or alkyne modified peptide containing chain transfer agent.

Equation 4 depicts an approach where the bis-alkyne compound is a water-soluble polymer (polyHPMA) with the bioactive agent (i.e., drug) covalently bound to the polymer.

Equations 5 and 6 in FIG. 1 describe an example of thiol-ene (e.g., maleimide-thiol) reaction for producing the conjugate. Thiol-terminated polymers can be easily prepared via RAFT polymerization. High efficient thiol-ene reactions do not need metal catalyst, are compatible with water and oxygen and can be performed in the absence of solvent and under photochemical initiation.

Equation 7 in FIG. 1 provides an example of hetero Diels-Alder reaction for the extension of HPMA copolymer chains. This reaction is highly efficient and does not require a catalyst.

Equation 8 in FIG. 1 provides a synthetic strategy for introducing hydrolytically cleavable bonds into the polymer backbone of the conjugate. The 1,3-dioxepane undergoes polymerization and ring-opening to produce a polymer with ester linkages. The ester linkages can be cleaved by adjusting the pH in order to hydrolyze the ester group and cleave the conjugate.

Equation 9 in FIG. 1 provides an example of extension of HPMA copolymer conjugates by using oxidation agents such as dipyridyldisulfide, DMSO, etc.

The Examples provide numerous synthetic strategies and procedures for making the conjugates described herein.

The conjugates described herein are water-soluble and biodegradable. The conjugates are stable during circulation, possess long retention times, and have better targeting properties. Moreover, they can be eliminated from the body after cleavage of the linker (e.g., enzymatically, hydrolytically, etc.). The synthesis of the conjugates as described herein is versatile, which permits the preparation of a large variation of polymer structures with tailor-made properties such as circulation time and rate/site of degradation. Moreover, the conjugates possess the additional advantages of (1) protecting unstable drugs from deterioration; (2) decreased non-specific toxicity of the conjugated drug; (3) increased active accumulation of the drug at the targeted site by targeting and/or increased passive accumulation of the drug at the tumor site by the EPR effect; and (4) the ability to deliver two or more drugs with different (complementary) properties to the same target site, which enhances the drug efficiency by cooperative and/or synergistic effects. These are just some of the reasons why the conjugates described herein are effective in the delivery of bioactive agents to a subject.

It is understood that any given particular aspect of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Abbreviations. CTA, chain transfer agent; CTP, 4-cyano-4-thiobenzoylsulfanyl-pentanoic acid; Da, Dalton; DCC, dicyclohexylcarbodiimide; DCM, dichloromethane; DCU, dicyclohexylurea; Dde, 1-(4,4-dimethyl-2,6-dioxacyclohexylidene) ethyl; DIAD, diisopropyl azodicarboxylate; DIPEA, N,N-diisopropylethylamine; DMAP, 4-dimethylaminopyridine; DMF, N,N-dimethylformamide; DOX, doxorubicin; DTX, docetaxel; EDCI, 1-ethyl-3-(3-dimethylaminopropyl)carbodiimide; EPR, enhanced permeability and retention; EtOAc, ethyl acetate; Fmoc, fluorenylmethyloxycarbonyl; HBTU, O-benzotriazole-N,N,N',N'-tetramethyl-uronium-hexafluoro-phosphate; HOBt, 1-hydroxybenzotriazole; HPMA, N-(2-hydroxypropyl)methacrylamide; MA, methacryloyl; MAL, maleimide; MALDI-TOF, matrix-assisted laser desorption-ionization time-of-flight; MA-NH$_2$, 3-aminopropylmethacrylamide; Mn, number average molecular weight; MS, mass spectrometry; Mw, weight average molecular weight; MWD, molecular weight distribution; NMP, 1-methyl-2-pyrrolidinone; PDI, polydispersity=Mw/Mn; PEG, poly(ethylene glycol); PHPMA; polyHPMA; PSMA, prostate specific membrane antigen; RAFT, reversible addition-fragmentation chain transfer; RP-HPLC, reverse phase high performance liquid chromatography; SEC, size exclusion chromatography; SPPS, solid phase peptide synthesis; TCEP.HCl, tris(2-carboxyethyl)phosphine hydrochloride; TFA, trifluoroacetic acid; TLC, thin layer chromatography; TT, thiazolidine-2-thione; TTC, trithiocarbonate.

Examples of Synthesis of Polymerizable Drug Derivatives and Comonomers for the Introduction of Functional Groups

Example 1

Synthesis of MA-GFLG-Gemcitabine

Synthesis of N-methacryloylglycylphenylalanylleucylglycyl-thiazolidine-2-thione (MA-GFLG-TT)

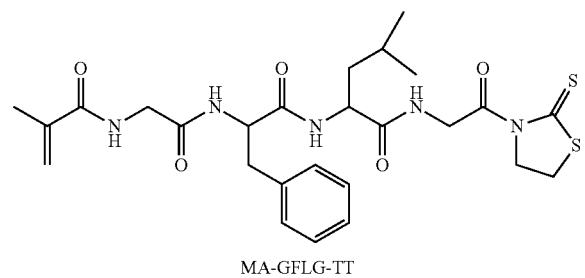 [SMILES: C=C(C)C(=O)NCC(=O)NC(Cc1ccccc1)C(=O)NC(CC(C)C)C(=O)NCC(=O)N1CCSC1=S]

MA-GFLG-TT

The synthesis of MA-GFLG-TT followed a published procedure [V. Šubr et al., Reactive & Functional Polymers 66 1525-1538 (2006)] with a slight modification. Under nitrogen atmosphere, N-methacryloylglycylphenylalanylleucylglycine (MA-GFLG-OH; 320 mg, 0.7 mmol), 2-mercaptothiazoline (83.5 mg, 0.7 mmol) and DMAP (85.5 mg, 0.7 mmol) were dissolved in dichloromethane (DCM) (20 mL). The solution was stirred for 5 min −10° C., EDCI (134.2 mg, 0.7 mmol) was added and the solution was stirred −10° C. for 3 h and at room temperature for another 12 h. After reaction, 50 mL DCM was added, the solution was washed with NaHCO$_3$ aq. (0.1 M), HCl (0.1 M) and then NaCl aq. The organic layer was dried (MgSO$_4$), solvent removed by rotary evaporation and the crude product was purified by column chromatography (silica gel 60 Å, 200-400 mesh, EtOAc: CH$_3$OH, 15:1) and then recrystallized from DCM to give yellow powder in 51.9% yield. The structure was confirmed by $^1$H NMR and $^{13}$C NMR spectroscopy. $^1$H NMR (300 MHz, CDCl$_3$, δ in ppm): 0.86 (m, 6 H, CH(CH$_3$)$_2$), 1.51 (m, 2H, CHCH$_2$CH(CH$_3$)$_2$), 1.66 (m, 1H, CH(CH$_3$)$_2$), 1.91 (s, 3 H, CCH$_3$), 3.03 (m, 2 H, Ph-CH$_2$), 3.33 (t, 2 H, SCH$_2$), 4.00 (s, 2 H, NHCH$_2$CO), 4.54 (t, 2 H, NCH$_2$CH$_2$S), 4.63 (m, 1 H, NHCHCO), 4.73 (m, 1 H, NHCHCO), 4.81 (s, 2 H, NHCH$_2$CO), 5.39 (s, 1H, C=CH$_2$), 5.77 (s, 1H, C=CH$_2$), 6.99 (s, 1 H, NH), 7.18 (m, 6 H, NH, Ph-H), 7.56-7.80 (m, 2 H, NH). $^{13}$C NMR (75 MHz, CDCl$_3$, δ in ppm): 201.78, 172.6, 170.92, 170.57, 169.33, 168.99, 139.02, 136.46, 129.77, 128.80, 127.21, 121.31, 56.11, 54.89, 51.83, 46.85, 43.61, 41.81, 39.37, 29.37, 24.88, 22.86, 18.21.

Synthesis of N-methacyloylglycylphenylalanylleucylglycyl-gemcitabine (MA-GFLG-gemcitabine)

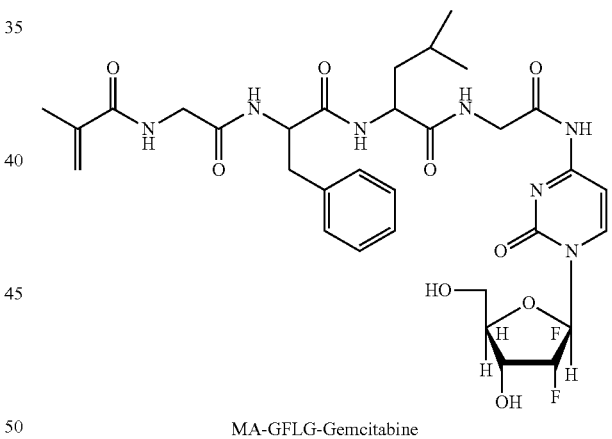

MA-GFLG-Gemcitabine

MA-GFLG-TT (90 mg, 0.16 mmol) and gemcitabine hydrochloride (44.95 mg, 0.15 mmol) were dissolved in pyridine (5 mL) under nitrogen atmosphere. The solution was stirred 50° C. for 12 h and then the solvent was removed by rotary evaporation. The crude product was purified by column chromatography (silica gel 60 Å, 200-400 mesh, DCM: CH$_3$OH, 6:1) to give white solid in 66.1% yield. The structure was confirmed by $^1$H NMR spectroscopy and matrix assisted laser desorption ionization time-of-light (MALDI-TOF) mass spectrometry. MALDI-TOF MS: m/z 706.22 (M+H)$^+$, 728.21 (M+Na)$^+$, 744.19 (M+K)$^+$.

Using the same approach, polymerizable gemcitabine derivatives containing enzyme degradable oligopeptide sequences can be synthesized, such as MA-GFTA-gemcitabine; MA-GFA-gemcitabine; MA-GLA-gemcitabine; MA-GIA-gemcitabine; MA-Acap-V-Cit-gemcitabine (Acap is N$^\epsilon$-aminocaproic acid; Cit is citruline).

Example 2

Synthesis of N-methacryloylglycylphenylalanylleucylglycyl-aminomalonic acid (MA-GFLG-malonic Acid)

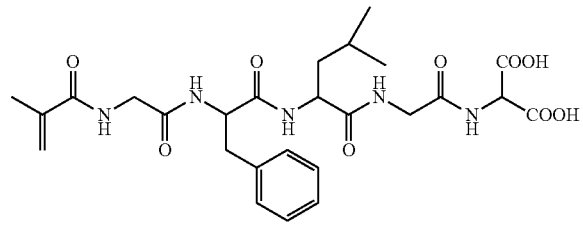 [SMILES: C=C(C)C(=O)NCC(=O)NC(Cc1ccccc1)C(=O)NC(CC(C)C)C(=O)NCC(=O)NC(C(=O)O)C(=O)O]

Under nitrogen atmosphere, MA-GFLG-OH (400 mg, 0.87 mmol), diethyl aminomalonate hydrochloride (184 mg, 0.87 mmol) and HOBt (121.6 mg, 0.9 mmol) were dissolved in anhydrous DMF (10 mL). The solution was stirred for 5 min in ice bath, DIPEA (310 mg, 2.4 mmol) was added and then HBTU (341.3 mg, 0.9 mmol) was added. The solution was stirred in ice bath for 30 min and at room temperature overnight. After reaction, ethyl acetate (EtOAc) (50 mL) was added and the organic solution was washed with NaHCO$_3$ aq. (satd.) and HCl (1 M) then NaCl aq. The solution was dried (MgSO$_4$) and the volume decreased to 15 mL by rotary evaporation. The product (MA-GFLG-diCOOEt) was obtained by recrystallization from EtOAc and ether in 85% yield and the structure was characterized by MALDI-TOF mass spectrometry. MALDI-TOF MS: m/z 640.10 [(M+Na)$^+$, C$_{30}$H$_{43}$N$_5$O$_9$Na]. MA-GFLG-diCOOEt (300 mg, 0.49 mmol) was dissolved in CH$_3$OH (10 mL). The solution was stirred for 5 min in ice bath, then NaOH (1 M, 0.49 mmol) in CH$_3$OH (5 mL) was added dropwise. The solution was stirred in ice bath for additional 2 h and at room temperature for another 1 h. After reaction, the MeOH was removed, the solution was acidified to pH=2~3 with HCl (1 M), separated, the aq. was extracted with EtOAc (25×3). The organic solution was dried (MgSO$_4$) and the solvent removed by rotary evaporation. The final product (MA-GFLG-diCOOH) was obtained by recrystallization from EtOAc in 76% yield.

Example 3

Synthesis of 2'-O-methacryloylglycylphenylalanylleucylglycyl-docetaxel (MA-GFLG-docetaxel)

MA-Gly-Phe-Leu-Gly-OH (84 mg, 0.18 mmol), docetaxel (147 mg, 0.18 mmol) and DMAP (21 mg, 0.17 mmol) were dissolved in 0.75 mL DMF, cooled to 0° C. and dicyclohexylcarbodiimide (DCC; 45 mg, 0.22 mmol) solution in 0.15 mL DMF was added dropwise. The reaction mixture was stirred at 0° C. for 2 h and additional 24 h at room temperature. Dicyclohexylurea (DCU) was removed by filtration, then DMF was removed in vacuo and the residue diluted with ethylacetate. Small amount of DCU was again removed by filtration and the filtrate was washed with aq. KHSO$_4$, NaHCO$_3$, NaCl and dried over MgSO$_4$. The dried solution was evaporated to almost dryness and the residue was triturated with ether to yield 120 mg of white powder.

The pure monomer was obtained by the purification on the preparative RP-HPLC column (VYDAC™C18, 22×250, 10 μm, flow rate 5 ml/min) employing a gradient from 75% to 85% B in 15 min followed by gradient from 85% to 88% in 20 min. Buffer A was 0.1% TFA in water and buffer B was 0.1% TFA in 90% MeOH. The product was eluted at 32 min. The purity of the monomer was evaluated by MALDI-TOF mass spectrometry (cal. M$^+$: 1249.4, found: 1272.64 M+Na) and the 2'-O-ester formation was validated by $^1$H NMR spectroscopy.

Example 4

Synthesis of 2'-O-methacryloylglycylphenylalanylleucylglycyl-paclitaxel (MA-GFLG-PTX) (Scheme 1)

Under nitrogen atmosphere, MA-GFLG-OH (129 mg, 0.28 mmol), paclitaxel (200 mg, 0.23 mmol) and DMAP (50 mg, 0.41 mmol) were dissolved in anhydrous DMF (1.0 mL). The solution was stirred for 15 min at 0° C., DCC (200 mg, 0.97 mmol) in DMF (1.0 mL) was added dropwise and the solution was stirred at 4° C. for 24 h. The reaction solvent was removed by rotary evaporation at reduced pressure. EtOAc (50 mL) was added, DCU was removed by filtration, and the solution was washed with KHSO$_4$ aq. (0.1 M), NaHCO$_3$ (1 M) and then NaCl aq, dried over MgSO$_4$. The solution was removed by rotary evaporation. The crude product was purified by column chromatography (silica gel 60 Å, 200-400 mesh, EtOAc: CH$_3$OH, 15:1) to white solid in 68% yield (206 mg, 1.5 mmol). The structure was confirmed by $^1$H NMR spectroscopy and matrix assisted laser desorption ionization

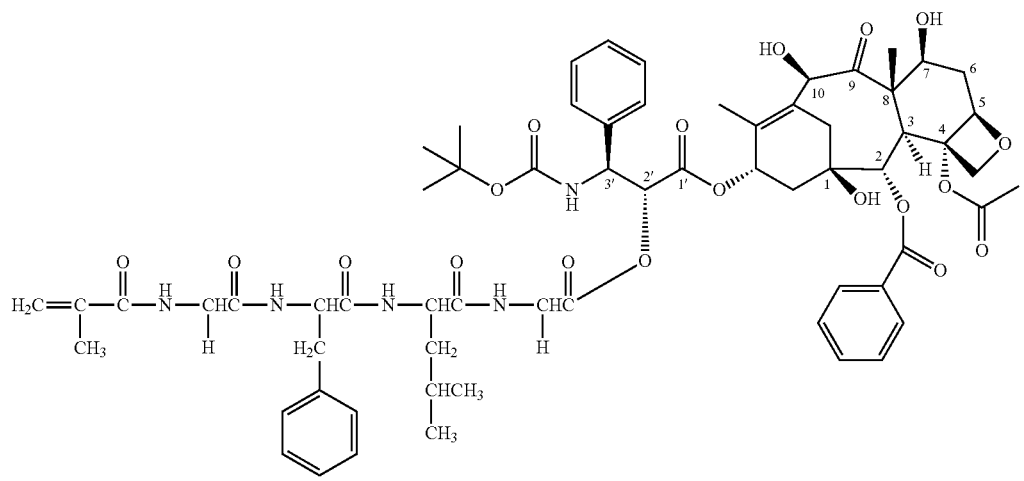

time-of-light (MALDI-TOF) mass spectrometry. MALDI-TOF MS: m/z 1318.68 ([M+Na]+).

Using the same approach polymerizable derivatives of paclitaxel (and other anticancer drugs, docetaxel, gemcitabine, epirubicin, etc) will be synthesized that contain different oligopeptide spacers, such as MA-GLLG-PTX; MA-AGVF-PTX; MA-Acap-Cit-F-PTX (Acap is $N^\varepsilon$-aminocaproic acid; Cit is citruline); MA-GFA-PTX; MA-GFGF-PTX. These (co)monomers will be used in the synthesis of targeted multiblock biodegradable HPMA copolymer-anticancer drug conjugates.

Examples of Synthesis of Components of the Initiating System

Example 5

Synthesis of 4,4'-azobis(N,N'-propargyl-4-cyanopentanamide) (Dialkyne-V-501) for Chain End Modification (Scheme 2)

Under a nitrogen atmosphere, 4,4'-azobis(4-cyanopentanoic acid) (CTP, 500 mg, 1.78 mmol), propargylamine (201.04 mg, 3.65 mmol) and HOBt (499.9 mg, 3.7 mmol) were dissolved in anhydrous DMF (15 mL). The solution was stirred for 5 min in ice bath, DIPEA (646 mg, 5.0 mmol) was added and then HBTU (1.4 g, 3.7 mmol) was added. The solution was stirred in ice bath for 30 min and at room temperature overnight. After reaction, EtOAc (100 mL) was added and the organic solution was washed with NaHCO$_3$ aq. (satd.) and HCl (1 M) then NaCl aq. The solution was dried (MgSO$_4$) and concentrated to 15 mL by rotary evaporation. The finally product was obtained by recrystallized with EtOAc and ether in 75% yield. $^1$H NMR (300 MHz, CDCl$_3$, δ in ppm): 1.44 (s, 3 H, CH$_3$), 1.72 (s, 3 H, CH$_3$), 2.21 (m, 2 H, CH), 2.23-2.44 (m, 8 H, CNCCH$_2$CH$_2$CO), 4.04 (m, 4, NHCH$_2$C), 6.14 (s, 1 H, NH), 6.19 (s, 1 H, NH). $^{13}$C NMR (75 MHz, CDCl$_3$, δ in ppm): 207.33, 207.28, 155.81, 155.66, 118.46, 110.61, 109.47, 109.40, 70.41, 67.31, 67.20, 65.45, 60.76, 60.45.

Example 6

Synthesis of 4,4'-azobis(azidopropyl 4-cyanopentanoate) (Diazido-V-501) for Chain End Modification (Scheme 3)

4,4'-Azobis(4-cyanovaleric acid) (V-501, 1 g, 3.6 mmol), 3-azidopropanol (1.08 g, 10.7 mmol) and DMAP (0.35 g, 2.9 mmol) were dissolved in DCM/THF (10/10 mL) and cooled to 4° C. DCC (1.62 g, 7.9 mmol) in 10 mL of DCM was added dropwise. After addition, the reaction mixture was stirred at 4° C. overnight, then room temperature 1 h. After completion of the reaction, 2 drops of acetic acid were added to the reaction mixture and stirring continued for 30 min. DCU was removed by filtration and the solvent was removed by rotary evaporation. The residue was purified by silica gel chromatography (silica gel 60 Å, 200-400 mesh, ethyl acetate/hexane 1/1). Yield 1.5 g. The structure was confirmed by $^1$H-NMR and $^{13}$C-NMR spectroscopy. $^1$H-NMR (CDCl$_3$, δ, ppm): 4.17 (m, 4H, —COOCH$_2$); 3.37 (m, 4H, N$_3$CH$_2$); 2.60-2.30 (m, 8H, CO—CH$_2$CH$_2$—C); 1.89 (m, 4H, C—CH$_2$—C); 1.68 (d, 6H, CH$_3$). $^{13}$C-NMR (CDCl$_3$, δ, ppm): 171.16; 117.42; 71.76; 62.01; 48.07; 33.05; 29.01; 27.97; 23.86.

Example 7

Synthesis of α,ω-dialkyne Chain Transfer Agent 2-cyano-5-oxo-5-(prop-2-ynylamino)pentan-2-yl 2-hex-5-ynamidoethyl Trithiocarbonate (CTA 1, Alkyne-TTC) (Scheme 4)

Under a nitrogen atmosphere, 5-hexynoic acid (1.0 g, 8.9 mmol), HBTU (3.41 g, 9.0 mmol) and HOBt (1.22 g, 9.0 mmol) were dissolved in anhydrous DMF (20 mL). The solution was stirred for 5 min in ice bath, DIPEA (1.94 g, 15 mmol) was added. The solution was stirred in ice bath for 5 min, then cysteamine (694.35 mg, 9.0 mmol) was added and the solution was stirred at room temperature overnight for 5 h. Then EtOAc (50 mL) was added and the organic solution was washed with NaHCO$_3$ aq. (satd.) and HCl (1 M) then NaCl aq. The solution was dried (MgSO$_4$) and removed to 15 mL by rotary evaporation. The Comp.1 was obtained by recrystallized from EtOAc in 78.5% yield. $^1$H NMR (300 MHz, CDCl$_3$, δ in ppm): 1.84 (m, 2 H, CCH$_2$CH$_2$CH$_2$CO), 1.95 (s, 2, CH), 2.22 (m, 2H, CCH$_2$CH$_2$CH$_2$CO), 2.34 (m, 2H, CCH$_2$CH$_2$CH$_2$CO), 2.82 (m, 2 H, SHCH$_2$CH$_2$), 3.55 (m, 2 H, SHCH$_2$CH$_2$), 6.46 (s, 1 H, NH). $^{13}$C NMR (75 MHz, CDCl$_3$, δ in ppm): 172.84, 83.48, 69.17, 38.40, 37.72, 34.88, 24.13, 17.87.

Compound 1 (513.8 mg, 3.0 mmol) was dissolved in water/acetone (3/1; 15 mL) and kept in ice bath and stirred for 5 min. KOH solution (50%; 202 mg, 3.6 mmol) was added dropwise to the stirred solution over 10 min, then carbon disulfide (228.4 mg, 3.0 mmol) was added in one portion, the system was stirred at room temperature for 30 min, and cooled to −5° C. by an ice/acetone bath. p-Toluenesulfonyl chloride (305 mg, 1.6 mmol) was added in portions over 10 min and stirring was continued at 24° C. for another hour. Then, the mixture was stirred at 45° C. for 10 min then dissolved in DCM (100 mL). After washing by NaCl aq. twice (2×50 mL), the organic layer was separated, dried over MgSO$_4$. Drying agent was removed by filtration, the solvent was removed by evaporation. The Compound 2 was obtained by recrystallization from DCM and ether in 63.1% yield. $^1$H NMR (300 MHz, CDCl$_3$, δ in ppm): 1.62 (t, 2 H, CCH$_2$CH$_2$CH$_2$CO), 2.12 (m, 4, CCH$_2$CH$_2$CH$_2$CO), 2.76 (s, 1 H, CH), 3.35 (m, 2 H, SCH$_2$CH$_2$), 3.44 (m, 2 H, SCH$_2$CH$_2$), 8.12 (s, 1 H, NH). $^{13}$C NMR (75 MHz, CDCl$_3$, δ in ppm): 221.25, 171.78, 84.01, 77.51, 38.88, 37.85, 36.11, 34.04, 24.15, 17.36.

Under nitrogen atmosphere, Compound 2 (200 mg, 0.435 mmol) and di-alkyne V501 (Example 4, 231.28 mg, 0.653 mmol) was added with distilled ethyl acetate (15 mL). The solution was reflux for 20 h. Then ethyl acetate was removed under reduced pressure. The crude product was isolated by column chromatography (silicagel 60 Å, 60-200 mesh) using ethyl acetate:hexane (50:50) as eluent. The target compound was obtained as yellow oil, yield: 51%. $^1$H NMR (300 MHz, CDCl$_3$, δ in ppm): 1.78 (m, 2 H, CCH$_2$CH$_2$CH$_2$CO), 1.82 (s, 3 H, CH$_3$), 1.96 (s, 1 H, CH), 2.12 (s, 1 H, CH), 2.19 (m, 4, CCH$_2$CH$_2$CH$_2$CO), 2.29 (m, 2 H, CNCCH$_2$CH$_2$), 2.44 (m, 2 H, CNCCH$_2$CH$_2$), 3.48 (m, 4 H, SCH$_2$CH$_2$), 6.63 (s, 1 H, NH), 7.18 (s, 1 H, NH). $^{13}$C NMR (75 MHz, CDCl$_3$, δ in ppm): 217.27, 173.32, 170.69, 119.35, 83.72, 79.67, 71.81, 69.66, 47.16, 37.82, 36.34, 35.15, 34.31, 31.40, 29.43, 25.04, 24.40, 18.13. Mass spectrum (ESI) calcd: 410.1 m/z (M+H+), observed: 410.2 m/z (M+H+). Mass spectrum (MALDI) calcd: 410.10 m/z (M+H+), observed: 410.05 m/z (M+H+).

Example 8

Synthesis of Alkyne-Functionalized, Enzyme-Sensitive CTA, $N^\alpha$-(5-pentanoyl)-$N^\epsilon$-(4-cyano-4-(phenylcarbonothioylthio)pentanoyl-glycylphenylalanylleucylglycyl)-lysine (CTP-GFLG-alkyne; CTA 2) (Scheme 5)

CTP-GFLG-alkyne was synthesized using solid phase peptide synthesis (SPPS) methodology. Dde-Lys(Fmoc)-OH (351 mg, 0.64 mmol) was dissolved in 5 mL DCM with 282 µL DIPEA, then added to the vial containing 1 g 2-chlorotrityl chloride resin (1.29 mmol/g). The vial was kept gently shaking for 1.5 h. The resin was transferred to a polypropylene tube, rinsed with mixture of DCM:MeOH:DIPEA (17:2:1) (20 mL×4). The resin was then washed three times with DCM and DMF, respectively. Fmoc-group was removed with 10 mL 20% piperidine in DMF (5 min×3). Hexynoic acid (2.5×, 1.6 mmol) was coupled in the presence of HBTU (2.4×, 586 mg) and DIPEA (5×, 3.2 mmol, 570 µL) to introduce alkyne group. After removal of Dde group with 10 mL 3% hydrazine in DMF (5 min×3), the elongation by tetrapeptide GFLG was accomplished by sequentially coupling with Fmoc-Gly-OH, Fmoc-Leu-OH, Fmoc-Phe-OH and Fmoc-Gly-OH using the HBTU/DIPEA procedure. Ninhydrin test (also known as Kaiser test) was used to confirm the completion of each coupling and deprotection step. The N-terminal of the peptide was capped with 4-cyanopentanoic acid dithiobenzoate (1.6 mmol, 0.45 g) in the presence of DIC/HOBt. The beads were dealt with the mixture TFE/DCM (3:7) for 2 h. The resin was removed by filtration. The filtrate was condensed under reduced pressure, purified by precipitation of the solution in methanol into ether. Pink powder was obtained. The structure was verified by MALDI-ToF-mass spectrum ([M+H$^+$] 876.41). The purity was determined by RP-HPLC.

Following the same principle, enzyme-sensitive CTA with different sequences (CTA 2a and CTA 2b) can be synthesized using Fmoc-Orn(ivDde)-OH as the 1$^{st}$ amino acid.

Example 9

Synthesis of 3-azidopropyl 4-cyano-4-thiobenzoylsulfanyl-pentanoate (CTP-N$_3$, CTA 3)

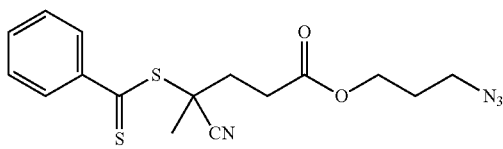 [SMILES: CC(C#N)(CCC(=O)OCCCN=[N+]=[N-])SC(=S)c1ccccc1]

4-cyano-4-thiobenzoylsulfanyl-pentanoic acid (CTP, 1.0 g, 3.6 mmol) and DMAP (439.8 mg, 3.6 mmol) were dissolved in anhydrous DCM (50 mL). The solution was stirred for 5 min in ice bath, and EDCI (690.1 mg, 3.6 mmol) was added and stirred for 30 min. 3-Azidopropanol (364 mg, 3.6 mmol) was added and the solution was stirred in ice bath for 30 min and at room temperature for another 8 h. After reaction, the solution was washed with NaHCO$_3$ aq. (satd.) and then H$_2$O. The organic layer was dried (Na$_2$SO$_4$), solvent removed by rotary evaporation and the crude product was purified by column chromatography (silicagel 60 Å, 200-400 mesh, ethyl acetate:hexane, 1:4) to give rose-red oil in 84.6% yield. The structure of this compound was confirmed by $^1$H NMR and $^{13}$C NMR spectroscopy. $^1$H NMR (300 MHz, CDCl$_3$, δ in ppm): 1.90-1.93 (m, 5 H, —CH$_2$CH$_2$N$_3$, —CH$_3$), 2.45-2.60 (m, 2 H, C(CN)CH$_2$—), 2.68 (m, 2 H, C(CN)CH$_2$CH$_2$—), 3.40 (t, 2 H, —CH$_2$N$_3$), 4.21 (t, 4 H, —OCH$_2$CH$_2$—), 7.39 (m, 2 H, PH-2H), 7.57 (m, 1 H, PH-4H), 7.89 (m, 2 H, PH-3H). $^{13}$C NMR (75 MHz, CDCl$_3$, δ in ppm): 222.40, 171.43, 144.74, 133.29, 128.82, 126.91, 118.68, 62.22, 48.34, 45.93, 33.60, 29.98, 28.27, 24.41.

Example 10

Synthesis of Enzyme-Sensitive, CTA, $N^\alpha$-(azidophenyl)-$N^\epsilon$-(4-cyano-4-(phenylcarbonothioylthio)pentanoyl-glycylphenylalanylleucylglycyl)-lysine (CTP-GFLGK-N$_3$; CTA 4) (Scheme 6)

The telechelic-chain transfer agent containing an enzyme-sensitive peptide was synthesized by SPPS methodology and manual Fmoc/tBu strategy on 2-chlorotrityl chloride resin. Fmoc-Lys(Dde)-OH was loaded to the beads (0.5 g, 0.19 mmol loading) as the first amino acid. Azido benzoic acid was coupled to α-NH$_2$ of lysine after removal of Fmoc group by 20% pepridine in DMF. Then ε-Dde group was removed by 3% hydrazine in DMF. Fmoc-Gly-OH, Fmoc-Leu-OH, Fmoc-Phe-OH and Fmoc-Gly-OH were coupled successively to the beads by using HBTU as the coupling agent and 20% pepridine in DMF as the deprotection agent. After deprotection, chain transfer agent, 4-cyanopentanoic acid dithiobenzoate, was coupled to the amino group of glycine using DIC as the coupling agent. The peptide was isolated following cleavage from 2-Cl-trityl resin by 30% TFE in DCM for 2 h. Yield 85 mg of the product. The peptide was characterized by $^1$H-NMR spectroscopy. $^1$H-NMR (DMSO-d6, δ, ppm): 12.62 (s, 1H, —COOH); 8.45 (t, 1H, Ph-CONH); 8.28 (q, 1H, CONH); 8.10 (m, 2H, CONH); 8.02 (m, 1H, CONH); 7.97 (d, 1H, CONH); 7.88 (m, 4H, Ph-H); 7.68 (t, 1H, Ph-H); 7.50 (t, 2H, Ph-H); 7.21 (m, 7H, Ph-H); 4.51 (m, 1H, Phe-CH); 4.25 (m, 1H, Leu-CH); 4.17 (m, 1H, Lys-CH); 3.71-3.56 (m, 4H, Gly-CH$_2$); 3.21 (m, 2H, Lys-NH—CH$_2$); 3.03 (m, 1H, Phe-CHH); 2.76 (m, 1H, Phe-CHH); 2.50-2.35 (m, 4H, CTA-CH$_2$CH$_2$); 1.88 (s, 3H, CTA-CH$_3$); 1.73-1.30 (m, 9H, Lys-C—CH$_2$CH$_2$CH$_2$—C, Leu-CH$_2$CHMe$_2$); 0.88-0.81 (dd, 6H, Leu-Me).

Example 11

Synthesis of Two-Arm CTA, $N^\alpha$,$N^\delta$-(bis(4-cyano-4-(phenylcarbonothioylthio)pentanoylglycylphenylalanylleucylglycyl)lysine ((CTP-GFLG)$_2$K; CTA 5) (Scheme 7)

The telechelic-chain transfer agent containing an enzyme-sensitive peptide was synthesized by SPPS methodology and manual Fmoc/tBu strategy on 2-chlorotrityl chloride resin. Fmoc-Lys(Dde)-OH was loaded to the beads (0.5 g, 0.19 mmol loading) as the first amino acid. Azido benzoic acid was coupled to α-NH$_2$ of lysine after removal of Fmoc group by 20% piperidine in DMF. Then ε-Dde group was removed by 3% hydrazine in DMF. Fmoc-Gly-OH, Fmoc-Leu-OH, Fmoc-Phe-OH and Fmoc-Gly-OH were coupled successively to the beads by using HBTU as the coupling agent and 20% piperidine in DMF as the deprotection agent. After deprotection, chain transfer agent, 4-cyanopentanoic acid dithiobenzoate, was coupled to the amino group of glycine using DIC as the coupling agent. The peptide was isolated following cleavage from 2-Cl-trityl resin by 30% TFE in DCM for 2 h. Yield 85 mg of the product. The peptide was characterized by $^1$H-NMR spectroscopy. $^1$H NMR (DMSO-d6, δ, ppm): 12.62 (s, 1H, —COOH); 8.45 (t, 1H, Ph-CONH); 8.28 (q, 1H, CONH); 8.10 (m, 2H, CONH); 8.02 (m, 1H, CONH); 7.97 (d, 1H, CONH); 7.88 (m, 4H, Ph-H); 7.68 (t, 1H, Ph-H); 7.50 (t, 2H, Ph-H); 7.21 (m, 7H, Ph-H); 4.51 (m, 1H, Phe-CH); 4.25 (m, 1H, Leu-CH); 4.17 (m, 1H, Lys-CH); 3.71-3.56 (m, 4H, Gly-CH$_2$); 3.21 (m, 2H, Lys-NH—CH$_2$); 3.03 (m, 1H, Phe-CHH); 2.76 (m, 1H, Phe-CHH); 2.50-2.35 (m, 4H, CTA-CH$_2$CH$_2$); 1.88 (s, 3H, CTA-CH$_3$); 1.73-1.30 (m, 9H, Lys-C—CH$_2$CH$_2$CH$_2$—C, Leu-CH$_2$CHMe$_2$); 0.88-0.81 (dd, 6H, Leu-Me).

Example 12

Synthesis of Dialkyne Compounds for Chain Extension

SPPS Synthesis of Enzyme-Degradable Peptides with Dialkyne Modification, HC≡C-GFLG-C≡CH (a) and HC≡C-QSFRFK-C≡CH (b) (Scheme 8)

Fmoc-Lys(ivDde)-OH was employed as the first amino acid residue to introduce two free amine groups. The protecting groups (Fmoc- and ivDde-) were removed selectively; one was used to introduce alkyne group into the C-terminus of the peptide, whereas the other functioned in constructing the peptide sequence. Incorporation of alkyne at the N-terminus was accomplished by acylation of the peptide with 5-hexynoic acid using the standard coupling protocol (—COOH/DIPEA/HATU in DMF). The resin was then washed sequentially with 3×DMF, 3×DCM and 3×MeOH, and dried under vacuum. The resulting resin-bound peptides were cleaved from the resin, and side-chains were deprotected using TFA:H$_2$O:TIS (95:2.5:2.5) cocktail. Crude peptides were purified by RP-HPLC (Agilent Technologies 1100, semipreparative Zorbax 300SB-C18 column, 250×9.4 mm, 300 Å pore size, 5 μm particle size, flow rate 2.5 mL/min) employing a gradient from 50% to 100% B over 30 min, where Buffer A was 0.1% TFA in water and Buffer B 0.1% TFA in 90:10 (v/v) methanol/water. The purity of the product was verified by analytical RP-HPLC. The structure was ascertained by MALDI-TOF mass spectrometry (Voyager-DE STR Biospectrometry Workstation, Perseptive Biosystems).

Following above protocol, two enzyme-degradable peptides with dialkyne modification, HC≡C-GFLG-C≡CH (a) and HC≡C-QSFRFK-C≡CH (b), were synthesized. The structure of these peptides was confirmed by MALDI-TOF mass spectra: for dialkyne-GFLG, cal. 708.38 (M$^+$), found 709.41 (M+H)$^+$; for dialkyne-QSFRFK, cal. 998.53 (M$^+$), found 999.55 (M+H)$^+$.

Solution Phase Organic Synthesis of HC≡C-GFLG-C≡CH

Fmoc-L-Lys(Boc)-OH (5.0 g, 10.3 mmol) was dissolved in CH$_3$OH (50 mL). The solution was stirred for 5 min at −15° C., then SOCl$_2$ (1.4 g, 12 mmol) was added dropwise. The solution was stirred at 0° C. for 30 min and at 60° C. for another 3 h. After work-up, 200 mL ether was added and compound 2 was obtained by crystallization in 96.7% yield.

Under nitrogen atmosphere, Fmoc-L-Lys-OMe.HCl (2.4 g, 5.7 mmol), 5-hexynoic acid (616.6 mg, 5.5 mmol) and HOBt (810.6 mg, 6 mmol) were dissolved in EtOAc (50 mL). The solution was stirred for 5 min in ice bath, then DIPEA (1.9 g, 15 mmol) followed by EDCI (1.15 g, 6 mmol) were added. The solution was stirred in ice bath for 30 min and at room temperature for 16 h. After reaction, EtOAc (200 mL) was added and the solution was washed with NaHCO$_3$ aq. (satd.), HCl (1 M), and NaCl aq. The EtOAc solution was dried (MgSO$_4$) and solvent partially removed (to 50 mL) by rotary evaporation. Compound 3 was obtained by recrystallization in 84% yield. (Scheme 9)

Gly-Phe-OH (5.0 g, 22.5 mmol) was dissolved in CH$_3$OH (50 mL). The solution was stirred for 5 min at −15° C., then SOCl$_2$ (3.0 g, 25 mmol) was added dropwise. The solution was stirred at 0° C. for 30 min and at 64° C. for another 3 h. After reaction, 200 mL ether was added and Compound 5 was obtained by recrystallization in EtOAc with 94.1% yield.

Gly-Phe-OMe.HCl (5.0 g, 18.3 mmol), 5-hexynoic acid (2.0 g, 18 mmol) and HOBt (2.7 g, 20 mmol) were dissolved in anhydrous DMF (100 mL) under nitrogen atmosphere. The solution was stirred for 5 min in ice bath, then DIPEA (6.5 g, 50 mmol) following by HBTU (7.6 g, 20 mmol) were added. The solution was stirred in ice bath for 30 min and at room temperature overnight. After reaction, EtOAc (300 mL) was added and the solution was washed with NaHCO$_3$ aq. (satd.), HCl (1 M) and NaCl aq. The solution was dried (MgSO$_4$) and volume reduced to 50 mL by rotary evaporation. Compound 6 was obtained by recrystallization from EtOAc and ether in 86.3% yield.

Compound 6 (4.5 g, 13.6 mmol) was dissolved in CH$_3$OH (100 mL). The solution was stirred for 5 min in ice bath, NaOH (1 M, 15 mmol) in CH$_3$OH (25 mL) was added dropwise over 30 min. The solution was stirred in ice bath for 1.5 h and at room temperature for another 1 h. After reaction, the MeOH was removed, EtOAc (200 mL) added and the solution was acidified to pH=2~3 with HCl (1 M), separated, the aq. was extracted with EtOAc (50×3). The organic solution was dried (MgSO$_4$) and volume reduced to 50 mL by rotary evaporation. Compound 7 was obtained by recrystallization from EtOAc and ether in 90.6% yield.

Compound 7 (3.5 g, 11.1 mmol), Leu-Gly-OMe.HCl (2.74 g, 11.5 mmol) and HOBt (1.62 g, 12 mmol) were dissolved in anhydrous DMF (100 mL). The solution was stirred for 5 min in ice bath, and then DIPEA (3.6 g, 28 mmol) followed by HBTU (4.6 g, 12 mmol) were added. The solution was stirred in ice bath for 30 min and at room temperature overnight. After reaction, EtOAc (250 mL) was added and the organic solution was washed with NaHCO$_3$ aq. (satd.) and HCl (1 M) then NaCl aq. The solution was dried (Na$_2$SO$_4$) and reduced to 50 mL by rotary evaporation. Compound 8 was obtained by recrystallization in EtOAc with 85% yield.

Compound 9 was obtained from Compound 8 by hydrolysis with NaOH. Yield=87.9%.

Under nitrogen atmosphere, Compound 3 (1.43 g, 3.0 mmol) was stirred in 20% piperidine in DMF, the solvents was removed and treated with ether to give the oil. The oil, Compound 9 (1.46 g, 3.0 mmol) and HOBt (418.8 mg, 3.1 mmol) were dissolved in anhydrous DMF (50 mL). The solution was stirred for 5 min in ice bath, DIPEA (646 mg, 5 mmol) was added and then HBTU (1.18 g, 3.1 mmol) was added. The solution was stirred in ice bath for 30 min and at room temperature overnight. After reaction, EtOAc (150 mL) was added and the organic solution was washed with NaHCO$_3$ aq. (satd.) and HCl (1 M) then NaCl aq. The solution was dried (MgSO$_4$) and removed to 50 mL by rotary evaporation. Compound 10 was obtained by recrystallization with 81% yield.

Compound 11 was obtained from Compound 10 by hydrolysis with NaOH. Yield 89%. The structure was characterized by MALDI-TOF mass spectrometry. MALDI-TOF MS: m/z 731.31 [(M+Na)$^+$].

Example 13

Synthesis of Diazido Compound for Chain Extension, $N^\alpha,N^\varepsilon$-(bis(azidobenzoylglycylphenylalanylleucylglycylalanyl)lysine ($N_3$-GFLG-$N_3$) (Scheme 10)

The telechelic, azido-group functionalized enzyme-sensitive peptides were synthesized by SPPS methodology and manual Fmoc/tBu strategy on 2-chlorotrityl chloride resin. Fmoc protected amino acids, Fmoc-Lys(Fmoc)-OH, Fmoc-Ala-OH, Fmoc-Gly-OH, Fmoc-Leu-OH, Fmoc-Phe-OH and Fmoc-Gly-OH were coupled successively to the beads (0.4 g, 0.15 mmol loading) by using HBTU as the coupling agent and 20% piperidine in DMF as the deprotection agent. After deprotection, azidobenzoic acid was coupled to the glycyl residues using DIC as the coupling agent. The peptide was isolated following cleavage from 2-Cl-trityl resin by 30% TFE in DCM for 2 h. Yield 128 mg (65%). The peptide was characterized by $^1$H-NMR spectroscopy. $^1$H-NMR (DMSO-d6, δ, ppm): 12.53 (s, 1H, —COOH); 8.76 (t, 2H, Ph-CONH); 8.17-7.82 (m, 14H, CONH, Ph-H); 7.19 (m, 14H, Ph-H); 4.53 (m, 2H, Phe-CH); 4.34-4.17 (m, 4H, Leu-CH, Ala-CH); 4.16 (m, 1H, Lys-CH); 3.90-3.62 (m, 8H, Gly-$CH_2$); 3.00 (m, 4H, Phe-CHH, Lys-NH—$CH_2$); 2.79 (m, 2H, Phe-CHH); 1.68-1.26 (m, 12H, Lys-C—$CH_2CH_2CH_2$—C, Leu-$CH_2CHMe_2$); 1.62 (t, 6H, Ala-$CH_3$); 0.87-0.81 (dd, 12H, Leu-Me).

Example 14

Synthesis of $N^\alpha$, $N^\varepsilon$-bis(4-maleimidomethyl-cyclohexanecarbonyl-glycylphenylalanlylleucylglycyl)lysine (($MAL$-$GFLG)_2K$) (Scheme 11)

The telechelic, maleimido-group functionalized enzyme-sensitive peptide was synthesized by SPPS methodology and manual Fmoc/tBu strategy on 2-chlorotrityl chloride resin. Fmoc protected amino acids, Fmoc-Lys(Fmoc)-OH, Fmoc-Gly-OH, Fmoc-Leu-OH, Fmoc-Phe-OH and Fmoc-Gly-OH were coupled successively to the beads (0.1 g, 0.04 mmol loading) using HBTU as the coupling agent and 20% piperidine in DMF as the deprotection agent. After deprotection, the heterobifunctional agent, SMCC (succinimidyl-4-(N-maleimidomethyl)cyclohexane-1-carboxylate) was coupled to the glycyl residues. The product was isolated following cleavage from 2-Cl-trityl resin by 30% TFE in DCM for 2 h. Yield 38 mg (76%). The peptide was characterized by $^1$H-NMR spectroscopy. $^1$H-NMR (DMSO-d6, δ, ppm): 12.62 (s, 1H, —COOH); 8.14-7.15 (m, 20H, CONH, Ph-H); 7.00 (s, 4H, —CH═CH—); 4.48 (m, 2H, Phe-CH); 4.25 (m, 2H, Leu-CH); 4.16 (m, 1H, Lys-CH); 3.74-3.50 (m, 8H, Gly-$CH_2$); 3.22 (d, 4H, $CH_2$-cyclohexane); 3.01 (m, 4H, Phe-CHH, Lys-NH—$CH_2$); 2.77 (m, 2H, Phe-CHH); 2.08 (m, 4H, 4CH in cyclohexane); 1.68-1.15 (m, 28H, Lys-C—$CH_2CH_2CH_2$—C, Leu-$CH_2CHMe_2$, 8 $CH_2$ in cyclohexane); 0.87-0.80 (dd, 12H, Leu-Me).

Examples of the Synthesis of Backbone Degradable HPMA Copolymer—Drug Conjugates Using the Alkene-Azide Reactions

Example 15

Synthesis of Alkyne-Telechelic polyHPMA (HC≡C-PolyHPMA-C≡CH) via HPMA RAFT Polymerization (Scheme 12)

RAFT Polymerization of HPMA with Dialkyne-Functionalized CTA (CTA 1). An ampoule containing HPMA (0.1 g, 0.7 mmol) and CTA 1 (2.88 mg, 0.007 mmol) was attached to a Schlenk line. After three vacuum-nitrogen cycles to remove oxygen, 0.5 mL degassed distilled water was added followed by addition of initiator V-501 solution in distilled water (0.4 mg in 0.1 mL) via syringe. The ampoule was sealed and polymerization was performed at 70° C. for 12 h. The polymer was obtained by precipitation into acetone and purified by re-dissolving in methanol-precipitation in acetone two more times. The telechelic polyHPMA was dried under vacuum. Yield 95 mg. The polymer was analyzed by size-exclusion chromatography (SEC) on an AKTA FPLC system (Pharmacia) equipped with miniDAWN TREOS and OptilabEX detectors (Wyatt Technology, Santa Barbara, Calif.) using a Superose6 HR/10/30 column with PBS (pH 7) as mobile phase. The average molecular weight of the polymer was determined by light scattering, UV, RI and calculated by ASTRA software (Mw 14 kDa, PDI 1.02).

Example 16

Synthesis of Biodegradable Multiblock polyHPMA Via Click Reaction (Scheme 13)

Biodegradable multiblock polyHPMA was synthesized via click reaction. Alkyne-telechelic polyHPMA (50 mg, Mw 14 kDa, Mw/Mn 1.03) and azido-terminated peptide were dissolved in 200 μL of degassed solution of L-ascorbic acid (0.5×, 0.6 mg) in DMF. Under nitrogen atmosphere, 50 μL CuBr (1×, 1 mg) solution in DMF was added. The reaction mixture kept stirring at rt for 48 h. The polymer was precipitated into acetone and purified by dialysis against 10 mM EDTA solution and then in water to remove copper salts and then freeze-dried. Yield 42 mg of click product. After fractionation by S6 preparative column, the polymer with Mw 352 kDa, Mw/Mn 1.2 was obtained.

Example 17

Figure 2:
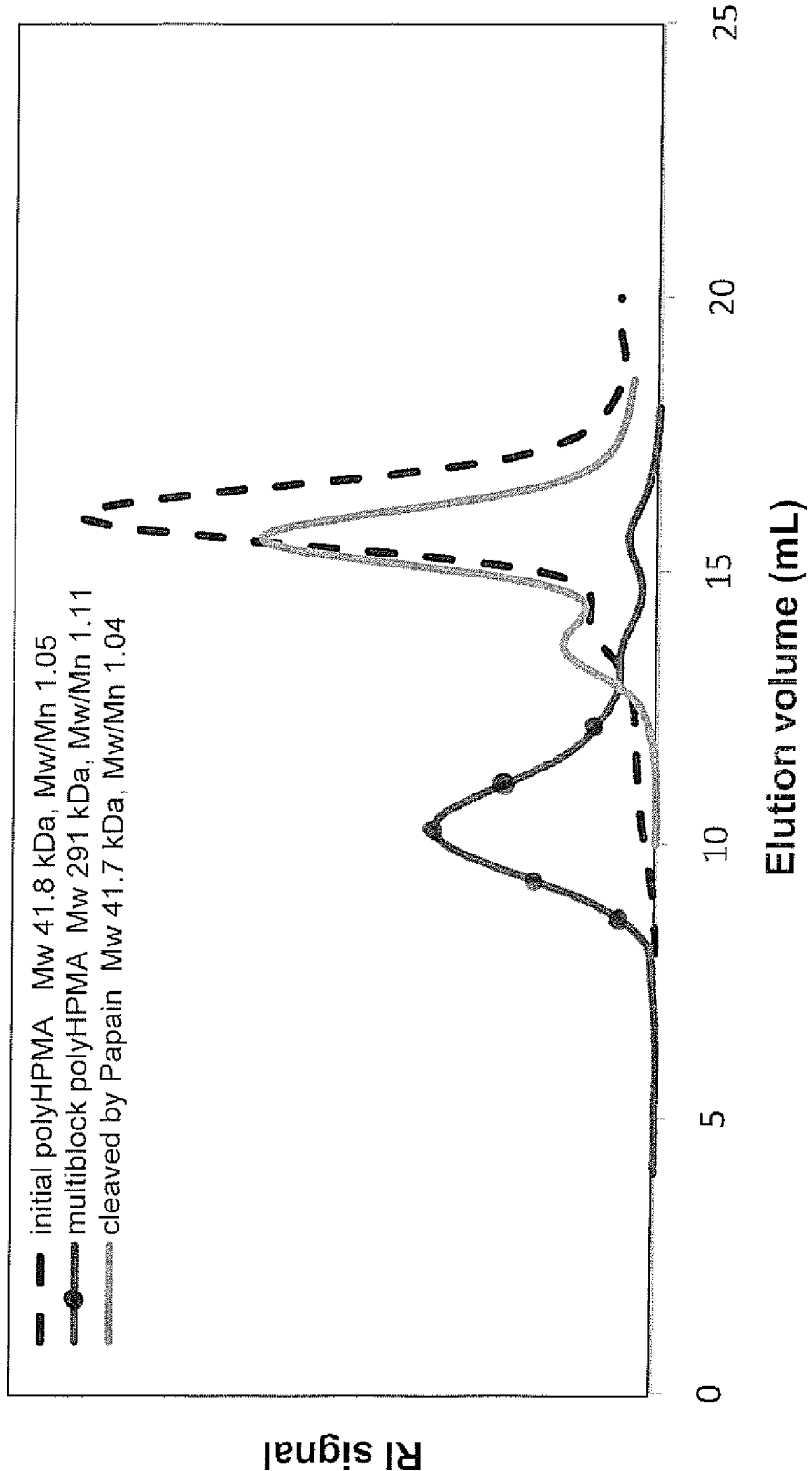
FIG. 2 shows chain extension of heterotelechelic polyHPMA (Mw=41.8 kDa, Mw/Mn=1.05) by copper catalyzed alkyne and azide 1,3-dipolar cycloaddition into a multi block copolymer. Incubation of the multiblock copolymer (selected fraction; Mw=291 kDa, Mw/Mn=1.11) with 0.14 mg/mL papain in citrate-phosphate buffer (pH 6.0) at 37° C. resulted in total degradation of the oligopeptide sequences in multiblock copolymer backbone and formation of the polymer with initial molecular weight (Mw=41.7 kDa, Mw/Mn=1.04).

Enzyme-Catalyzed Degradation of Multiblock polyHPMA Prepared from Heterotelechelic Precursor The degradation of multiblock polyHPMA containing GFLG sequences in the polymer backbone was performed in McIlvaine's buffer (50 mM citrate/0.1 M phosphate) at pH 6.0, 37° C. using papain as model enzyme. Papain, at concentration of 0.05 mg/mL (determined by UV at 280 nm), was reduced with 5 mM glutathione for 5 min. The enzyme activity was confirmed using Bz-PheValArg-NAp as chromogenic substrate. The polymer (3-10 mg) was dissolved in the enzyme solution (3 mg/mL) and kept at 37° C. At predetermined time points the medium was analyzed with size-exclusion chromatography on an AKTA FPLC system (Pharmacia) equipped with miniDAWN TREOS and OptilabEX detectors (Wyatt Technology, Santa Barbara, Calif.) using a Superose 6 HR/10/30 column with PBS (pH 7) as mobile phase. Incubation of the multiblock copolymer (selected fraction; Mw=291 kDa, Mw/Mn=1.11) with 0.14 mg/mL papain in citrate-phosphate buffer (pH 6.0) at 37° C. resulted in total degradation of the oligopeptide sequences in multiblock copolymer backbone and formation of the polymer with initial molecular weight (Mw=41.7 kDa, Mw/Mn=1.04) (FIG. 2).

Example 18

Synthesis of Heterotelechelic polyHPMA ($N_3$-PolyHPMA-C≡CH) (Scheme 14)

RAFT Polymerization of HPMA. An ampoule containing HPMA (0.5 g, 3.5 mmol) and CTP-GFLGK-alkyne (CTA 2, 17 mg, 0.019 mmol) was attached to the Schlenk line. After three vacuum-nitrogen cycles to remove oxygen in the ampoule, 2.5 mL degassed water was added followed by addition of initiator AIBN solution in methanol (1.78 mg in 0.1 mL) via syringe. The ampoule was sealed and polymerization was performed at 65° C. for 20 h. The polymer was obtained by precipitation into acetone and purified by re-dissolving in methanol-precipitation in acetone two more times. The polymer (polyHPMA) was dried under vacuum and isolated as a pink powder. Yield 0.42 g. The polymer was analyzed by size-exclusion chromatography (SEC) on an AKTA FPLC system (Pharmacia) equipped with miniDAWN TREOS and OptilabEX detectors (Wyatt Technology, Santa Barbara, Calif.) using a Superose6 HR/10/30 column with PBS (pH 7) as mobile phase. The average molecular weight of the polymer was determined by light scattering, UV, RI and calculated by ASTRA software (Mw 33.1 kDa, PDI 1.04).

End Group-Modification. Heterotelechelic HPMA polymer (Mw=33.1 kDa, 100 mg) containing alkyne and dithiobenzoate chain ends was dissolved in 500 µL of 1-methyl-2-pyrrolidinone (NMP). To convert the dithiobenzoate group into an azide group, diazido-V-501 (20×, 0.06 mmol) was added, the solution was bubbled with $N_2$ for 30 min, sealed and kept stirring at 70° C. for 3 h. The polymer was purified by precipitation into acetone and dried under reduced pressure. Yield 96 mg of α-azido-ω-alkyne-polyHPMA ($N_3$-PolyHPMA-C≡CH). The completion of end group-modification was confirmed by $^1$H-NMR spectroscopy showing no detectable dithiobenzoate group (δ=7-8.5 ppm) and by FTIR showing a new peak at 2100 cm$^{-1}$ (azide).

Example 19

Synthesis of Biodegradable Multiblock polyHPMA by Click Reaction (Scheme 15)

Chain Extension Via Microwave-Assisted Click Reaction. Heterotelechelic $N_3$-PolyHPMA-C≡CH (20 mg) was dissolved in 100 µL of degassed L-ascorbic acid (0.25×, 0.026 mg) solution in DMF. Under nitrogen atmosphere, 100 µL CuBr (0.5×, 0.044 mg) solution in DMF was added. The reaction mixture was placed in the microwave reactor (Biotage) at 36 W for 30 min. The polymer was precipitated into acetone and purified by dialysis against 10 mM EDTA solution to remove copper salts and then dried. Yield 16 mg of click product. The polymer was analyzed by SEC. The results indicated triple peaks related to tetramers (Mw 121.1 kDa) and dimers (Mw 69.6 kDa) in addition to remained monomer (33.7 kDa). The individual mers will be separated on a chromatography column resulting in fractions of narrow molecular weight distribution.

Example 20

Synthesis of Telechelic HPMA Copolymer Containing Pendant Amino Groups (P—NH$_2$) (Scheme 16)

HPMA copolymer containing side-chain amino group (P—NH$_2$) was produced by copolymerization of HPMA with N-(3-aminopropyl)methacrylamide hydrochloride (APMA). An ampoule containing HPMA (88 mg), APMA (12 mg, 10 mol %), CTP-GFLGK-alkyne (CTA 2, 3.8 mg) was attached to a Schlenk line. After three vacuum-nitrogen cycles to remove oxygen, 0.5 mL degassed H$_2$O were added, followed by addition of initiator V-501 solution in methanol (0.36 mg in 50 µL) via syringe. The ampoule was sealed and copolymerization was performed at 70° C. for 20 h. The polymer was obtained by precipitation into acetone and purified by re-dissolving in methanol-precipitation in acetone two more times. The copolymer (P—NH$_2$) was end-modified according to the procedure described in Example 18. The polymer was analyzed with SEC on an AKTA FPLC system (Pharmacia) equipped with miniDAWN TREOS and OptilabEX detectors (Wyatt Technology, Santa Barbara, Calif.) using a Superose 6 HR/10/30 column with PBS (pH 7) as mobile phase. The average molecular weight of the polymer was determined by light scattering, UV, RI and calculated by ASTRA software. The content of amino group was determined by ninhydrin assay. The chain extension will be done following the similar procedure in Example 19.

Example 21

Synthesis of Telechelic HPMA Copolymer Containing Targeting Moiety Fab'

Telechelic HPMA copolymer containing pendant amino groups (P—NH$_2$) was first synthesized as described in Example 20. Amino groups were quantitatively converted to maleimido groups for conjugation with Fab' by reaction with SMCC in DMF in the presence of triethylamine. The amount of maleimide in the copolymer was determined using modified Ellman's assay. Then Fab' fragment (from the OV-TL16 antibody) will be bound to the carrier: The targeted conjugate will be prepared by dissolving the polymer precursor in 20 mM MES buffer pH 6.5 and reacting with freshly prepared Fab' fragment (polymer:Fab' weight ratio=1:2) overnight in dark at 4° C. The product will be purified on a DEAE Sepharose Fast Flow ion exchange column (Pharmacia), eluted using 20 mM Bis-Tris buffer pH 6.5 with a gradient NaCl concentration of 0-0.5 M. The fraction corresponding to conjugate will be isolated by SEC using Superose 6 (HR 10/30) column. After conjugation of the Fab' fragment to the polymer precursor, the heterotelechelic HPMA copolymer containing targeting moiety (Fab') can be extended either with identical building block or with another heterotelechelic HPMA copolymer containing anti-cancer drugs to produce targeted biodegradable multiblock HPMA copolymer-based polymer therapeutics.

Example 22

Synthesis of Telechelic HPMA Copolymer Containing Thiazolidine-2-thione (TT) Reactive Groups (P-TT) (Scheme 17)

HPMA copolymer containing side-chain reactive group was produced by copolymerization of HPMA with a polymerizable derivative of thiazolidine-2-thione (TT). An ampoule containing HPMA (0.3 g), MA-GFLG-TT (60 mg, 5 mol %), CTP-GFLGK-alkyne (CTA 2, 12.5 mg) was attached to the Schlenk line. After three vacuum-nitrogen cycles to remove oxygen, 2 mL degassed MeOH were added, followed by addition of initiator AIBN solution in methanol (0.6 mg in 0.1 mL) via syringe. The ampoule was sealed and copolymerization was performed at 65° C. for 24 h. The polymer was obtained by precipitation into acetone and purified by re-dissolving in methanol-precipitation in acetone two more times. The copolymer (P-TT) was end-modified according to the procedure described in Example 18. The polymer was analyzed with SEC on an AKTA FPLC system (Pharmacia) equipped with miniDAWN TREOS and OptilabEX detectors (Wyatt Technology, Santa Barbara, Calif.) using a Superose 6

HR/10/30 column with PBS (pH 7) as mobile phase. The average molecular weight of the polymer was determined by light scattering, UV, RI and calculated by ASTRA software (Mw=16 kDa, PDI=1.02). The content of TT in the copolymer was 5.3%, determined by UV spectrophotometry in methanol ($\epsilon_{305}$=10,800 Lmol$^{-1}$ cm$^{-1}$).

This polymer precursor can be used for consecutive binding of anticancer drug(s), and targeting moieties.

Conjugate 22a: Following dissolution of the polymer precursor in DMSO, doxorubicin and galactosamine will be bound to the polymer via amide bonds, the product purified by SEC. The chain extension of the product as described in Example 19 will provide a multiblock biodegradable HPMA copolymer-DOX conjugate targetable to hepatocytes via the biorecognition of N-acylated galactosamine by the asialoglycoprotein receptor.

Conjugate 22b: Following dissolution of the polymer precursor in DMSO, epirubicin and the 5'-aminohexyl-anti-PSMA aptamer A9 (see structure at Bioconjugate Chemistry 19, 1309, 2008) will be bound to the polymer via amide bonds, the product purified by SEC. The chain extension of the product as described in Example 19 will provide a multiblock biodegradable HPMA copolymer-epirubicin conjugate targetable to prostate cancer cells.

Conjugate 22c: Following dissolution of the polymer precursor in DMSO, epirubicin will be bound to a fraction of side chain terminated in TT groups. The HPMA copolymer-epirubicin-(GFLG)-TT conjugate will be isolated by precipitation into acetone and dried in vacuo. Then the solution of 80 mg of polymer will be dissolved in 300 μL DMSO and the solution added to 4 mL of OV-TL16 antibody (10 mg/mL) in phosphate buffered saline (PBS), pH 7.3 at 4° C. The solution will be maintained for 2 h, then the pH gradually increased to pH 8.5 within 3 h. The HPMA copolymer-epirubicin-OV-TL16 conjugate will be purified first using a Sephadex G25 column and then using size exclusion Superose 6 column in PBS buffer.

Example 23

Synthesis of Telechelic HPMA Copolymer Precursor Containing Malonic Acid Groups for Complexation of Platinum (P-diCOOH) (Scheme 18)

HPMA copolymer containing anti-cancer drug Platinate (P-Pt) was produced in a two-step process: first, polymer precursor was obtained by copolymerization of HPMA with a polymerizable malonic acid derivative, MA-GFLG-diCOOH. Next, a platinum agent was chelated with the polymer precursor to form the drug-polymer entity.

Synthesis of the Polymer Precursor An ampoule containing HPMA (170 mg), MA-GFLG-diCOOH (30 mg, 5 mol %), CTP-GFLG-alkyne (CTA 2, 6.68 mg) was attached to a Schlenk line. After three vacuum-nitrogen cycles to remove oxygen, 2.5 mL degassed MeOH were added, followed by addition of initiator AIBN solution in methanol (0.72 mg in 0.1 mL) via syringe. The ampoule was sealed and copolymerization was performed at 65° C. for 20 h. The polymer was obtained by precipitation into acetone and purified by re-dissolving in methanol-precipitation in acetone two more times and isolated as a pink powder. In second step, the end-modification of the copolymer (P-diCOOH) was performed by refluxing together with diN$_3$—V501 (see Example 6) its solution in NMP. The heterotelechelic copolymer was dried under vacuum. The polymer was analyzed using SEC on an AKTA FPLC system (Pharmacia) equipped with miniDAWN TREOS and OptilabEX detectors (Wyatt Technology, Santa Barbara, Calif.) using a Superose 6 HR/10/30 column with PBS (pH 7) as mobile phase. The average molecular weight of the polymer was determined by light scattering, UV, RI and calculated by ASTRA software (Mw=16 kDa, PDI=1.02). The chain extension will be done following the similar procedure in Example 19.

Linking a Platinum Agent to polyHPMA Backbone (Scheme 19)

A diaminocyclohexyl (DACH) Pt chelate DACHPt(OH$_2$)$_2$ (P. Sood et al., Bioconjugate Chem. 2006, 17, 1270-1279) will be prepared by reaction of the HPMA copolymer with DACHPt(NO$_3$)$_2$ in water containing small amount of 5% of HNO$_3$ to pH<2. The reaction mixture will be stirred at 70° C. for 1 h. The HPMA copolymer P-diCOOH will be dissolved in water. The pH of the solution will be adjusted to 12.6 by 2 M NaOH and maintained for 30 min. Then the solution will be adjusted to pH 7.4 by slow addition of 5% HNO$_3$. The platinating solution will be added with vigorous stirring. The pH will be adjusted to and kept at 5.2 using 2 M NaOH and stirred for 2 h. Then the pH will be adjusted to 7.4 using 2 M NaOH and stirred for 17 h at 38° C. After the reaction, the product will be purified and lyophilized.

Example 24

Synthesis of Telechelic HPMA Copolymer Containing Anti-Cancer Drug Gemcitabine (P-gemcitabine) (Scheme 20)

HPMA copolymer containing anti-cancer drug gemcitabine (P-gemcitabine) was produced by copolymerization of HPMA with a polymerizable derivative of the drug, MA-GFLG-gemcitabine. An ampoule containing HPMA (160 mg), MA-GFLG-gemcitabine (40 mg, 5 mol %), CTP-GFLG-alkyne (CTA 2; 6.68 mg) was attached to a Schlenk line. After three vacuum-nitrogen cycles to remove oxygen, 2.5 mL degassed MeOH were added, followed by addition of initiator AIBN solution in methanol (0.72 mg in 0.1 mL) via syringe. The ampoule was sealed and copolymerization was performed at 60° C. for 20 h. The polymer was obtained by precipitation into acetone and purified by re-dissolving in methanol-precipitation in acetone two more times. The copolymer (P-gemcitabine) was end-modified according to the procedure described in Example 18. The polymer was analyzed with SEC on an AKTA FPLC system (Pharmacia) equipped with miniDAWN TREOS and OptilabEX detectors (Wyatt Technology, Santa Barbara, Calif.) using a Superose 6 HR/10/30 column with PBS (pH 7) as mobile phase. The average molecular weight of the polymer was determined by light scattering, UV, RI and calculated by ASTRA software. The content of gemcitabine was measured by UV. The content of gem in the copolymer was 5.4%, determined by UV spectrophotometry in methanol ($\epsilon_{305}$=5710 Lmol$^{-1}$ cm$^{-1}$). The chain extension will be done following the similar procedure in Example 19.

When HPMA copolymer containing anti-cancer drug gemcitabine (P-gemcitabine) is produced using CTA 2a for RAFT copolymerization, the main chain will contain enzyme-degradable sequence Phe-Lys (FK) while side-chain contain GFLG sequence, as shown in Scheme 21.

Example 25

Synthesis of Telechelic HPMA Copolymer Containing Gemcitabine and Targeting Moiety Fab' (Scheme 22)

HPMA copolymer containing anti-cancer drug gemcitabine and targeting Fab' fragment (from anti-PSMA (prostate specific membrane antigen) antibody) will be produced in three steps: first, HPMA (129 mg, 0.9 mmol), MA-GFLG-gemcitabine (49 mg, 0.07 mmol) and APMA (5.4 mg, 0.03 mmol) will be polymerized in DMSO/H$_2$O at 70° C. using CTP-GFLG-alkyne (CTA 2) as chain transfer agent and V-501 as initiator as described in Example 20. After end-modification with diazide-V-501, the polymer will be reacted with SMCC to introduce side-chain maleimide functional groups followed by conjugation with Fab' (from 1F5 anti-CD20 antibody) via thiol-maleimide reaction, as described in Example 21. The chain extension will be done following the procedure in Example 19.

Example 26

Synthesis of Telechelic Combinational HPMA Copolymer-Drug Conjugate Containing Gemcitabine and Platinum Precursor (P-Gemcitabine-diCOOH) (Scheme 23)

HPMA copolymer containing anti-cancer drug gemcitabine and the precursor of platinate (P-gemcitabine-diCOOH) was produced by copolymerization of HPMA with a polymerizable derivative of the drug and with a comonomer containing malonic acid suitable for complexing platinum, as described in Example 22. An ampoule containing HPMA (160 mg), MA-GFLG-gemcitabine (22 mg, 2.5 mol %), MA-GFLG-diCOOH (18 mg. 2.5 mol %), CTP-GFLGK-alkyne (CTA 2, 6.68 mg) was attached to a Schlenck-line. After three vacuum-nitrogen cycles to remove oxygen, 2.5 mL degassed MeOH were added, followed by addition of initiator AIBN solution in methanol (0.72 mg in 0.1 mL) via syringe. The ampoule was sealed and copolymerization was performed at 65° C. for 20 h. The polymer was obtained by precipitation into acetone and purified by re-dissolving in methanol-precipitation in acetone two more times. The copolymer (P-gemcitabine-diCOOH) was end-modified according to the procedure described in Example 18. Platinum will be complexed with the polymer as described in Example 22. The polymer was analyzed with SEC on an AKTA FPLC system (Pharmacia) equipped with miniDAWN TREOS and OptilabEX detectors (Wyatt Technology, Santa Barbara, Calif.) using a Superose6 HR/10/30 column with PBS (pH 7) as mobile phase. The average molecular weight of the polymer was determined by light scattering, UV, RI and calculated by ASTRA software. The content of gemcitabine was measured by UV, the content of malonic acid by titration. The chain extension will be done following the similar procedure in Example 18.

Example 27

Synthesis of Heterotelechelic HPMA Copolymer Precursor Containing Two Different Attachment Points for Anticancer Drugs, TT Groups and Malonic Acid (P-TT-diCOOH) (Scheme 24)

HPMA copolymer containing reactive TT groups in side chains, and the attachment sites for complexing Pt was produced by copolymerization of HPMA with two comonomers. An ampoule containing HPMA (166 mg), MA-GFLG-diCOOH (17 mg, 2.5 mol %), MA-GFLG-TT (17 mg, 2.5 mol %) was attached to a Schlenk line. After three vacuum-nitrogen cycles to remove oxygen, 2.5 mL degassed methanol were added, followed by addition of initiator AIBN solution in methanol (0.72 mg in 0.1 mL) via syringe. The ampoule was sealed and copolymerization was performed at 65° C. for 20 h. The polymer was isolated by precipitation into acetone and purified by re-dissolving in methanol-precipitation in acetone two more times. The copolymer was isolated as an orange powder after dried under vacuum. The copolymer (P-TT-diCOOH) was further end-modified according to the procedure described in Example 18, analyzed with SEC on an AKTA FPLC system (Pharmacia) equipped with miniDAWN TREOS and OptilabEX detectors (Wyatt Technology, Santa Barbara, Calif.) using a Superose6 HR/10/30 column with PBS (pH 7) as mobile phase. The average molecular weight of the polymer was determined by light scattering, UV, RI and calculated by ASTRA software. The chain extension will be done following the similar procedure in Example 19.

Example 28

Synthesis of Azido-Telechelic polyHPMA (Scheme 25)

RAFT Polymerization of HPMA with Azido-Functionalized CTA (CTA 3). An ampoule containing HPMA (0.1 g, 0.7 mmol) and CTA 3 (3 mg, 0.008 mmol) was attached to a Schlenk line. After three vacuum-nitrogen cycles to remove oxygen, 0.5 mL degassed methanol was added followed by addition of initiator AIBN solution in methanol (0.5 mg in 0.1 mL) via syringe. The ampoule was sealed and polymerization proceeded at 60° C. for 20 h. The polymer was isolated by precipitation into acetone and purified by re-dissolving in methanol-precipitation in acetone two more times. The polyHPMA was dried under vacuum and isolated as a pink powder. Yield 60 mg. The polymer was analyzed by size-exclusion chromatography (SEC) on an AKTA FPLC system (Pharmacia) equipped with miniDAWN TREOS and OptilabEX detectors (Wyatt Technology, Santa Barbara, Calif.) using a Superose 12 HR/10/30 column with PBS (pH 7) as mobile phase. The average molecular weight of the polymer was determined by light scattering, UV, RI and calculated by ASTRA software (Mw 26 kDa, PDI 1.02).

End Group-Modification. This HPMA copolymer (10 mg) was dissolved in 100 μL of 1-methyl-2-pyrrolidinone (NMP). Diazido-V-501 (diN$_3$—V501, 20×, 20 μL) was added, the solution was bubbled with N$_2$ for 30 min, sealed and kept stirring at 70° C. for 3 h. The polymer was purified by precipitation into acetone and dried under reduced pressure. Yield 9.6 mg of white azido-telechelic polyHPMA (N$_3$-PolyHPMA-N$_3$). The completion of end group-modification was confirmed by $^1$H-NMR spectroscopy showing no detectable dithiobenzoate group (δ=7-8.5 ppm) and by FTIR showing a new peak at 2100 cm$^{-1}$ (azide).

Example 29

Synthesis of Biodegradable Multiblock polyHPMA Via Click Reaction (Scheme 26)

Biodegradable multiblock polyHPMA was synthesized via click reaction. Azido-telechelic PolyHPMA (15 mg) and alkyne-terminated peptide GFLGK (Example 11) were dissolved in 100 μL of degassed solution of L-ascorbic acid (0.25×, 0.07 mg) in DMF. Under nitrogen atmosphere, 50 μL CuBr (0.5×, 0.1 mg) solution in DMF was added. The reaction mixture kept stirring at 80° C. overnight. The polymer was precipitated into acetone and purified by dialysis against 10 mM EDTA solution and then water to remove copper salts and then dried. Yield 12 mg of click product. The polymer was analyzed by SEC. The results indicated tetramers (Mw 110.8 kDa) was obtained as well as small amount of intermediates (Mw 53.4 kDa and 24.8 kDa). The main fraction will be separated on a chromatography column.

Example 30

Synthesis of Biodegradable Multiblock polyHPMA Copolymer-Paclitaxel Conjugate (Scheme 27)

RAFT Polymerization. HPMA (886 mg), MA-GFLG-PTX (245 mg), MA-Tyr (15 mg), (CTP-GFLG)$_2$K (6.6 mg) and AIBN (0.5 mg) were dissolved in methanol (3.7 mL). The solution was bubbled with N$_2$ for 30 min, sealed and polymerized at 55° C. for 30 h. After polymerization, the copolymer was purified by dissolution-precipitation in methanol-acetone 3 times, then washed with acetone and dried under reduced pressure. Yield 454 mg of pink telechelic HPMA copolymer-paclitaxel (Mn 103 kDa, PDI 1.05).

End Group Modification. The HPMA copolymer-paclitaxel (440 mg) was reacted with dialkyne-V-501 (61 mg, 0.172 mmol) in 4.0 mL deoxygenated methanol at 70° C. for 3 h. The copolymer was purified by dissolution-precipitation in methanol-acetone twice and dried, resulting in the α,ω-dialkyne telechelic HPMA copolymer-paclitaxel in 84% yield (370 mg).

Click Reaction. α,ω-dialkyne telechelic HPMA copolymer-paclitaxel (103 kDa, 350 mg, 3.4 µmol), (azido-GFLG)$_2$K (4.0 mg, 3.4 µmol) and sodium ascorbate (8 mg, 40 µmol) were added in a vial. The vial was vacuumed and refilled with nitrogen three times before adding 1.1 mL of deoxygenated DMF. Deoxygenated solution of CuSO$_4$ (3.2 mg, 20 µmol, 200 µL in water) was added. The vial was sealed. The solution was stirred at room temperature for 20 h. The copolymer was precipitated into acetone and dried under vacuum, and further purified via PD-10 column. The click product was fractionated using preparative Superose 6 HR 16/60 column and acetate buffer (pH=6.5) as eluents. The flow rate was 1 mL/min and the fraction (Mn 306 kDa, PDI 1.09) was collected, dialysis and freezing dried, giving in the white powder in 27.7% yield (98 mg).

Figure 5:
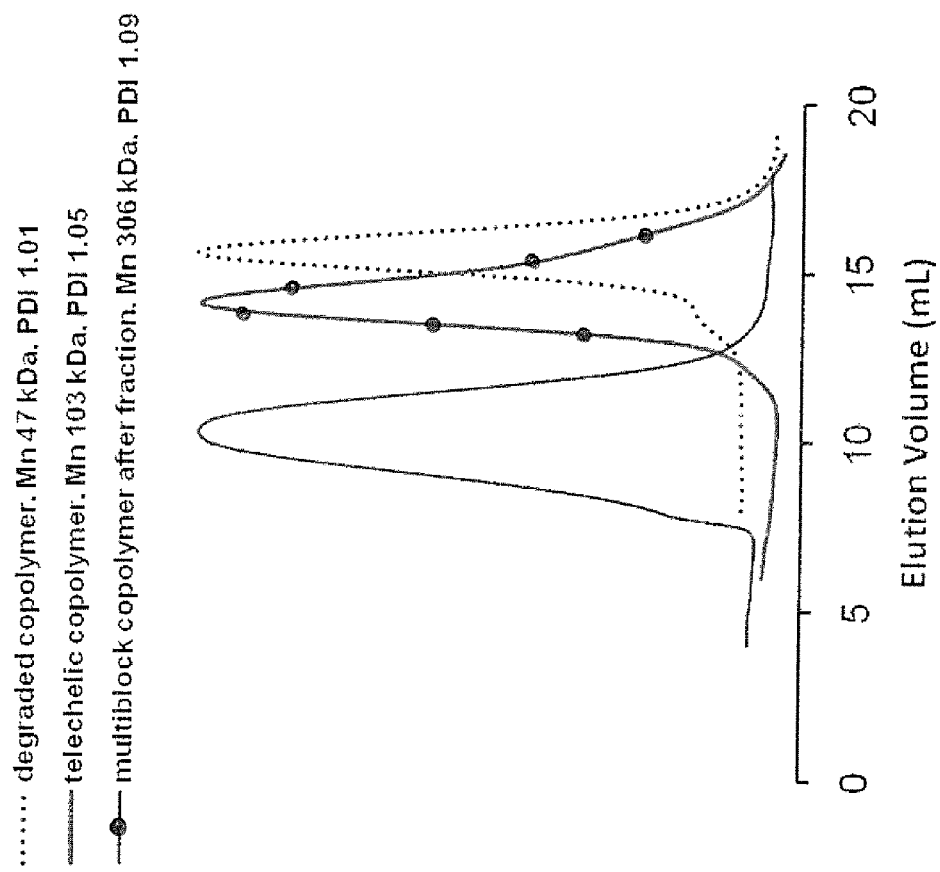
FIG. 5 shows the degradation of multiblock copolymer fraction (Mn 306 kDa, PDI 1.09) performed in McIlvaine's buffer (50 mM citrate/0.1 M phosphate) at pH 6.0, 37° C. using papain (2.0 µM) as a model enzyme, giving in the degraded HPMA copolymer (Mn 47 kDa, PDI 1.01). The paclitaxel (5.4 wt %) was cleaved from the copolymer conjugate in papain (10 µM).

Degradation. The degradation of multiblock copolymer fraction (Mn 306 kDa, PDI 1.09) was performed in McIlvaine's buffer (50 mM citrate/0.1 M phosphate) at pH 6.0, 37° C. using papain (2.0 µM) as a model enzyme, giving in the degraded HPMA copolymer (Mn 47 kDa, PDI 1.01). The paclitaxel (5.4 wt %) was cleaved from the copolymer conjugate in papain (10 µM). Results are depicted in FIG. 5.

Examples of the Synthesis of Backbone Degradable HPMA Copolymer-Drug Conjugates Using the Thiol-Ene Reactions

Example 31

Synthesis of Thiol-Telechelic PolyHPMA Using (CTP-GFLG)$_2$K as CTA and Polymer Chain Extension (Scheme 28)

Polymerization of HPMA. HPMA (330 mg), (CTP-GFLG)$_2$K (12 mg) and AIBN (0.5 mg) were dissolved in methanol (2.8 mL). The solution was bubbled with N$_2$ for 30 min, sealed and polymerized at 50° C. for 48 h. After polymerization, the polymer was purified by dissolution-precipitation in methanol-acetone 3 times, then washed with acetone and dried under reduced pressure. Yield 156 mg of pink polymer (Mw 19.4 kDa, PDI 1.05).

Aminolysis. HPMA. polymer CTA-PolyHPMA-CTA (100 mg) was dissolved in 800 µL of methanol; n-BuNH$_2$ (50 µL) was added and the mixture shaken for 10 min. Then, the polymer was purified by dissolution-precipitation in methanol-acetone 3 times, washed with acetone and dried under reduced pressure. Yield 76 mg of thiol telechelic PolyHPMA.

Reduction. HPMA copolymer docetaxel conjugate CTA-polyHPMA-CTA (10 mg), reducing agent TCEP.HCl (20 mg) were added into 100 µL methanol, and stirred overnight at room temperature. After reduction, the polymer was precipitated into acetone, and washed with ether or acetone 3 times, dried under reduced pressure at room temperature. Yield 8 mg of thiol telechelic PolyHPMA.

Chain Extension with 2,2'-dipyridine Disulfide. Thiol telechelic PolyHPMA (6 mg) and 2,2'-dipyridine disulfide (6 mg) were dissolved in 100 µL of methanol. The reaction mixture was shaken at room temperature for 3 h. The polymer was precipitated in acetone and purified by the dissolution-precipitation method (complete removal of unreacted PySSPy), then dried. Yield 6 mg of telechelic PySS-PolyHPMA. Telechelic PySS-PolyHPMA (6 mg) and thiol telechelic PolyHPMA (6 mg) were dissolved in 40 µL of methanol, respectively; then the 2 solutions were mixed and kept shaking at 40° C. overnight. The polymer was purified by dissolution-precipitation in methanol-acetone 3 times, washed with acetone and dried under reduced pressure. Yield 12 mg of poly(PHPMA-SS).

Interfacial Chain Extension. Thiol telechelic PolyHPMA (15 mg) was dissolved in 200 µL of water and bubbled with N$_2$ for 5 min. bis-MAL-dPEG3 (CAS#756525-89-0) (0.3 mg) was dissolved in 100 µL of DCM. The two solutions were mixed in 1 ml of ampoule and flame sealed. The reaction mixture was stirred vigorously for 20 h at room temperature. The polymer was precipitated into acetone, washed with acetone 3 times and dried under reduced pressure. Yield 15 mg of chain-extended polymer.

Chain Extension Via Disulfide Bond Formation by DMSO Oxidation. Thiol telechelic PolyHPMA (5 mg) was dissolved in mixed solvent of 20 µL of water and 10 µL of DMSO. The solution was stirred for 10 h at room temperature. The polymer was precipitated into acetone, washed with acetone 3 times and dried under reduced pressure. Yield 5 mg of polymer (Mw 168.1 kDa, PDI 1.44).

Chain Extension with bis-MAL-dPEG3 (CAS#756525-89-0). Thiol telechelic PolyHPMA (26 mg) and bis-MAL-dPEG3 (10.3 mg) were dissolved in 60 µL DMF. The reaction mixture was shaken at room temperature for 8 h. The polymer was precipitated into acetone and purified by dissolution-precipitation method (complete removal of unreacted bis-MAL-dPEG3) and dried. Yield 27 mg of telechelic MAL-PolyHPMA. Telechelic MAL-PolyHPMA (27 mg) and telechelic HS-PolyHPMA (25 mg) were dissolved in 50 µL DMF, respectively. The two solutions were mixed and kept shaking overnight at room temperature. The polymer was purified by dissolution-precipitation in methanol-acetone 3 times, washed with acetone and dried under reduced pressure. Yield 50 mg of polymer (Mw 100.4 kDa, PDI 2.31).

Example 32

Enzyme-Catalyzed Degradation of Multiblock polyHPMA

The degradation of multiblock polyHPMA obtained from thiol-ene reactions was performed in McIlvaine's buffer (50 mM citrate/0.1 M phosphate) at pH 5.0, 37° C., using papain or cathepsin B. Cathepsin B stock solution (0.35 mg/mL) and papain stock solution (0.45 mg/mL) were used in polymer cleavage study.

Papain (0.45 mg/mL, 0.1 mL) (or cathepsin B, 0.35 mg/mL, 0.1 mL) was mixed with 0.8 mL of buffer containing 5 mM GSH and the mixture was pre-incubated for 5 min at 37° C. Multiblock multiblock HPMA copolymer-DOX conjugate (227.7 kDa fraction) in 0.1 mL of buffer containing 4 mg of the polymer was added and incubated at 37° C. At scheduled time intervals, 0.1 mL sample was withdrawn and mixed with 0.4 mL of PBS (pH 7.3) containing 0.05 mL of 1 M sodium iodoacetate. The sample was analyzed by SEC using the ÄKTA FPLC system equipped with miniDAWN TREOS and OptilabEX detectors using a Superose 6 HR/10/30 column with PBS (pH 7.3) as mobile phase.

Figure 3:
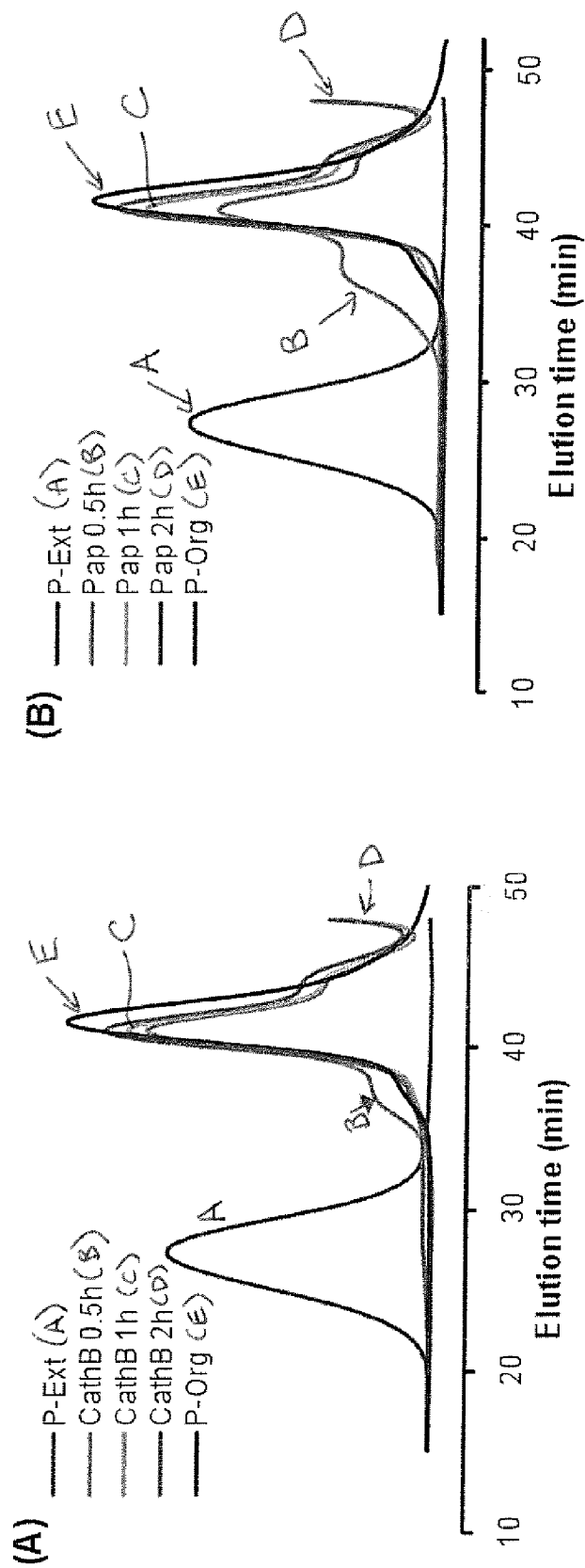
FIG. 3 shows SEC profiles of initial telechelic $\alpha,\omega$-dithiol-polyHPMA (P-Org), extended multiblock polyHPMA fraction (P-Ext) and degradation products after incubation with (A) cathepsin B and (B) papain at different time intervals.

The average molecular weight of the degraded products is close to the starting polyHPMA as depicted on FIG. 3 (left panel—degradation with cathepsin B; right panel—degradation with papain). In addition to the degradation of the main chain, DOX was simultaneously released by degradation of oligopeptide side-chains.

Example 33

Synthesis of Thiol-Telechelic HPMA Copolymer Containing Anti-Cancer Drug Docetaxel and Chain Extension Copolymerization. HPMA (98 mg), MA-GFLG-docetaxel (16 mg, 2 mol %), (CTP-GFLG)$_2$K (4.1 mg) and AIBN (0.2 mg) were dissolved in methanol (1 mL). The solution was bubbled with $N_2$ for 30 min, sealed and polymerized at 50° C. for 48 h. The polymer was purified by dissolution-precipitation in methanol-acetone 3 times, washed with acetone and dried under reduced pressure. Yield 35 mg of pink polymer P-DTX-CTA2 (Mw 11.6 kDa, PDI 1.12). The conjugate contained 1.5 mol % of DTX (0.09 g/g polymer).

Aminolysis. P-DTX-CTA2 (20 mg) was dissolved in 100 μL of methanol, n-BuNH$_2$ (10 μL) was added and the mixture shaken for 5 min. Then, the polymer was purified by dissolution-precipitation in methanol-acetone 3 times, washed with acetone and dried under reduced pressure. Yield 15 mg of telechelic P-DTX (HS-[polyHPMA-DTX]-SH)

Chain Extension. Thiol telechelic P-DTX (7 mg) and bis-MAL-dPEG3 (5 mg) were dissolved in 20 μL DMF. The reaction mixture was shaken at room temperature for 8 h. The polymer was precipitated into acetone and purified by dissolution-precipitation method (complete removal of unreacted bis-MAL-dPEG3), then dried. Yield 8 mg of telechelic P-DTX-MAL2. Telechelic P-DTX-MAL2 (8 mg) and telechelic P-DTX-SH2 (6.5 mg) were dissolved in 20 μL DMF, respectively. The two solutions were mixed and kept shaking overnight at room temperature. The polymer was purified by dissolution-precipitation in methanol-acetone 3 times, washed with acetone and dried under reduced pressure. Yield 12 mg of polymer (Mw 79.4 kDa, PDI 3.33).

Example 34

Synthesis of Thiol-Telechelic HPMA Copolymer Containing Thiazolidine-2-Thione (TT), Attachment of Anti-Cancer Drug Doxorubicin and Chain Extension Copolymerization. HPMA (270 mg), MA-GFLG-TT (67 mg, 6 mol %), (CTP-GFLG)$_2$K (12 mg) and AIBN (0.5 mg) were dissolved in methanol (3 mL). The solution was bubbled with $N_2$ for 30 min, sealed and polymerized at 50° C. for 48 h. After polymerization, the polymer was purified by dissolution-precipitation in methanol-acetone 3 times, washed with acetone and dried under reduced pressure. Yield 139 mg of pink polymer P-TT-CTA2 (Mw 19.8 kDa, PDI 1.07).

Drug Binding and Aminolysis. P-TT-CTA2 (78 mg) and doxorubicin (20 mg) were dissolved in 500 μL of DMSO. DIPEA (12 μL) was added under stirring. The system was stirring overnight at room temperature; then, the polymer was purified by dissolution-precipitation in methanol-acetone 3 times, washed with acetone and dried under reduced pressure. Yield 30 mg of telechelic P-Dox-SH2.

Chain Extension. Telechelic P-DOX-SH2 (10 mg) and bis-MAL-dPEG3 (7 mg) were dissolved in 40 μL DMF. The reaction mixture was shaken at room temperature for 8 h. The polymer was precipitated into acetone and purified by dissolution-precipitation (complete removal of unreacted bis-MAL-dPEG3), then dried, Yield 10.5 mg of telechelic P-DOX-MAL2. Telechelic P-DOX-MAL2 (10.5 mg) and telechelic P-DOX-SH2 (10 mg) were dissolved in 20 μL DMF, respectively. The two solutions were mixed and kept shaking overnight at room temperature. The polymer was purified by dissolution-precipitation in methanol-acetone 3 times, washed with acetone and dried under reduced pressure. Yield 20 mg of polymer (Mw 98.1 kDa, PDI 2.37). The content of the drug was measured by UV-vis. The conjugate contained 2.48 mol % of DOX (0.08 g/g polymer).

Example 35

Synthesis of Thiol Telechelic Combinational HPMA Copolymer-Drug Conjugate Containing Doxorubicin and Docetaxel HPMA (140 mg), MA-GFLG-Docetaxel (12.5 mg, 1 mol %), MA-GFLG-DOX (9.6 mg, 1 mol %; (CTP-GFLG)$_2$K (11.5 mg) and AIBN (0.4 mg) were dissolved in methanol (1.4 mL). The solution was bubbled with $N_2$ for 30 min, sealed and polymerized at 50° C. for 30 h. After polymerization, the polymer was purified by dissolution-precipitation in methanol-acetone 3 times, washed with acetone and dried under reduced pressure. Yield 65 mg of the combinational copolymer (Mw 29.9 kDa, PDI 1.36). The content of the drug was measured by UV-vis and by papain cleavage. The conjugate contained 0.96 mol % of DOX (0.03 g/g polymer) and 0.75 mol % of DTX (0.04 g/g polymer).

Example 36

Synthesis of Thiol-Telechelic Combinational HPMA Copolymer Containing Doxorubicin and Fab' Targeting Moieties (Scheme 29)

HPMA (90 mol %), MA-GFLG-Dox (5 mol %), MA-NH$_2$HCl (5 mol %), (CTA-GFLG)2K (as chain transfer agent, with an amount suitable for preparation of a 10 kDa copolymer) and AIBN (⅕ amount of the CTA) was dissolved in methanol. The solution was bubbled with $N_2$ for 30 min, sealed and polymerized at 50° C. for 48 h. After polymerization, the polymer was purified by dissolving-precipitation in methanol-acetone 3 times, then washed with acetone and dried under reduced pressure.

The copolymer CTA-Poly(HPMA-Dox-NH$_2$)-CTA will be dissolved in DMF, DIPEA (2 equivalent to amount of amino groups in the copolymer) will be added. SMCC (3×) in DMF was added at 0° C. The reaction mixture will be stirred under room temperature for 12 h. After reaction, the product will be purified by dissolving-precipitation in methanol-acetone 3 times, then washed with acetone and dried under reduced pressure.

The copolymer CTA-Poly(HPMA-Dox-MAL)-CTA will be dissolved in PBS buffer (pH 6.0). Fab' in PBS buffer (pH 6.0) will be added. The coupling reaction mixture will be gently stirred under room temperature for 12 h. After reaction, 2-mercaptoethanol will be added to the solution and continue stir for 1 h. The pH of the solution will be adjusted to 9 with 1N NaOH and stirred for 10 h to remove the end dithioester groups. The copolymer conjugate will be purified by dialysis (100 kDa MWCO) against PBS buffer (pH 6), and concentrated by ultrafiltration.

Telechelic HS-Poly(HPMA-Dox-Fab')-SH and bis-MAL-dPEG3 (CAS#756525-89-0, equivalent to the copolymer) will be dissolved in PBS buffer (pH 6). The reaction mixture will be shaken at room temperature for 2 days. After reaction, the extended copolymer conjugate will be purified by dialysis (100 kDa MWCO) against PBS buffer (pH 6), and concentrated by ultrafiltration. Final purification of the conjugate will be performed by SEC. The content of Fab' and the molecular weight and polydispersity will be measured by UV-vis and FPLC.

Examples of the Synthesis of Backbone Degradable HPMA Copolymer-Drug Conjugates Using Other Approaches Example 37

Introduction of Hydrolytically Cleavable Ester Bond in HPMA Copolymer Main Chain Via RAFT Polymerization (Scheme 30)

HPMA, 5,6-benzo-2-methylene-1,3-dioxepane or 2-methylene-1,3-dioxepane (1 wt % of monomers), CTA 1 (3 wt % of total monomers) and AIBN (20 wt % of CTA) will be dissolved in methanol (concentration of the total monomers will be 15 wt %). The solution will be bubbled with $N_2$ for 30 min, sealed and polymerized at 50° C. for 24 h. After polymerization, the polymer will be purified by dissolve-precipitate in methanol-acetone 3 times and then washed with acetone, dried under reduced pressure.

Example 38

Synthesis of Multisegment HPMA Copolymer Conjugates Via Hetero Diels-Alder Reaction (Scheme 31)

(1) HDA-CTA
4-cyanodithiobenzoic acid. A mixture of 4-cyanobenzoic acid (10 g, 68 mmol) and phosphorus pentasulfide (8 g, 18 mmol) in toluene (200 mL) was reflux for 12 h. the red product 4-cyanodithiobenzoic acid was washed with 5% HCl×3 and brine×3. Then the product was extracted into 200 mL 5% NaOH and washed with ether and benzene.

bis(4-cyanothiobenzoyl)disulfide. Potassium ferricyanide (III) (25 g, 76 mmol) was dissolved in deionized water (300 mL) and added dropwise to the sodium 4-cyanodithiobenzoate via an addition funnel over a period of 1 h under vigorous stirring. The red precipitate was filtered and washed with deionized water until the washings became colorless. The solid was dried in vacuo at room temperature overnight. The product bis(4-cyanothiobenzoyl)disulfide was recrystallized from ethanol.

Synthesis of 4-cyanopentanoic acid 4-cyanodithiobenzoate. 4,4'-azobis(4-cyanopentanoic acid) (5.6 g, 20 mmol) and bis(cyanothiobenzoyl)disulfide (4 g, 11.2 mmol) were added to a 250 mL round-bottomed flask containing 80 mL of distilled ethyl acetate. The reaction solution was refluxed for 18 h. The ethyl acetate was removed in vacuo. The product was isolated by column chromatography (silicagel 60 Å, 70-230 mesh) using ethyl acetate:hexane (2:3) as eluent.

The other benzene substituted dithioester CTA and pyridyl dithioester CTA will be synthesized by the similar method.

HAD-CTA.
GFLG peptide containing Telechelic benzene substituted dithioester CTA or pyridyl dithioester CTA will be synthesized by the same SPPS method as described in example 9.

(2) α,ω-Dicyclopentadienyl-PEG.
α,ω-Dibromo-PEG will be dissolved in THF and cooled to 0° C. To this solution 3 equivalents sodium cyclopentadienide (2.0 M in THF) will be slowly added. The mixture will be stirred at 0° C. for 30 mins and then 12 h at room temperature. The resulting mixture will be poured into a saturated $NH_4Cl$ solution and extracted with DCM. The organic phase will be washed with cold distilled water, dried over $MgSO_4$, and concentrated and precipitation in cold diethyl ether. The product will be collected and dried under reduced pressure.

(3) Extension by Hetero-Diels-Alder Reaction
HPMA, comonomers, HDA-CTA and AIBN will be dissolved in methanol and finial monomers concentration will be 13~15 wt %. The solution will be bubbled with $N_2$ for 30 min, sealed and polymerized at 50° C. for 48 h. After polymerization, the polymer will be purified by dissolution-precipitation in methanol-acetone 3 times, then washed with acetone and dried under reduced pressure. α,ω-Dicyclopentadienyl-PEG and dithioester terminated polymer (equivalent of terminal functional group) will be dissolved in DMF and stirred at room temperature for 1 day. The polymer will be purified by dissolution-precipitation in methanol-acetone 3 times, washed with acetone and dried under reduced pressure.

Example 39

Synthesis of N-methacryloylglycylglycyl-thiazolidine-2-thione (MA-GG-TT) (Scheme 32)

The synthesis of MA-GG-TT was similar to the synthesis of MA-GFLG-TT in Example 1. N-methacryloylglycylglycine (MA-GG-OH) was coupled with 2-mercaptothiazoline in DCM mediated by EDCI in presence of catalytic amount of DMAP. After reaction, the product was purified by recrystallization from MeOH solution.

Example 40

Synthesis of N-methacryloylglycylglycylvalinylcitrulline (MA-GlyGlyValCit-Gem) (Scheme 33)

MA-GlyGlyValCit-OH will be synthesized by solid phase peptide synthesis (SPPS) methodology. Fmoc protected amino acids, Fmoc-Cit-OH and Fmoc-Val-OH, followed by MA-GlyGly-OH will be coupled successively to the 2-Cl-trityl chloride beads by using HBTU as the coupling agent and 20% piperidine in DMF as the deprotection agent. The peptide will be isolated following cleavage from 2-Cl-trityl resin by TFA:$H_2O$:TIS (95:2.5:2.5) for 2 h, precipitated in ether and dried under vacuum.

MA-GlyGlyValCit-Gem will be synthesized by reaction of MA-GlyGlyValCit-OH with gemcitabine hydrochloride in DMF in the presence of DIPEA and DCC at 4° C. After the reaction, the solvent will be removed by rotary evaporation. The crude product will be purified by silica gel column chromatography.

Example 41

Synthesis of Two-Arm CTA, $N^\alpha,N^\delta$-bis(4-cyano-4-(phenylcarbonothioylthio)pentanoylvalinylcitrullinyl)lysine (CTP-Val-Cit)$_2$K; CTA 5.1) and $N^\alpha,N^\delta$-bis(4-cyano-4-(phenylcarbonothioylthio)pentanoylphenylalanyllysyl)lysine (CTP-Phe-Lys)$_2$K; CTA 5.2) (Scheme 34)

The two-arm CTA (CTP-Val-Cit)$_2$K will be synthesized by the same method as described in Example 10. Briefly, Fmoc protected amino acids, Fmoc-Lys(Fmoc)-OH, Fmoc-Cit-OH and Fmoc-Val-OH will be coupled successively to the 2-Cl-trityl chloride beads. After deprotection, the chain transfer agent, 4-cyanopentanoic acid dithiobenzoate, will be coupled to the valinyl residues using DIC as the coupling agent. The peptide will be isolated following cleavage from 2-Cl-trityl resin by 30% TFE in DCM for 2 h.

Using the same method, (CTP-Phe-Lys)$_2$K will be synthesized. Briefly, Fmoc protected amino acids, Fmoc-Lys(Fmoc)-OH, Fmoc-Lys(Boc)-OH and Fmoc-Phe-OH will be coupled successively to the 2-Cl-trityl chloride beads. After deprotection, the chain transfer agent, 4-cyanopentanoic acid dithiobenzoate, will be coupled to the phenylalanyl residues using DIC as the coupling agent. The peptide will be isolated following cleavage from 2-Cl-trityl resin by 30% TFE in DCM for 2 h.

Example 42

Synthesis of Diazido Compound for Chain Extension, $N^\alpha,N^\delta$-bis(azidobenzoylvalinylcitrullinyl)lysine (N$_3$-Val-Cit-N$_3$) and $N^\alpha,N^\delta$-bis(azidobenzoylphenylalanyllysyl)lysine (N$_3$-Phe-Lys-N$_3$) (Scheme 35)

The telechelic, azido-group functionalized enzyme-sensitive peptides N$_3$-Val-Cit-N$_3$ will be synthesized by the same method as described in Example 12. Briefly, Fmoc protected amino acids, Fmoc-Lys(Fmoc)-OH, Fmoc-Cit-OH and Fmoc-Val-OH will be coupled successively to the 2-Cl-trityl chloride beads by using HBTU as the coupling agent and 20% piperidine in DMF as the deprotection agent. After deprotection, azidobenzoic acid will be coupled to the glycyl residues using DIC as the coupling agent. The peptide will be isolated following cleavage from 2-Cl-trityl resin by 30% TFE in DCM for 2 h. The peptide will be characterized by $^1$H-NMR spectrum.

By the same method, N$_3$-Phe-Lys-N$_3$ will be synthesized. Briefly, Fmoc protected amino acids, Fmoc-Lys(Fmoc)-OH, Fmoc-Lys(Boc)-OH and Fmoc-Phe-OH will be coupled successively to the 2-Cl-trityl chloride beads. After deprotection, azidobenzoic acid will be coupled to the glycyl residues using DIC as the coupling agent. The peptide will be isolated following cleavage from 2-Cl-trityl resin by 30% TFE in DCM for 2 h. The peptide will be characterized by $^1$H-NMR spectrum.

Example 43

Synthesis of HPMA Copolymer Conjugate Containing Two Drugs, DOX and Gem, P-DOX-Gem (Scheme 36)

HPMA (90 mol %), MA-GG-TT (5 mol %), MA-GFLG-Gem (5 mol %), (CTP-Val-Cit)$_2$K or (CTP-Phe-Lys)$_2$K and AIBN will be dissolved in methanol. The concentration of the monomer will be about 15 wt %. The solution will be bubbled with N$_2$ for 30 min, sealed and polymerized at 50° C. for 24 h. After polymerization, the polymer will be purified by dissolution-precipitation in methanol-acetone 3 times, washed with acetone and dried under reduced pressure.

The copolymer CTA-P(HPMA-TT-Gem)-CTA (100 mg) will be dissolved in 800 µL of DMF and added to NH$_2$NH$_2$ (100 µL) in 800 µL of DMF and the mixture will be shaken for 30 min at room temperature. Then, the polymer will be purified by dissolution-precipitation in methanol-acetone 3 times, washed with acetone and dried under reduced pressure.

The copolymer HS-P(HPMA-CONHNH$_2$-Gem)-SH (100 mg) will be dissolved in 1 mL of MeOH/H$_2$O (1/1). DOX (20 mg) in 0.5 mL of MeOH/H$_2$O (1/1) will be added. The reaction mixture will be stirred at room temperature. Then, the polymer will be purified by dissolution-precipitation in methanol-acetone 3 times, washed with acetone and dried under reduced pressure.

Telechelic copolymer conjugate HS-P(HPMA-CONHNH$_2$DOX-Gem)-SH and bis-MAL-dPEG3 (equivalent) will be dissolved in DMF. The reaction mixture will be shaken at room temperature for 24 h. The polymer will be precipitated into acetone and purified by dissolving-precipitation method.

Example 44

Synthesis of HPMA Copolymer Conjugate Containing Two Drugs, DTX and Gem, P-DTX-Gem (Scheme 37)

HPMA (90 mol %), MA-GFLG-DTX (5 mol %), MA-GlyGlyValCit-Gem (5 mol %), CTA1 (Example 6) and AIBN will be dissolved in methanol. The concentration of the monomer will be about 15 wt %. The solution will be bubbled with N$_2$ for 30 min, sealed and polymerized at 50° C. for 24 h. After polymerization, the polymer will be purified by dissolution-precipitation in methanol-acetone 3 times, washed with acetone and dried under reduced pressure.

The copolymer alkyne-P(HPMA-DTX-Gem)-alkyne and N$_3$-Val-Cit-N$_3$ or N$_3$-Phe-Lys-N$_3$ will be dissolved in degassed solution of L-ascorbic acid (0.5×) in DMF. Under nitrogen atmosphere, CuBr (0.5×) solution in DMF will be added. The reaction mixture will be kept stirring for 48 h at room temperature. The polymer will be precipitated into acetone and purified by dialysis against 10 mM EDTA solution, then in water to remove copper salts, and then freeze-dried.

Example 45

In Vivo Evaluation of the Efficacy of Multiblock HPMA Copolymer-DOX Conjugate

Multidrug resistant human ovarian carcinoma A2780/AD cells (5×10$^6$) were transplanted s.c. into the (right) flank of female athymic nu/nu mice. When the tumor reached a size of about 1 cm$^2$, the mice were treated i.p. three times (days 1, 4, and 7) with HPMA copolymer-DOX conjugates (25 mg DOX equivalent/kg).

Figure 4:
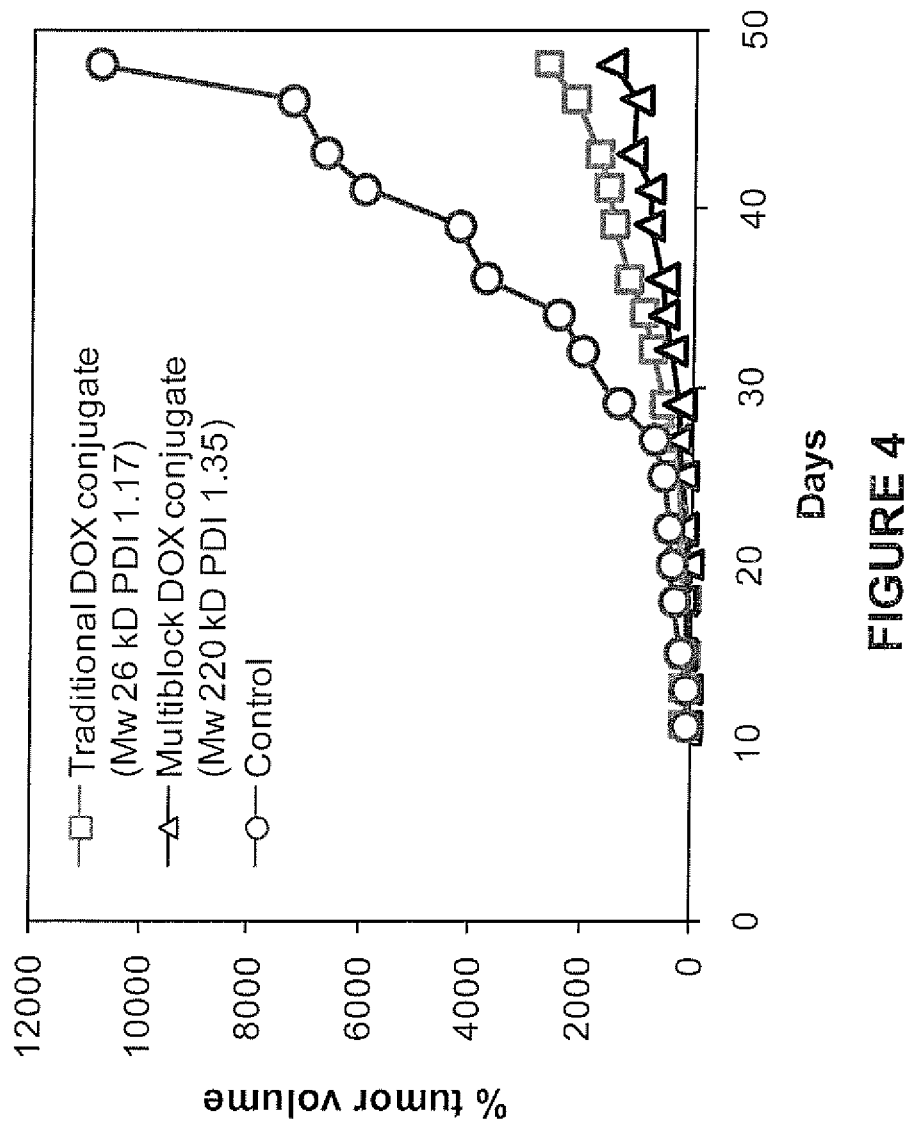
FIG. 4 shows the growth inhibition of HPMA copolymer-DOX conjugate on s.c. A2780AD (resistant) human ovarian carcinoma xenografts in female athymic nu/nu mice. Compared with traditional DOX conjugate, high molecular weight multiblock DOX conjugate demonstrated higher antitumor activity (higher inhibition of tumor growth).

The growth inhibition of HPMA copolymer-DOX conjugate on s.c. A2780AD (resistant) human ovarian carcinoma xenografts in female athymic nu/nu mice is shown in FIG. 4. Compared with traditional DOX conjugate, high molecular weight multiblock DOX conjugate demonstrated higher antitumor activity (higher inhibition of tumor growth).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

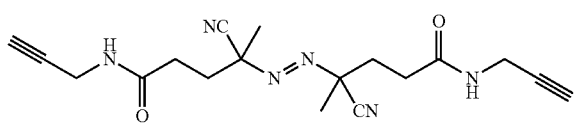

dialkyne functionized V-501

SCHEME 1

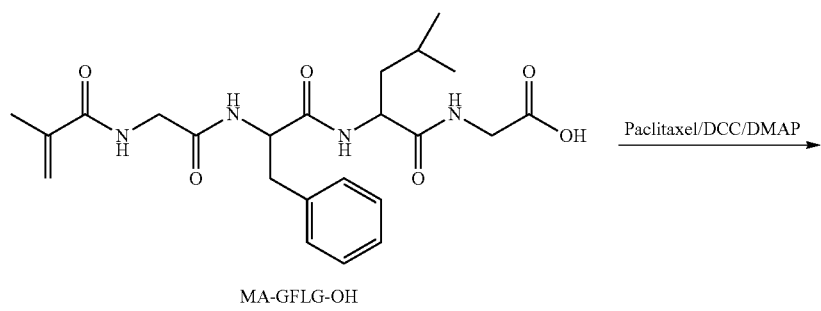

MA-GFLG-OH

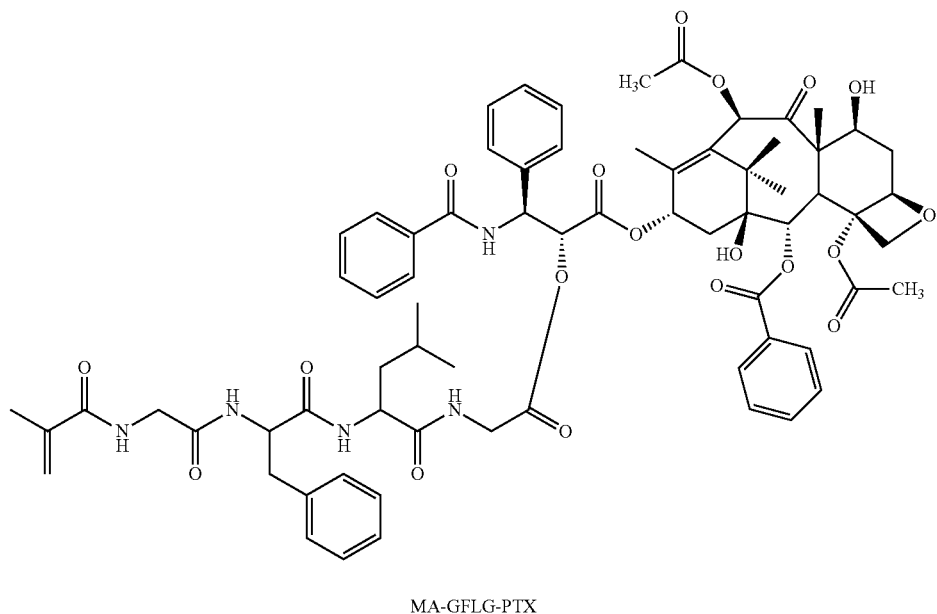

MA-GFLG-PTX

SCHEME 2

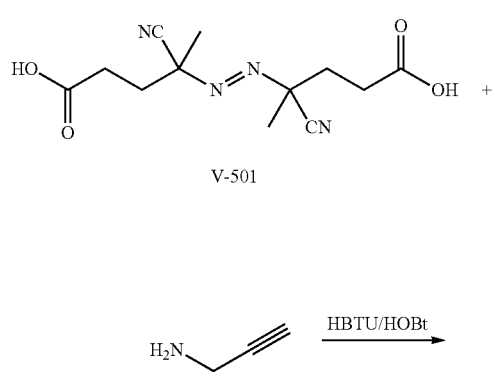

V-501

SCHEME 3

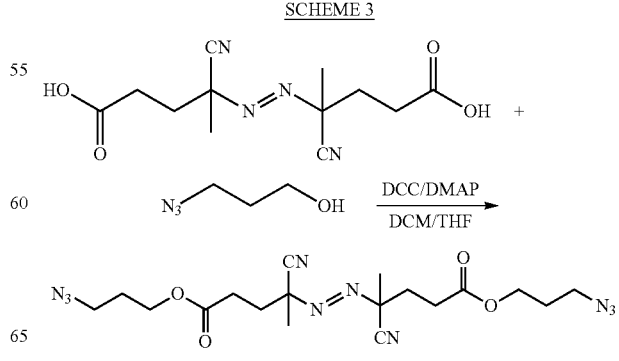

SCHEME 4
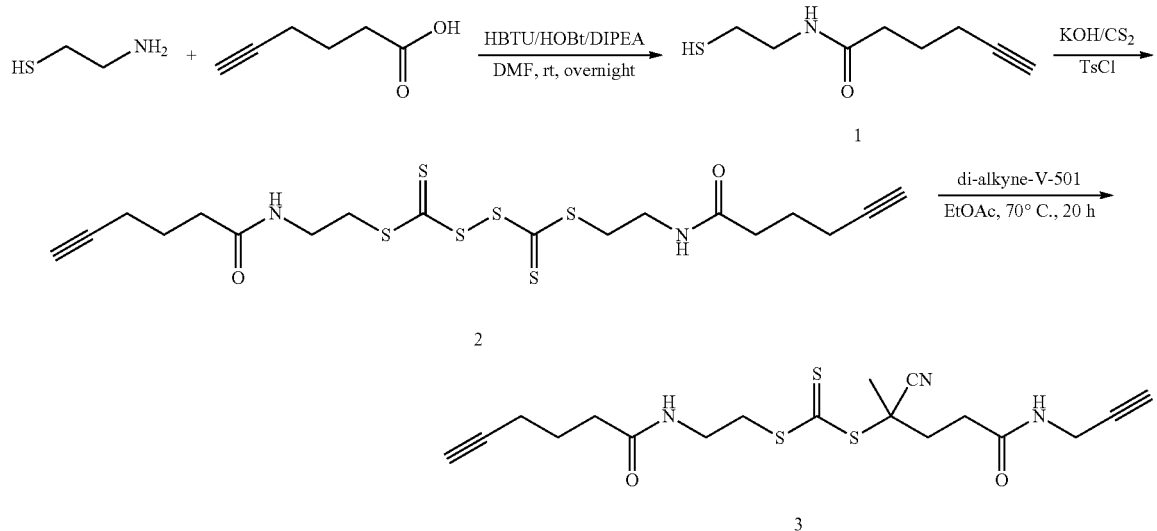
SCHEME 5
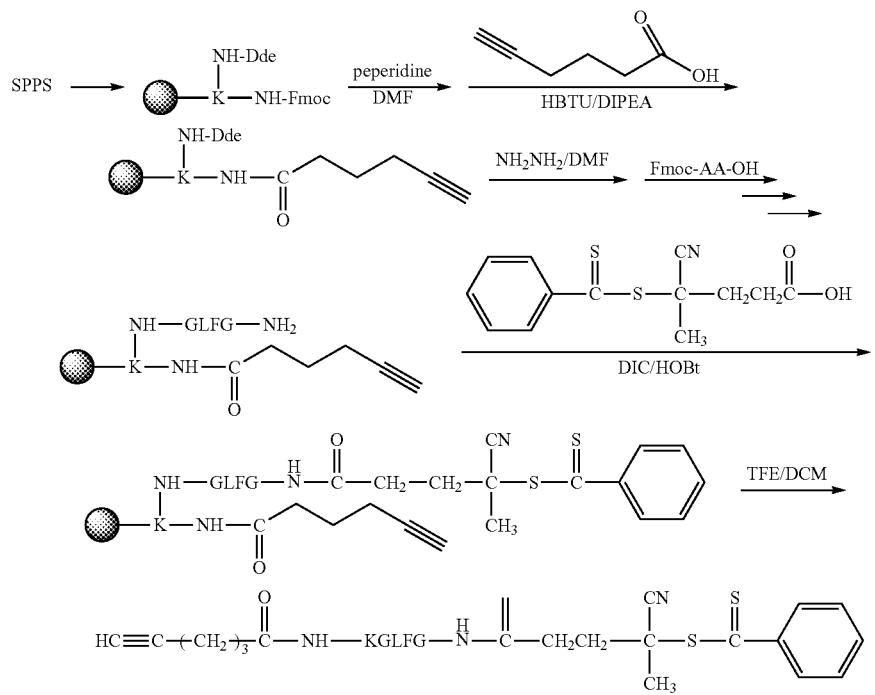
CTP-Gly-Phe-Leu-Gly-alkyne, (CTP-GFLG-alkyne) CTA 2
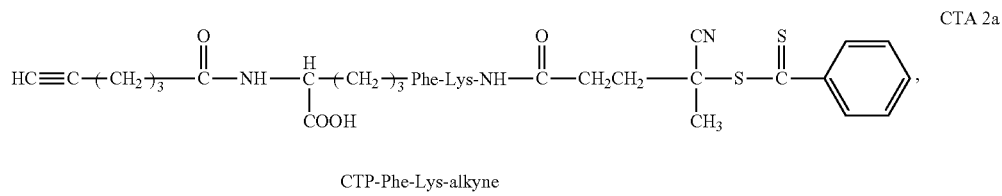
CTP-Phe-Lys-alkyne

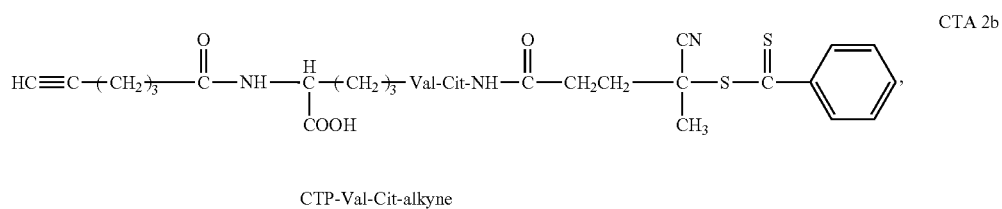
CTP-Val-Cit-alkyne
SCHEME 6
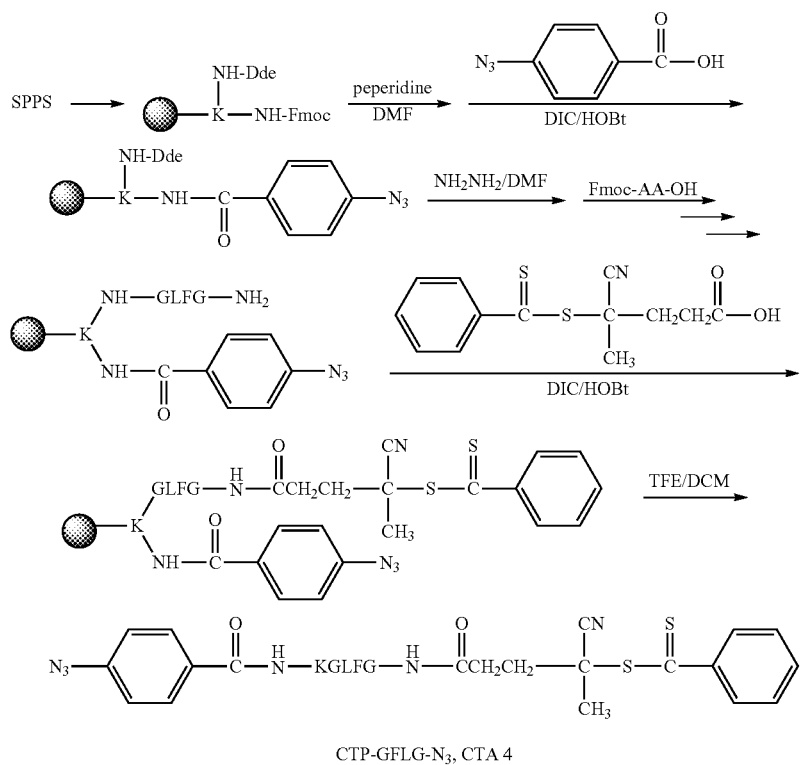
CTP-GFLG-N₃, CTA 4
SCHEME 7
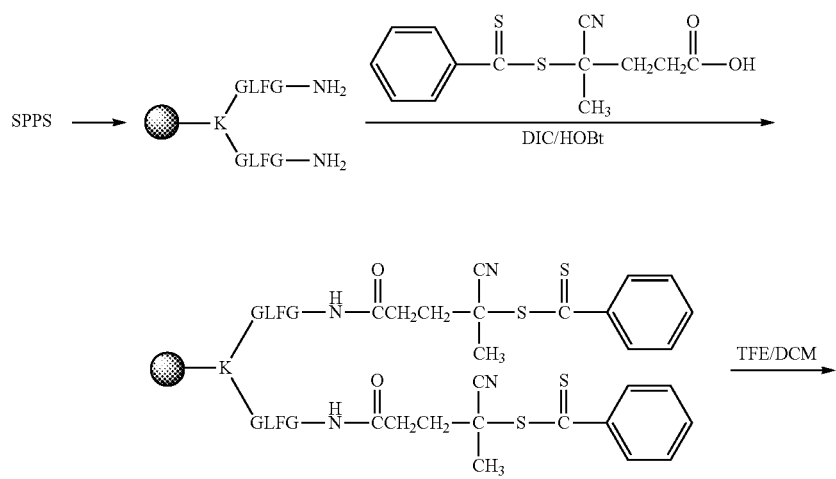

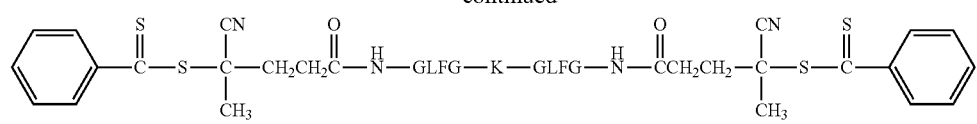
(CTP-GFLG)₂K, CTA 5
SCHEME 8
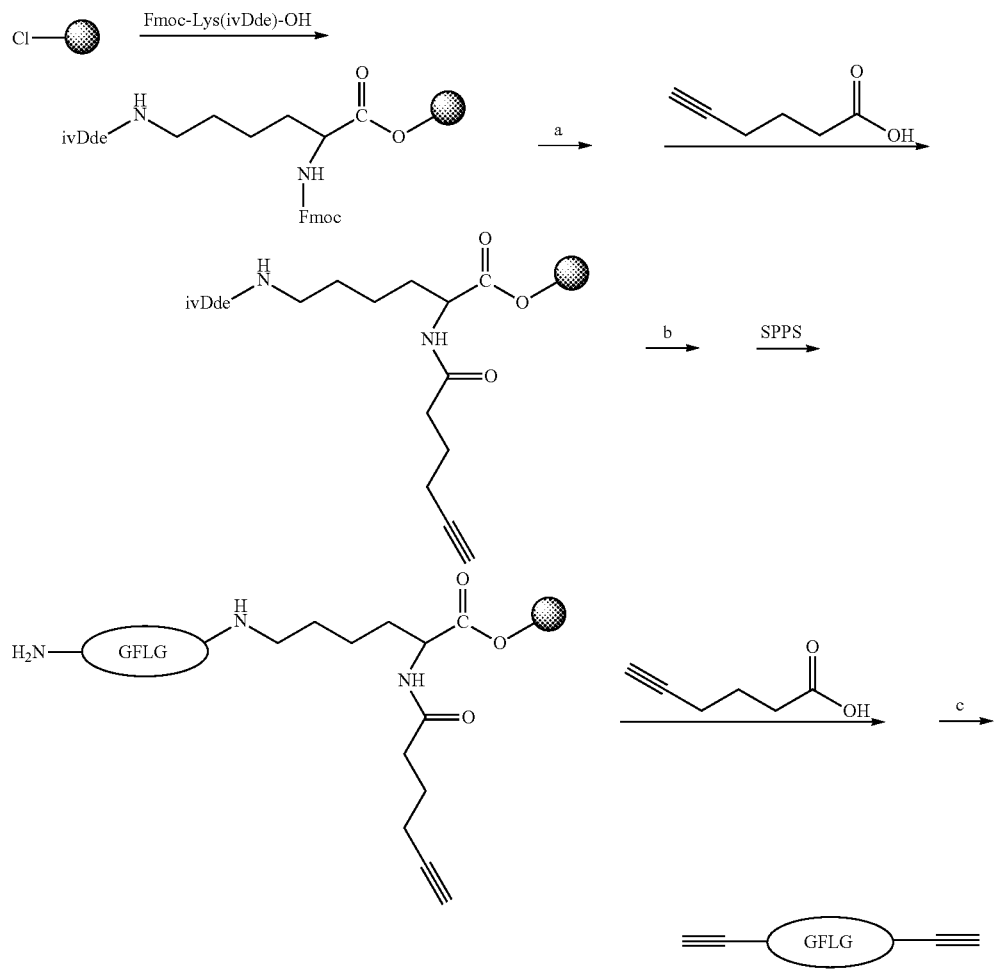
a. 20% PIP/DMF for Fmoc deprotection   b. 3% hydrazine/DMF for ivDde deprotection
c. TFA/TIS/H₂O 95:2.5:2.5 for cleavage
SCHEME 9
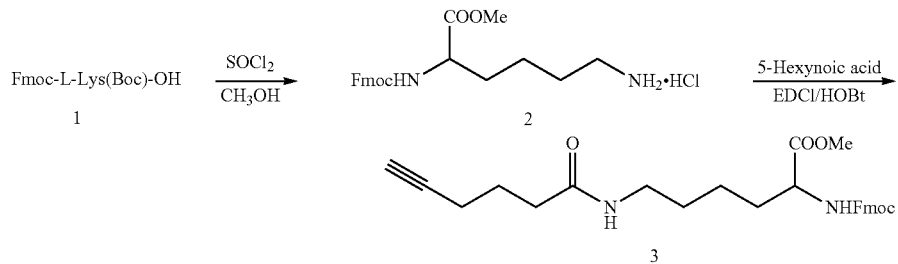

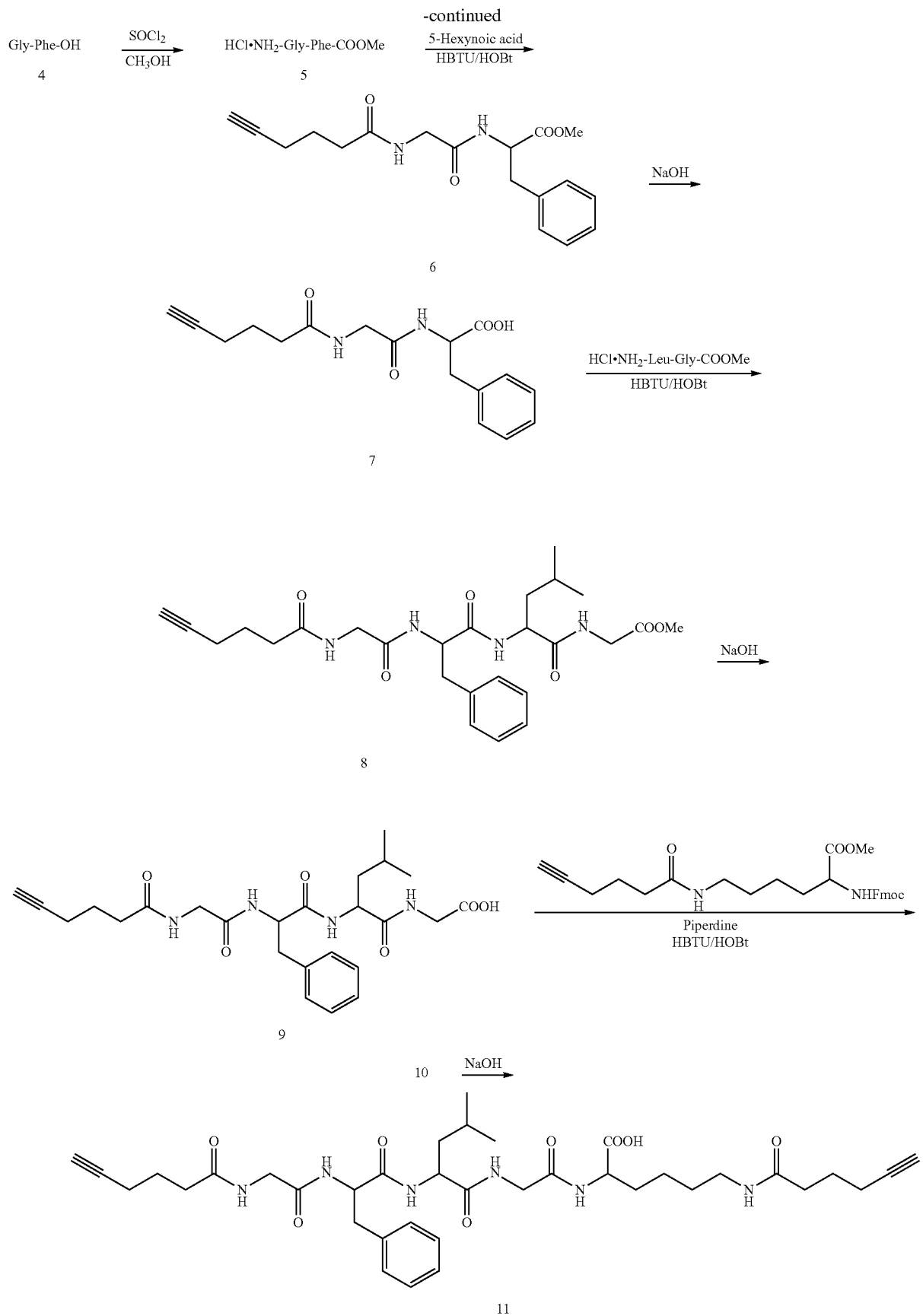

SCHEME 10
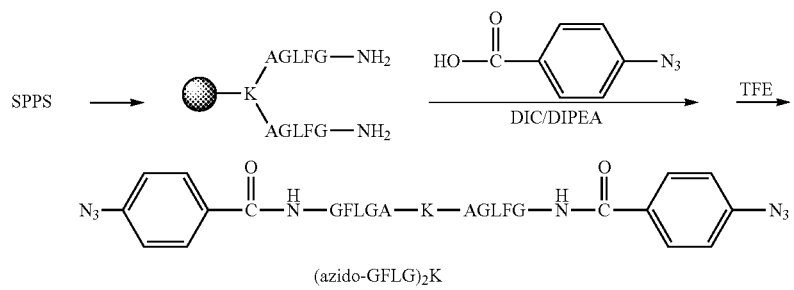
(azido-GFLG)₂K
SCHEME 11
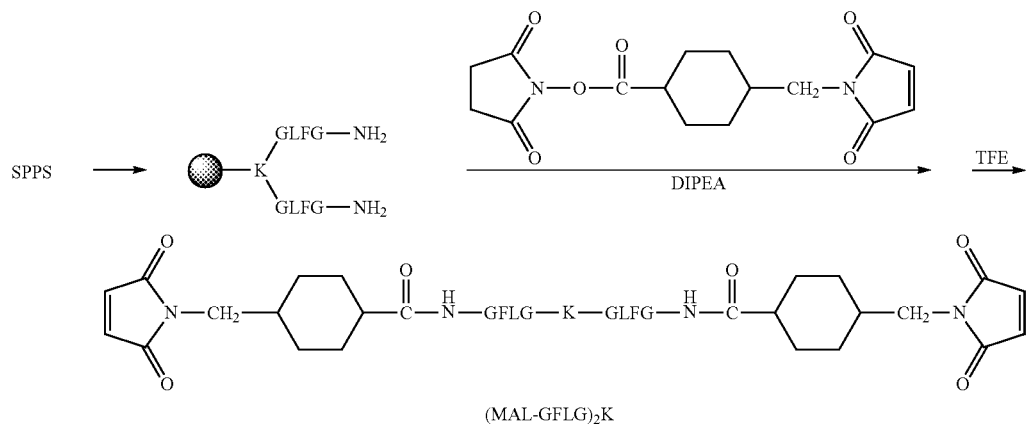
(MAL-GFLG)₂K
SCHEME 12
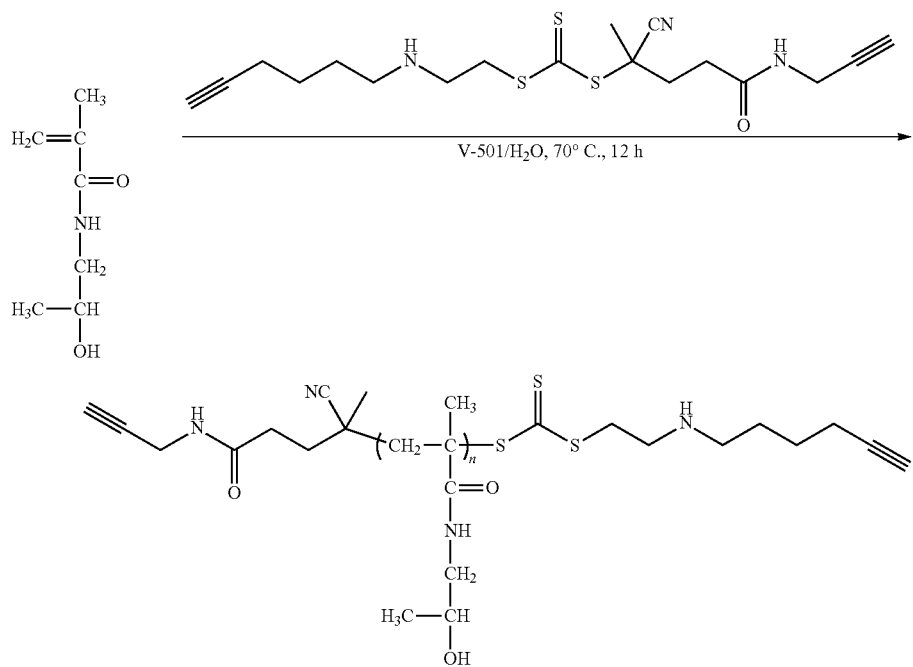

SCHEME 13
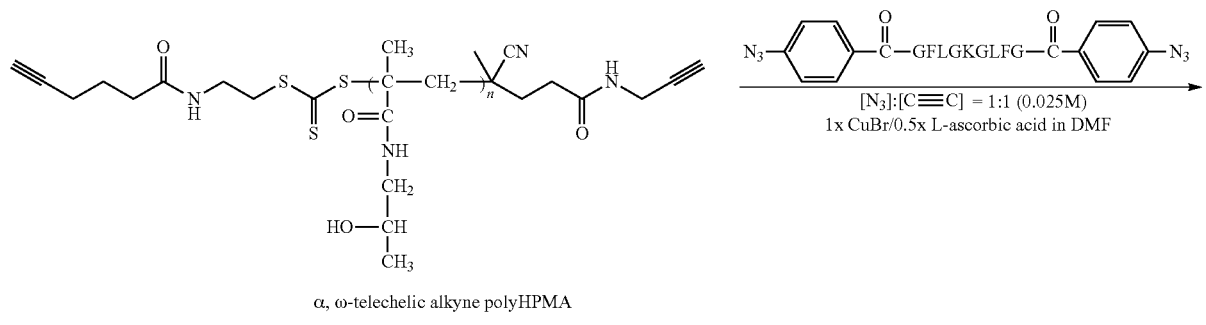
α, ω-telechelic alkyne polyHPMA
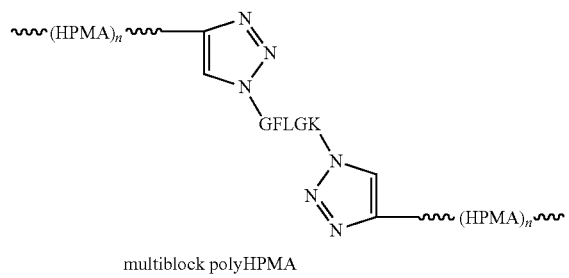
multiblock polyHPMA
SCHEME 14
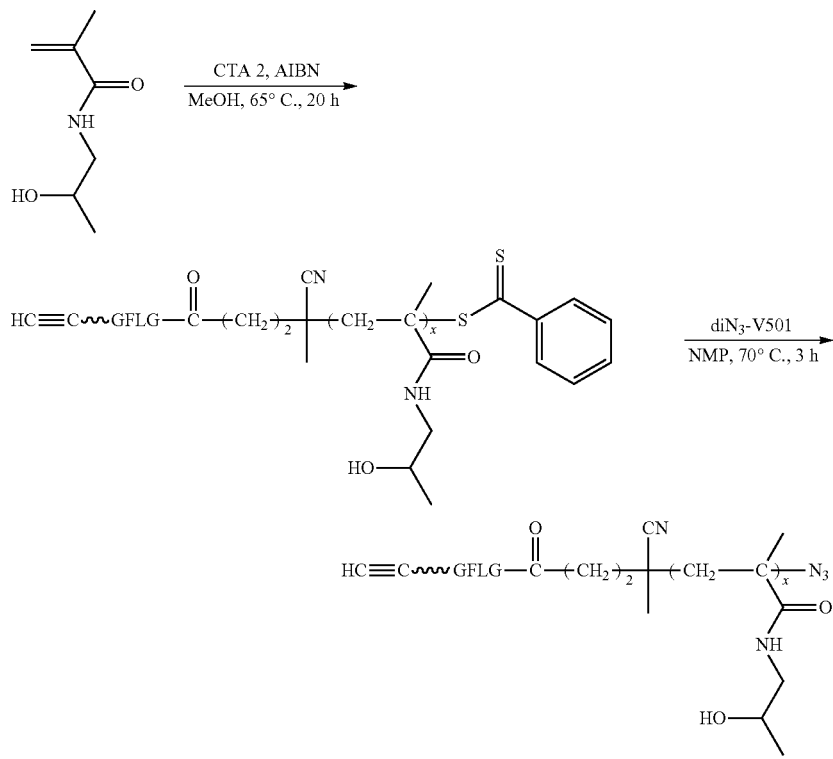
α-azide, ω-alkyne-telechelic polyHPMA SCHEME 15
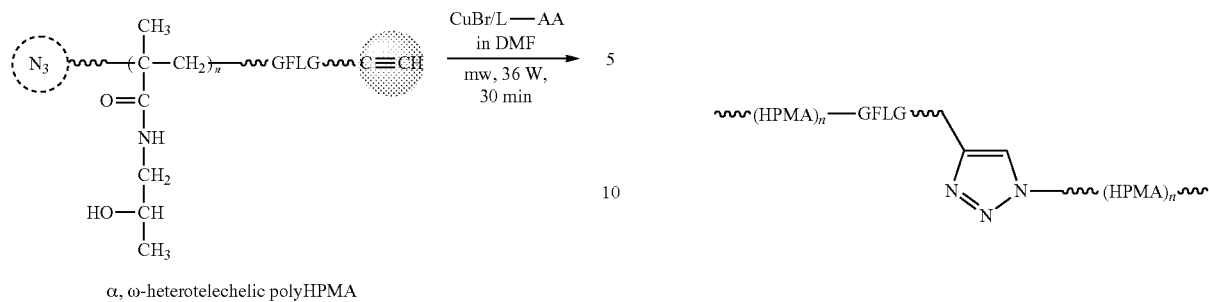
α, ω-heterotelechelic polyHPMA
SCHEME 16
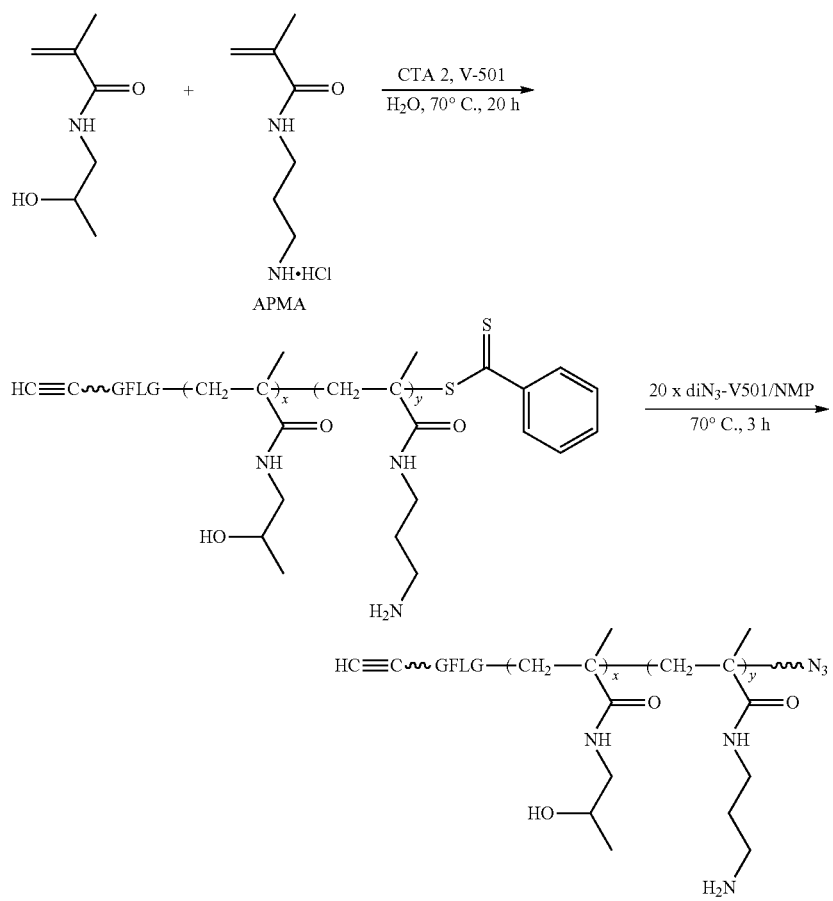
SCHEME 17
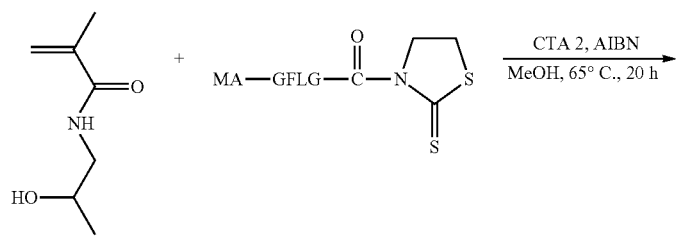

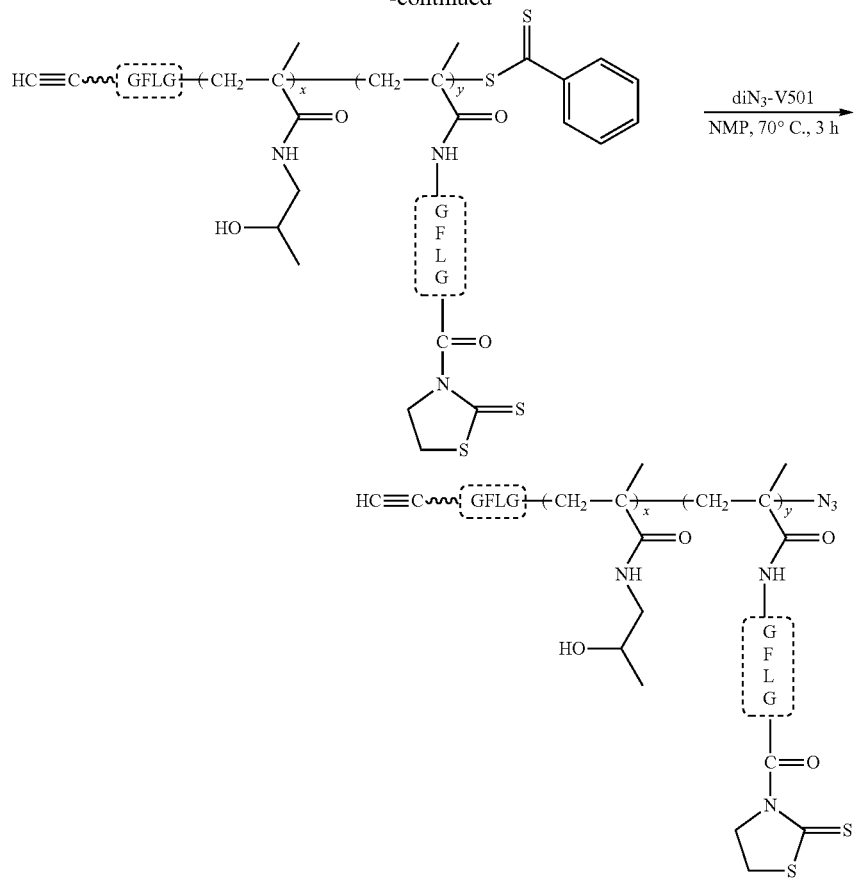
SCHEME 18
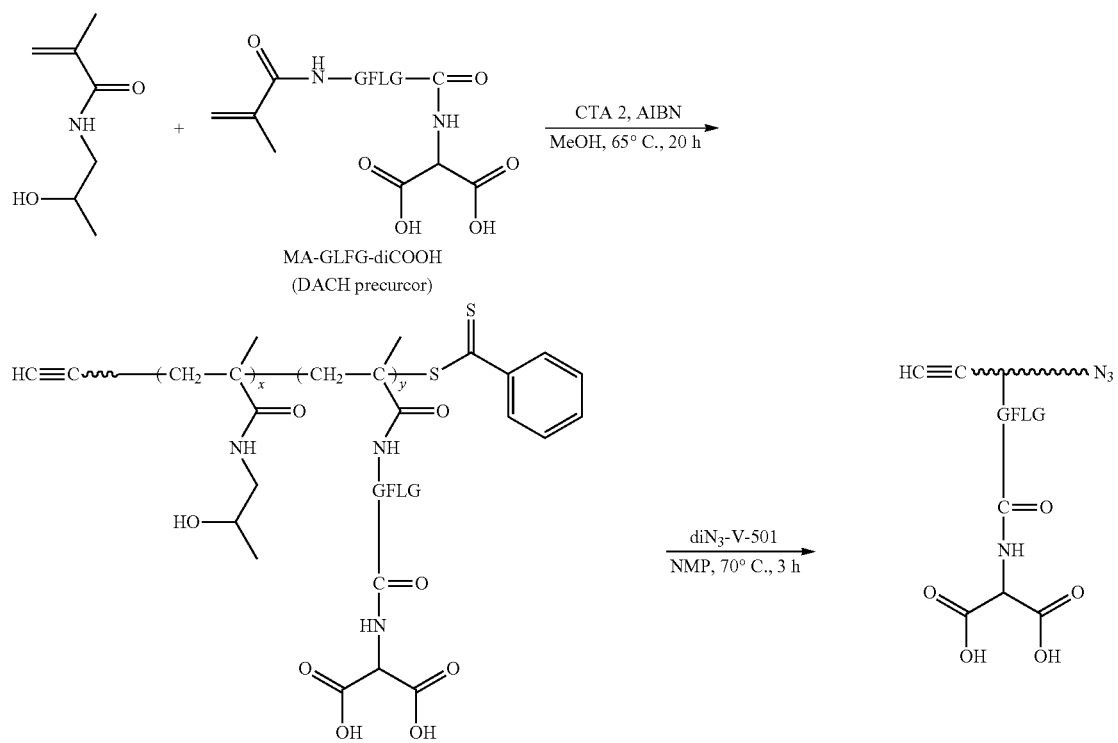

SCHEME 19
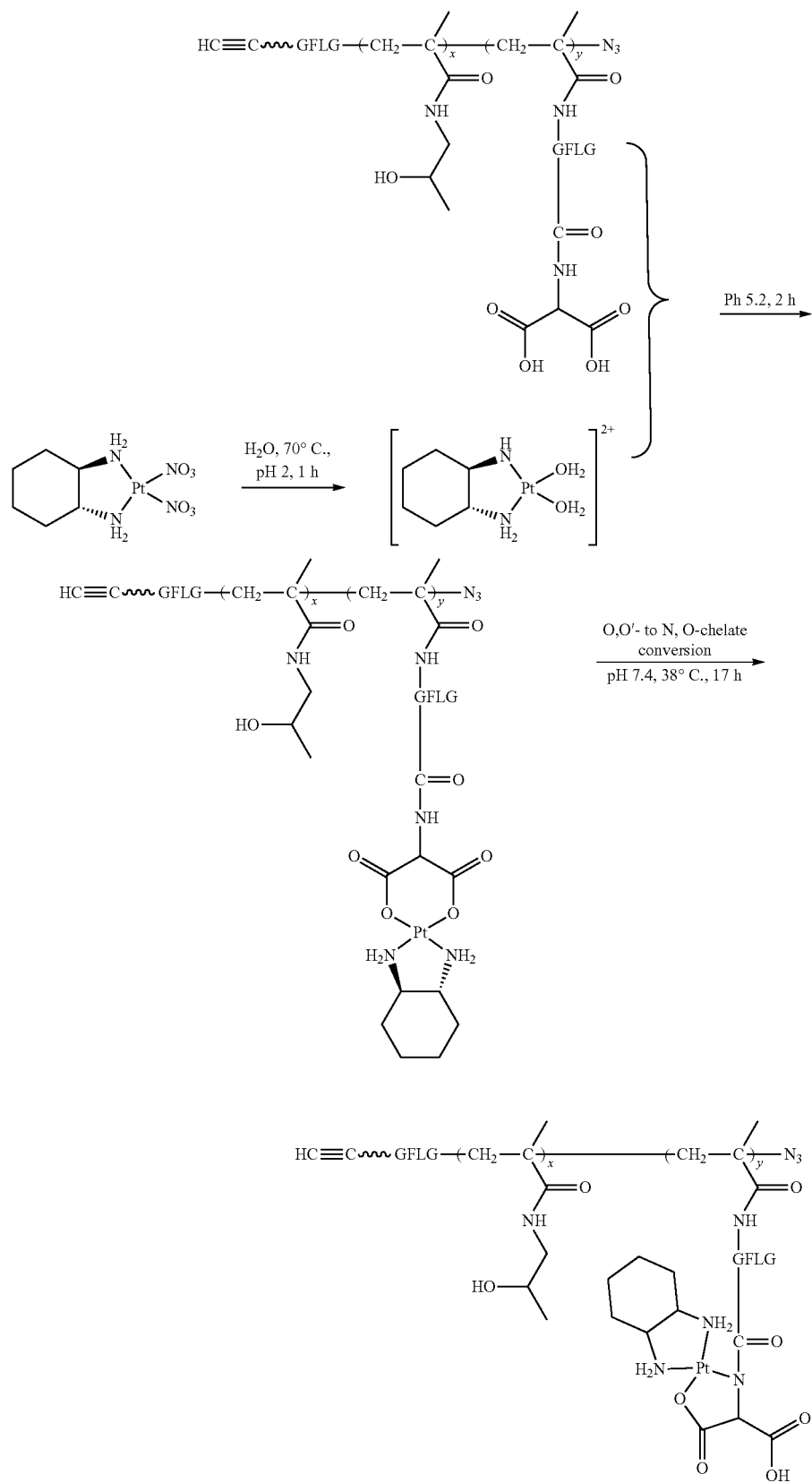

SCHEME 20
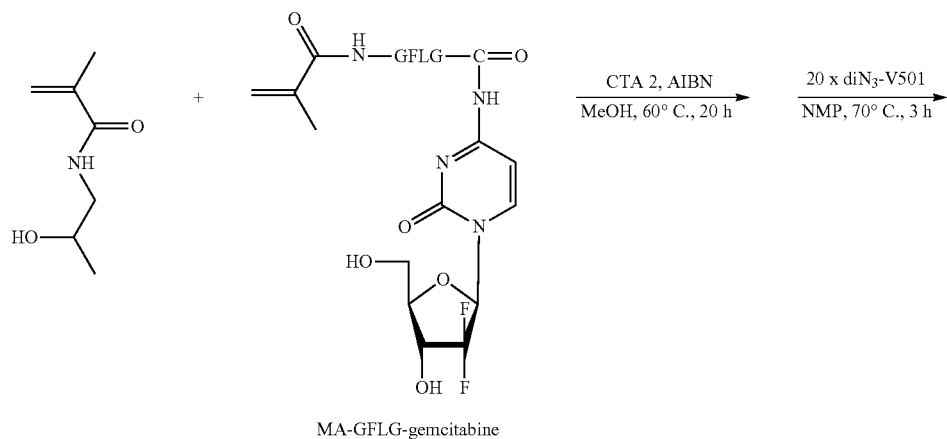
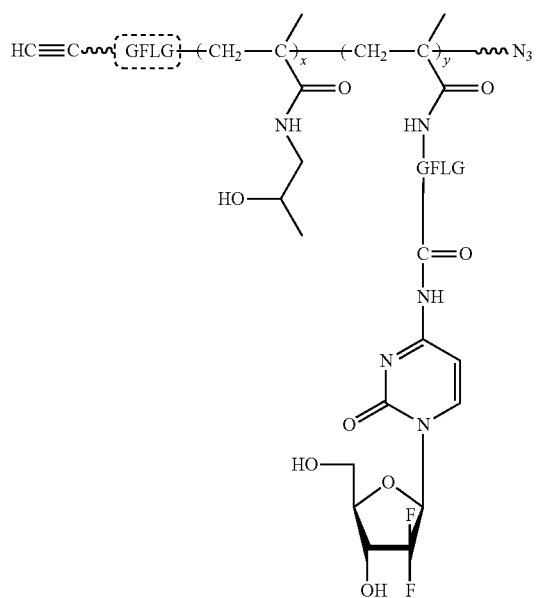
SCHEME 21
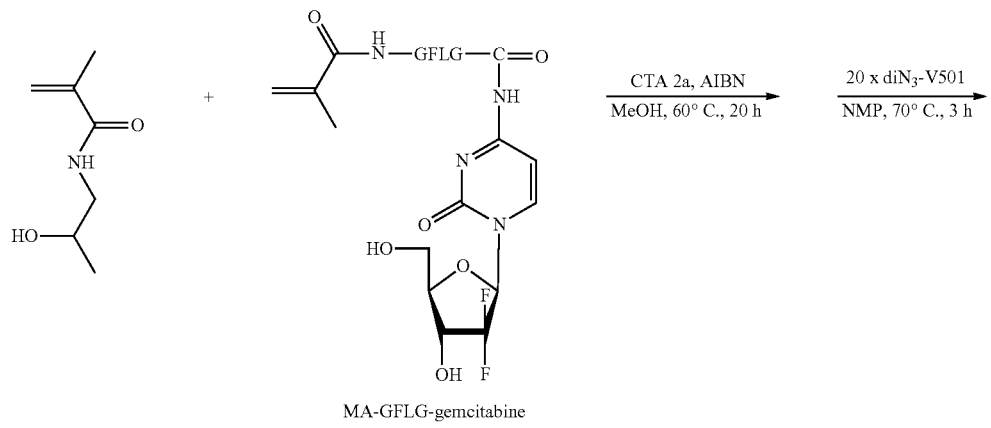

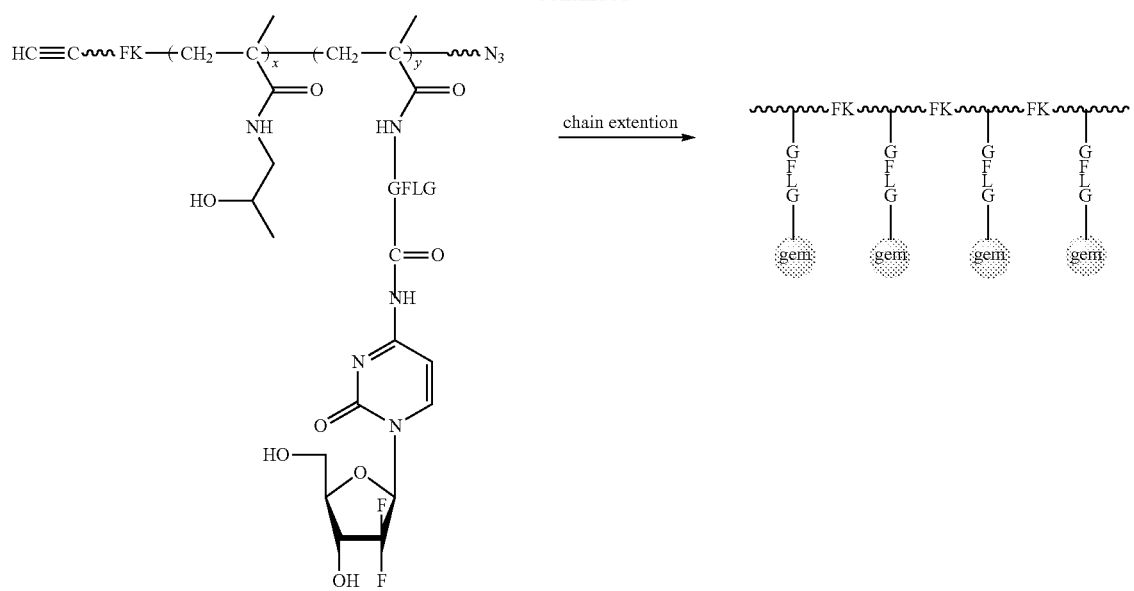
SCHEME 22
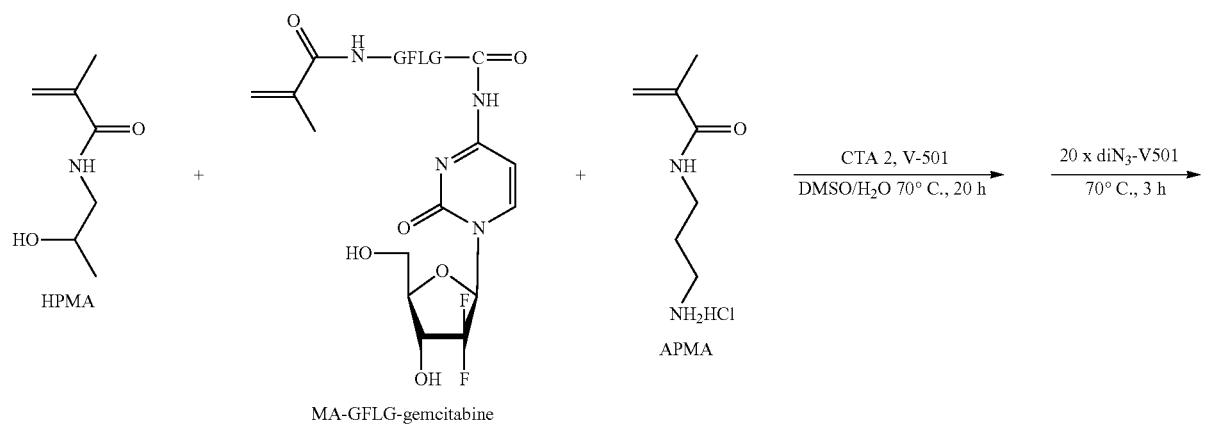
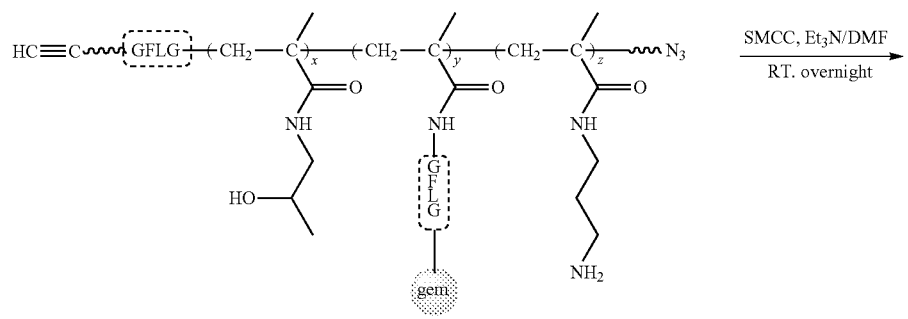

-continued
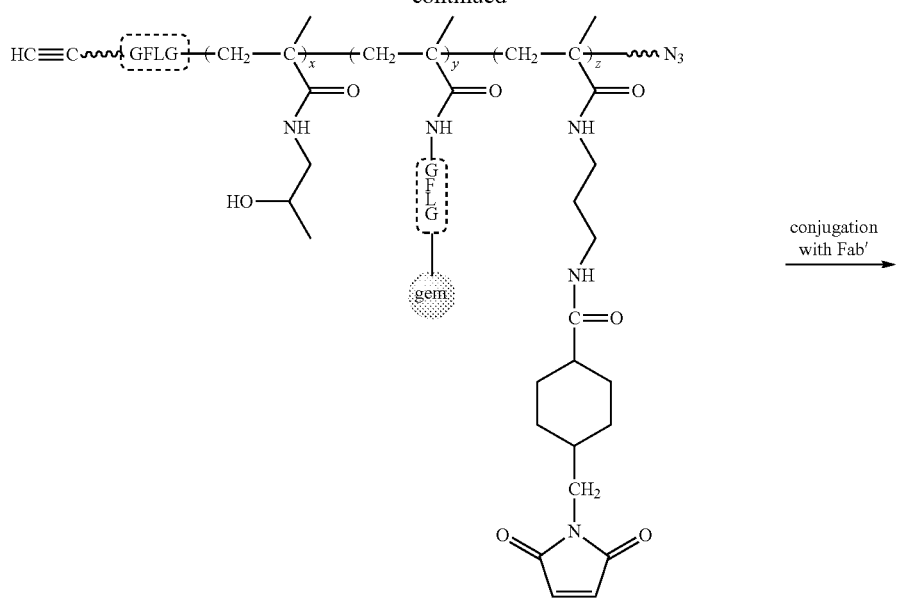
conjugation with Fab'
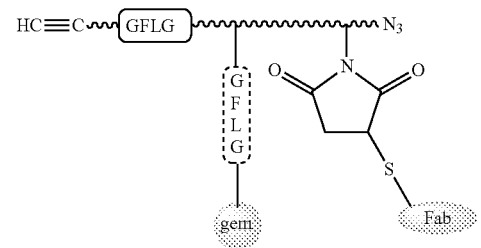
α, ω-telechelic HPMA copolymers containing gemcitabine and targeting moiety Fab'
SCHEME 23
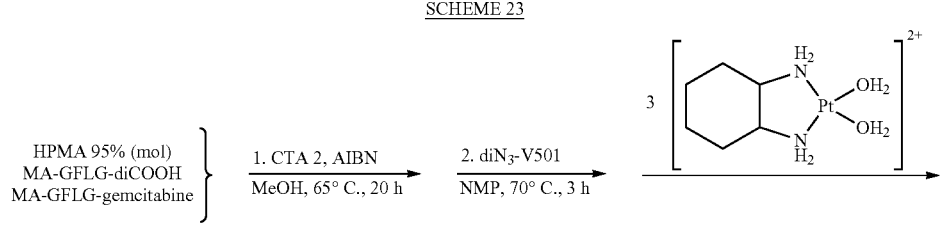
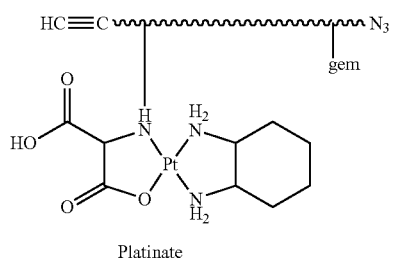
Platinate SCHEME 24
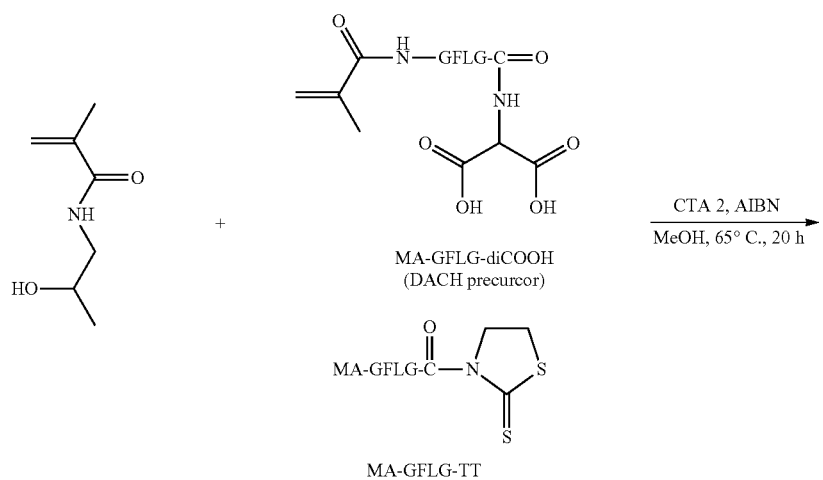
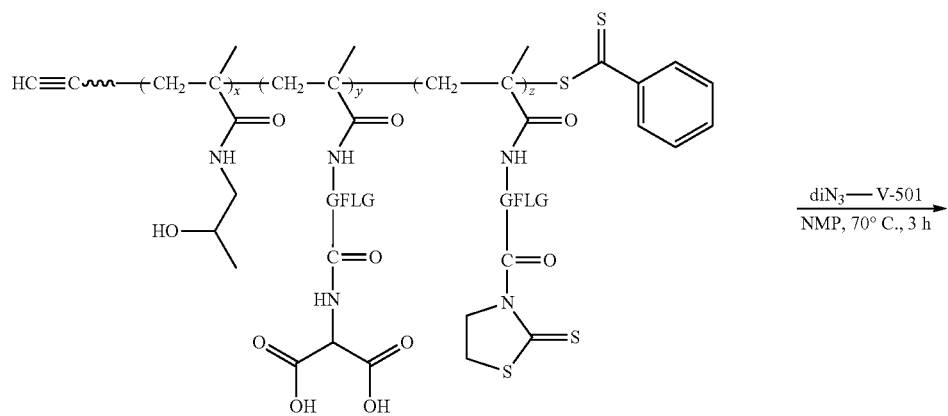
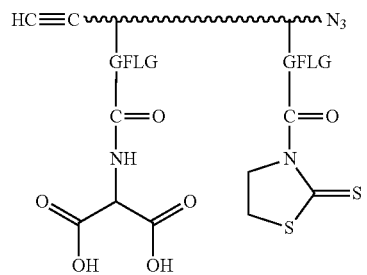
SCHEME 25
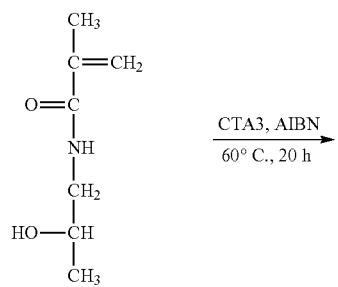
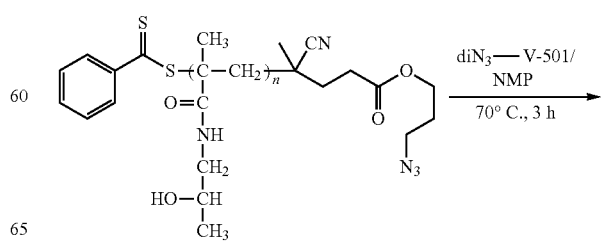
-continued

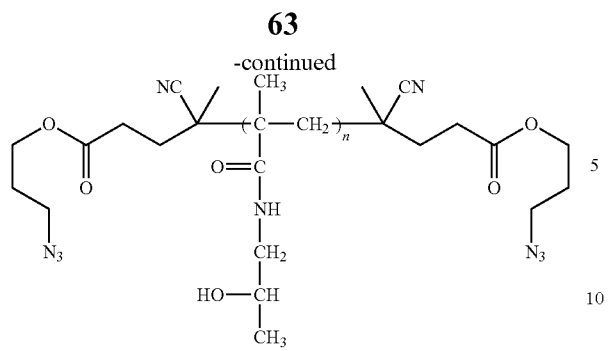
SCHEME 26
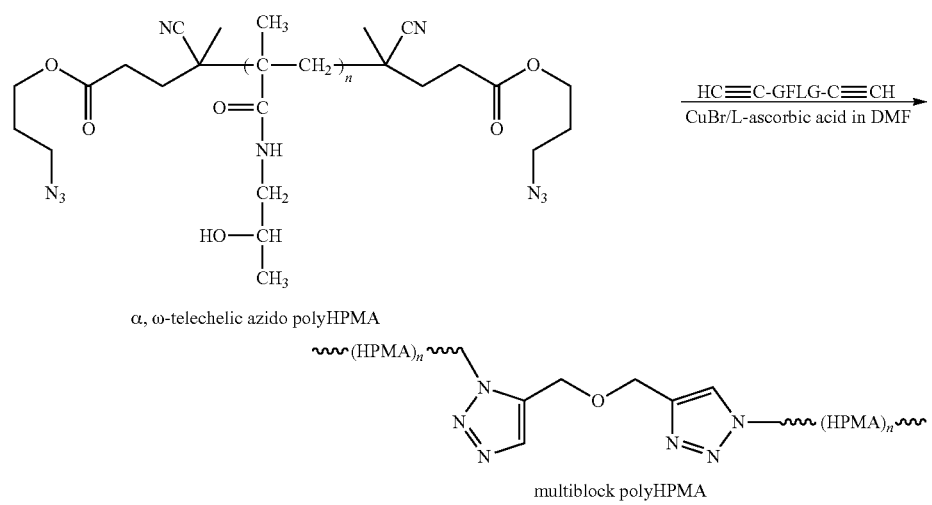
α, ω-telechelic azido polyHPMA
multiblock polyHPMA
SCHEME 27
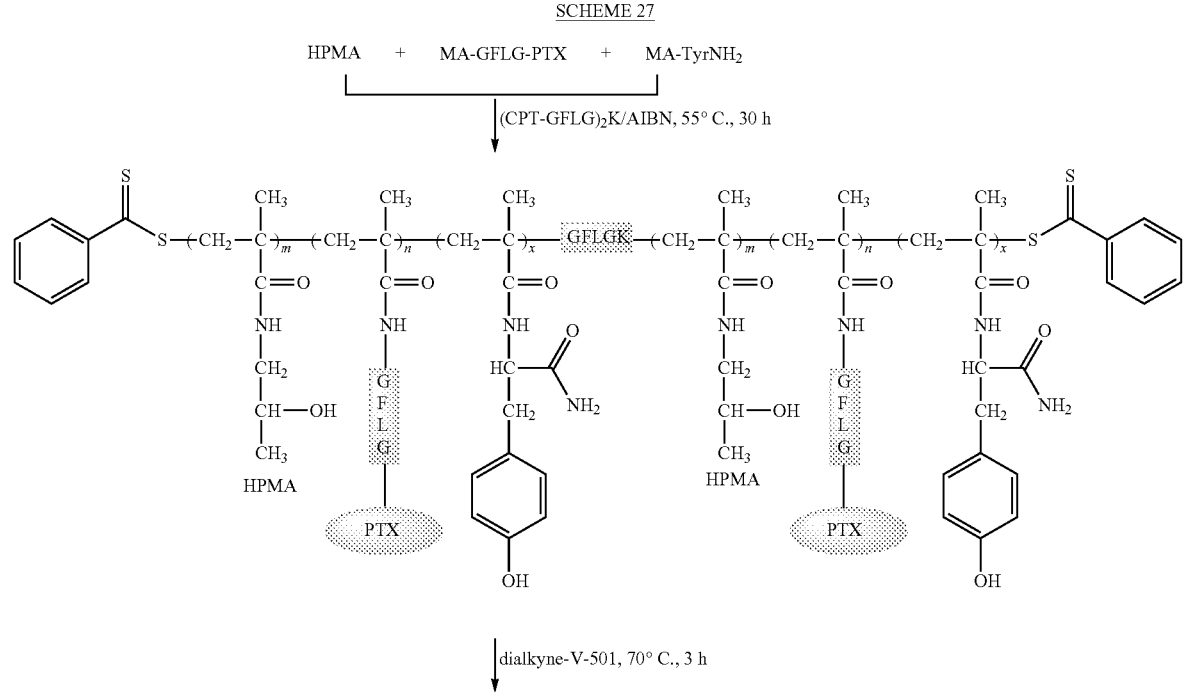

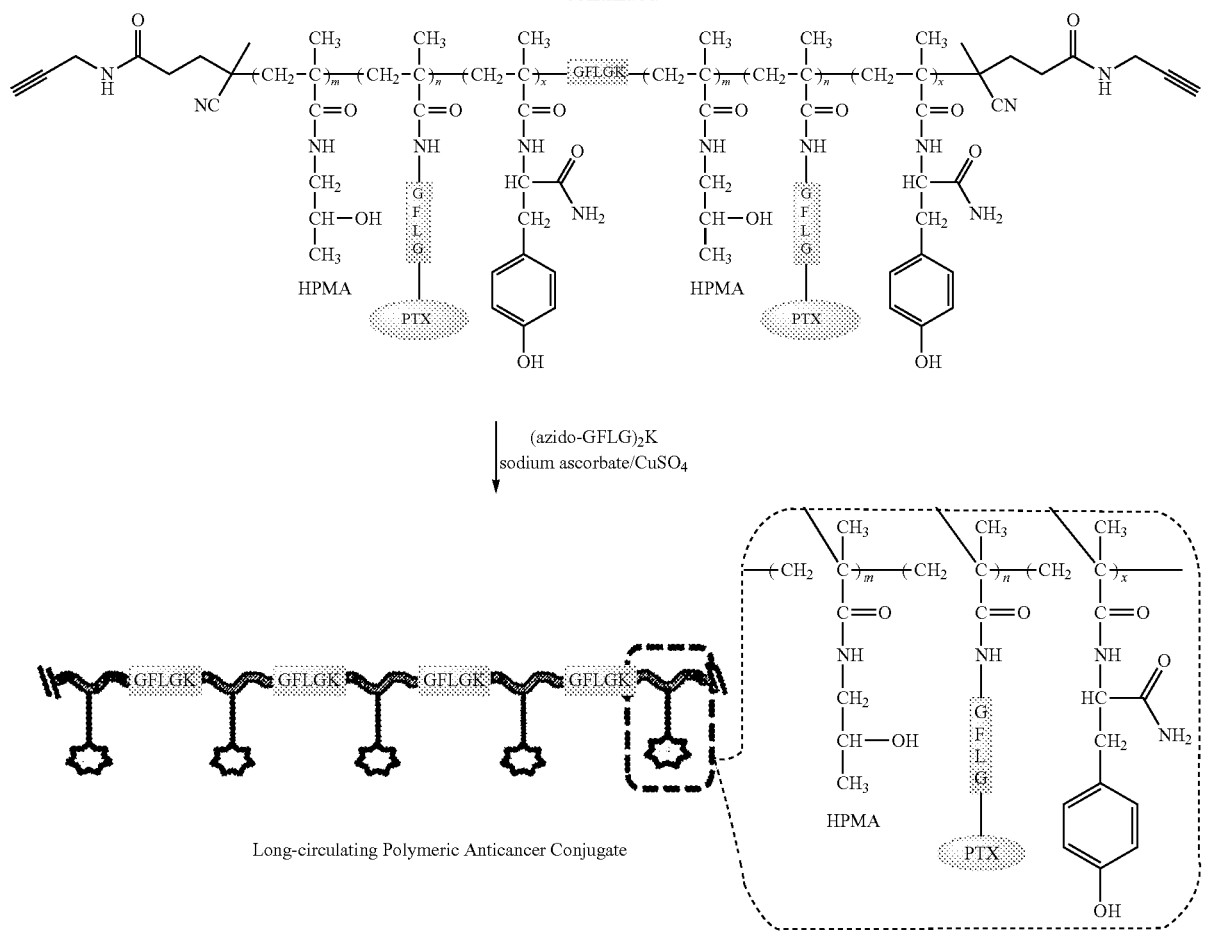
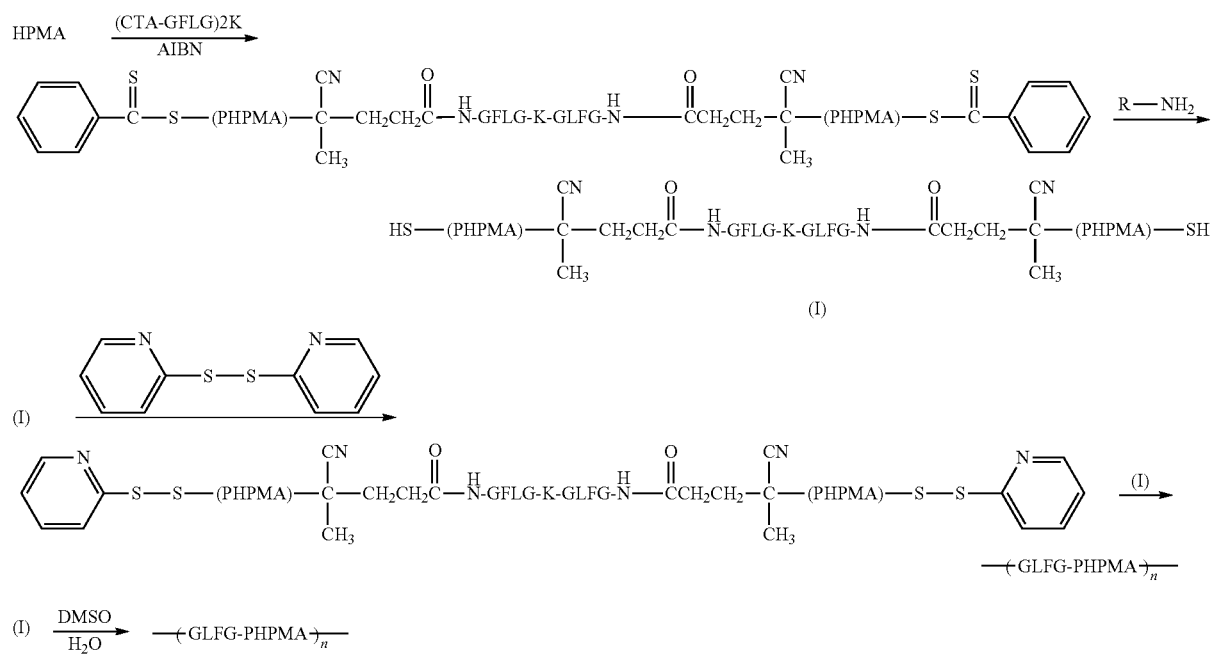
SCHEME 28

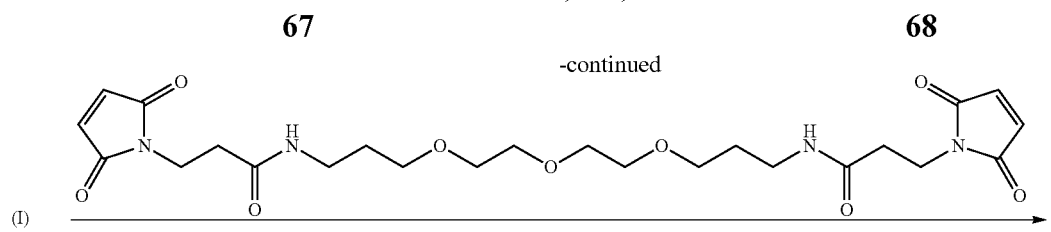
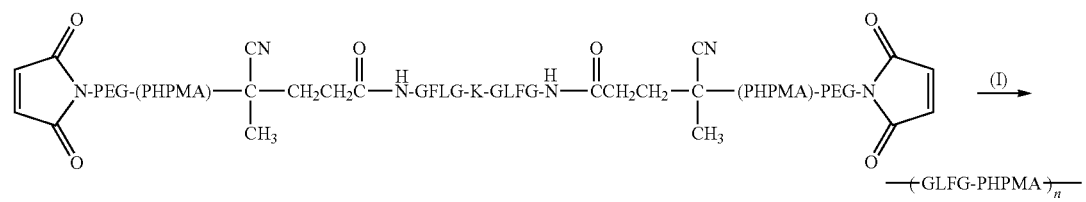
SCHEME 29
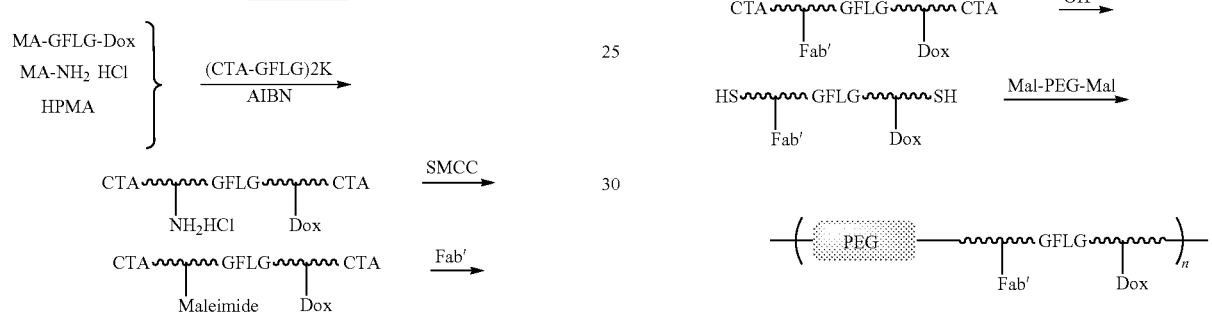
SCHEME 30
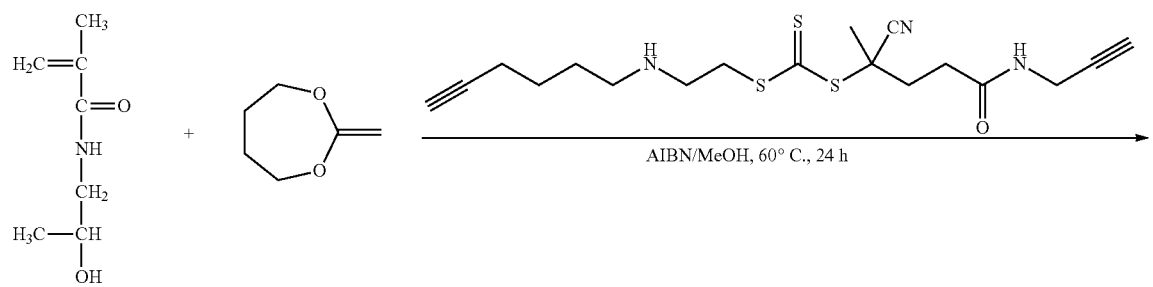
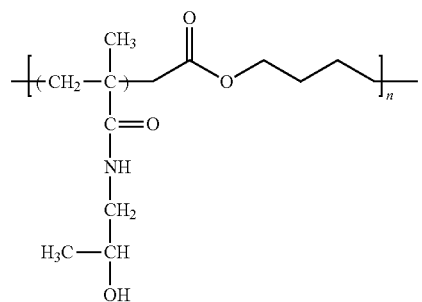

SCHEME 31
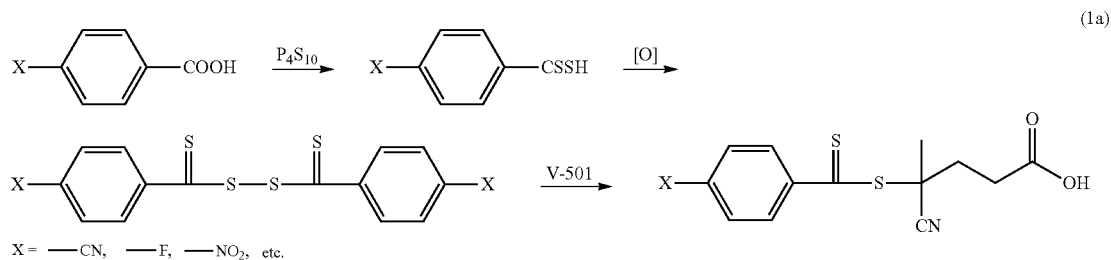
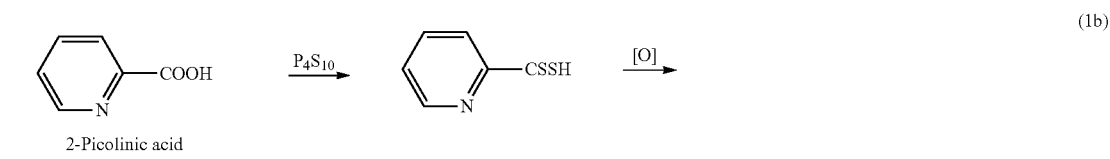
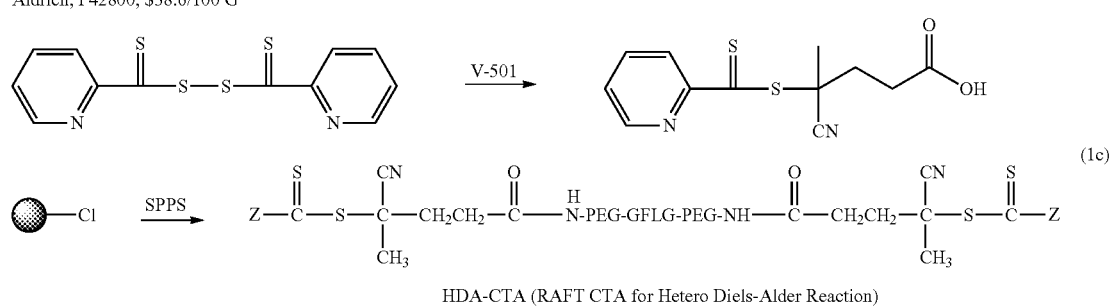
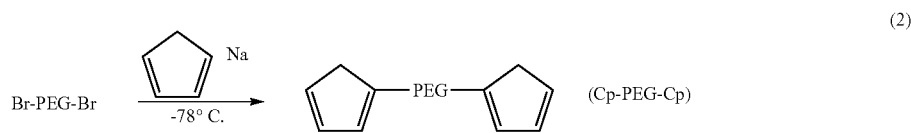
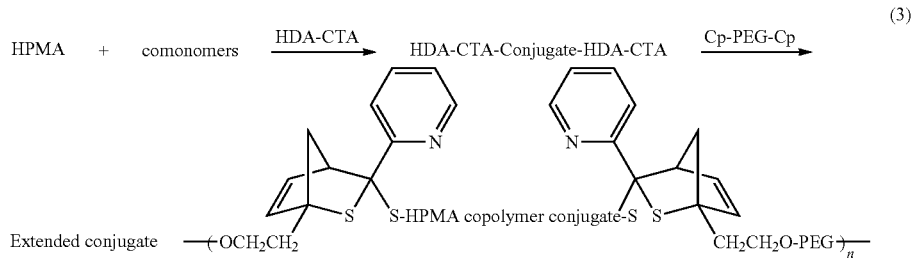
SCHEME 32
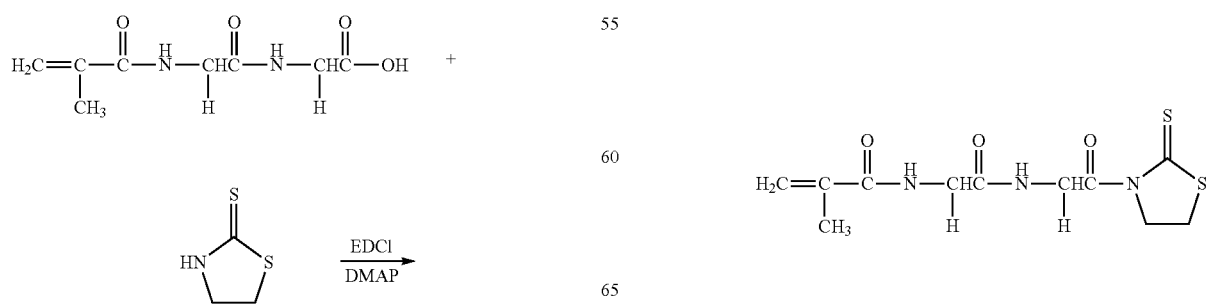

SCHEME 33
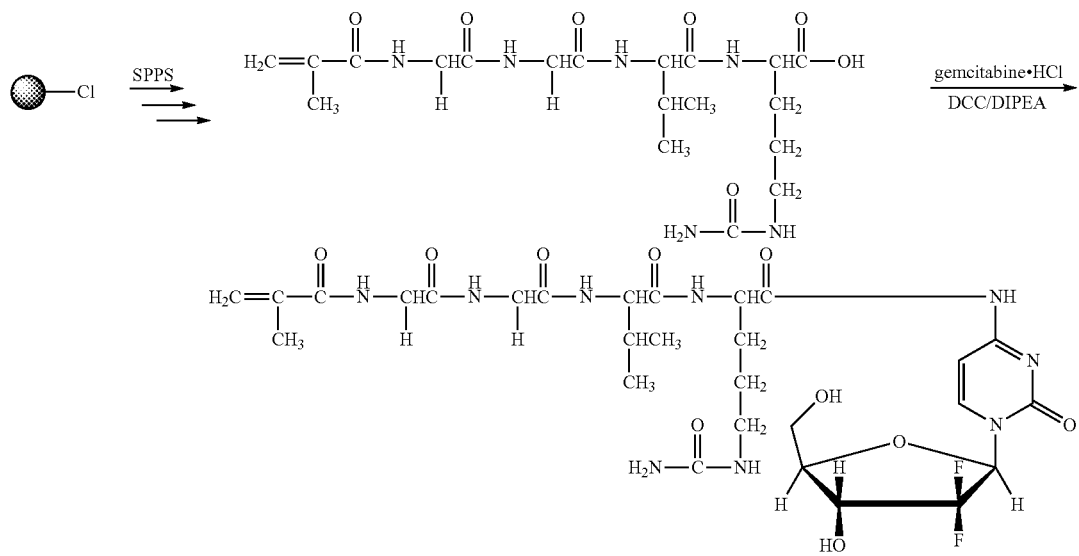
SCHEME 34
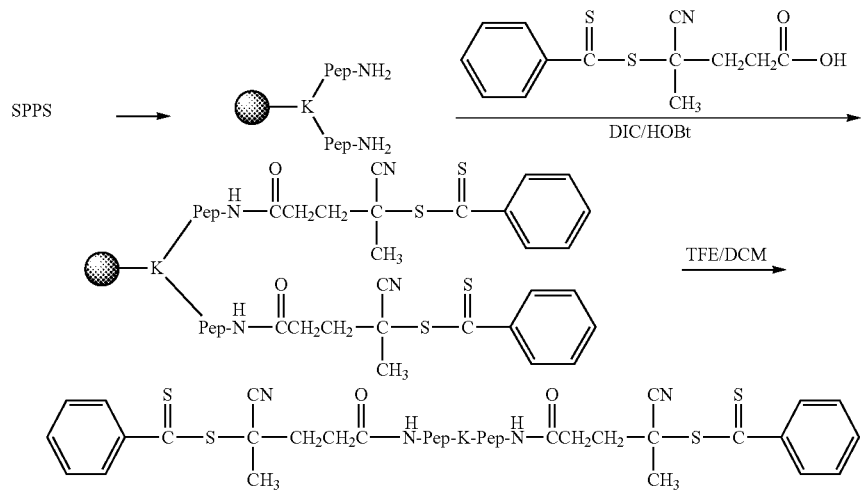
(CTA-Pep)₂K
Pep: -Val-Cit-; -Phe-Lys-; etc
SCHEME 35
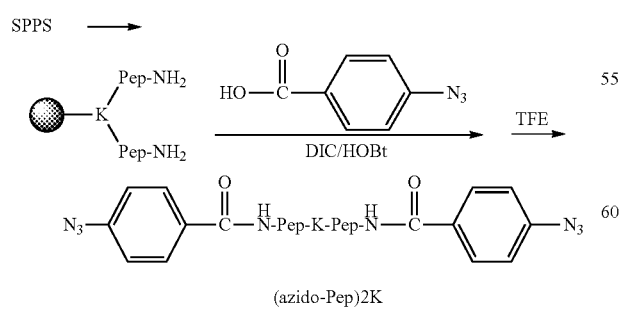
(azido-Pep)2K
Pep: -Val-Cit-; -Phe-Lys-; etc
SCHEME 36
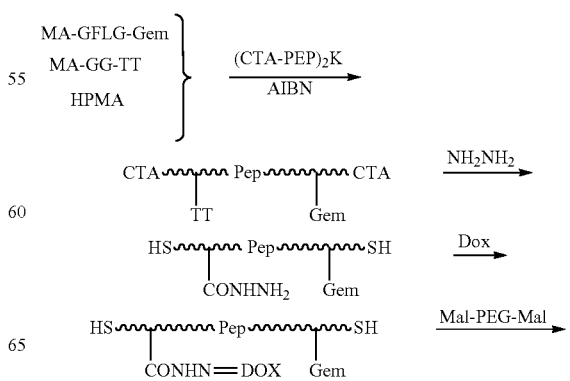

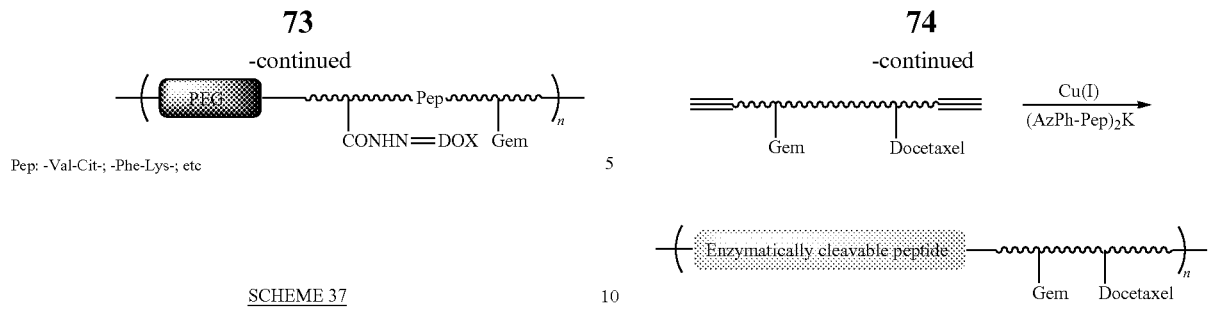

Pep: -Val-Cit-; -Phe-Lys-; etc

SCHEME 37

Pep: -Val-Cit-; -Phe-Lys-; etc

What is claimed:

1. A drug delivery conjugate or the pharmaceutically acceptable salt or ester thereof comprising two polymeric segments $P^1$ and $P^2$ covalently connected to one another by a single first cleavable peptide linker as depicted in formula I, $$P^1\text{-Gly-Phe-Leu-Gly-Lys-Gly-Leu-Phe-Gly-}P^2 \quad (I)$$

wherein an anti-cancer drug is covalently bonded to each polymeric segment via a second cleavable peptide linker, wherein each polymeric segment comprises the polymerization product of N-(2-hydroxypropyl)methacrylamide (HPMA) and a monomer of formulae II:

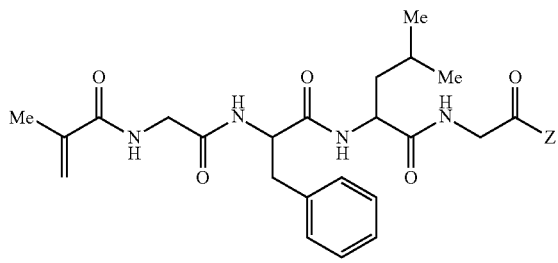

wherein Z is the anti-cancer drug, and
wherein the conjugate has a molecular weight from 50 kDa to 150 kDa.

2. The conjugate of claim 1, wherein each polymeric segment has a molecular weight less than 40 kDa.

3. The conjugate of claim 1, wherein the anti-cancer drug is paclitaxel, docetaxel, gemcitabine, a platinate, doxorubicin, geldanamycin, epirubicin, or 9-aminocamptothecin.

4. The conjugate of claim 1, wherein two or more different anti-cancer drugs are covalently bonded to the conjugate.

5. The conjugate of claim 1, wherein a targeting group is covalently attached to each polymeric segment.

6. The conjugate of claim 5, wherein the targeting group is an antibody, an antibody fragment, a saccharide, or an epitope binding peptide, or an aptamer.

7. A pharmaceutical composition comprising the conjugate of claim 1 and a pharmaceutically acceptable carrier.

8. The pharmaceutical composition of claim 7, wherein the composition is an injectable composition comprising a sterile aqueous medium as the pharmaceutically acceptable carrier.

9. A method for delivering an anti-cancer agent to a subject comprising administering the conjugate of claim 1 to the subject.

10. The conjugate of claim 3, wherein the platinate is cisplatin, carboplatin, or diaminocyclohexyl platinum.

* * * * *